US011320436B2

(12) United States Patent
Delfani et al.

(10) Patent No.: US 11,320,436 B2
(45) Date of Patent: May 3, 2022

(54) METHODS, ARRAYS AND USES THEREOF

(71) Applicant: IMMUNOVIA AB, Lund (SE)

(72) Inventors: Payam Delfani, Malmö (SE); Linda Dexlin Mellby, Dalby (SE); Anders Carlsson, Lund (SE); Björn Elleby, Bunkeflostrand (SE)

(73) Assignee: IMMUNOVIA AB, Lund (SE)

( * ) Notice: Subject to any disclaimer, the term of this patent is extended or adjusted under 35 U.S.C. 154(b) by 0 days.

(21) Appl. No.: 17/377,473

(22) Filed: Jul. 16, 2021

(65) Prior Publication Data
US 2022/0026431 A1 Jan. 27, 2022

(30) Foreign Application Priority Data
Jul. 16, 2020 (GB) ..................................... 2010970

(51) Int. Cl.
| | |
|---|---|
| *G01N 33/543* | (2006.01) |
| *G01N 33/574* | (2006.01) |
| *C07K 16/18* | (2006.01) |
| *C07K 16/28* | (2006.01) |
| *C07K 16/30* | (2006.01) |
| *C07K 16/38* | (2006.01) |
| *C07K 16/40* | (2006.01) |

(52) U.S. Cl.
CPC ....... *G01N 33/57438* (2013.01); *C07K 16/18* (2013.01); *C07K 16/2878* (2013.01); *C07K 16/3092* (2013.01); *C07K 16/38* (2013.01); *C07K 16/40* (2013.01); *G01N 33/574* (2013.01); *C07K 2317/622* (2013.01); *G01N 2800/50* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,486,530 A | 12/1984 | David et al. |
| 5,856,090 A | 1/1999 | Epstein |
| 6,258,540 B1 | 7/2001 | Lo et al. |
| 6,355,623 B2 | 3/2002 | Seidman et al. |
| 7,354,584 B2 | 4/2008 | Reed et al. |
| 8,632,983 B2 | 1/2014 | Haab et al. |
| 2004/0110219 A1 | 6/2004 | Buccholz et al. |
| 2004/0213791 A1 | 10/2004 | Bander et al. |
| 2004/0219572 A1 | 11/2004 | Chen et al. |
| 2005/0095611 A1 | 5/2005 | Chan et al. |
| 2005/0132427 A1 | 6/2005 | Nakamura et al. |
| 2005/0260639 A1 | 11/2005 | Nakamura et al. |
| 2007/0212738 A1 | 9/2007 | Haley et al. |
| 2009/0291434 A1 | 11/2009 | Cowens et al. |
| 2012/0264634 A1 | 10/2012 | Amersdorfer et al. |
| 2013/0260388 A1 | 10/2013 | Shen et al. |
| 2014/0038844 A1* | 2/2014 | Borrebaeck ........ G01N 33/6893 506/9 |
| 2016/0033511 A1 | 2/2016 | Pannell et al. |
| 2017/0153239 A1 | 6/2017 | Paik et al. |
| 2018/0136231 A1 | 5/2018 | Borrebaeck et al. |

FOREIGN PATENT DOCUMENTS

| | | |
|---|---|---|
| CA | 1 202 235 A | 3/1986 |
| CA | 2904973 A1 | 9/2014 |
| CN | 1851455 A | 10/2006 |
| CN | 101246176 A | 8/2008 |
| CN | 101451975 A | 6/2009 |
| CN | 101613748 A | 12/2009 |
| CN | 101676300 A | 3/2010 |
| CN | 101880707 A | 11/2010 |
| CN | 102201038 A | 9/2011 |
| CN | 102279264 A | 12/2011 |
| CN | 102286464 A | 12/2011 |
| CN | 111171053 A | 5/2020 |
| EP | 1736780 A1 | 12/2006 |
| JP | 2004-248575 A | 9/2004 |
| JP | 2007-051880 A | 3/2007 |
| JP | 2015-033381 A | 2/2015 |
| KR | 10-2006-0112258 A | 10/2006 |
| KR | 20110056564 A | 5/2011 |
| KR | 20130116433 A | 10/2013 |
| RU | 2421149 C2 | 6/2011 |
| WO | 98/37186 A1 | 8/1998 |
| WO | 2001/006262 A1 | 1/2001 |
| WO | 2004/031412 A2 | 4/2004 |
| WO | 2004055519 A2 | 7/2004 |
| WO | 2004/094458 A2 | 11/2004 |
| WO | 2005/004809 A2 | 1/2005 |
| WO | 2005/013682 A2 | 2/2005 |
| WO | 2005/063812 A2 | 7/2005 |
| WO | 2006/039671 A2 | 4/2006 |
| WO | 2006/110581 A2 | 10/2006 |
| WO | 2006/110599 A2 | 10/2006 |
| WO | 2006/113210 A2 | 10/2006 |
| WO | 2006/121892 A2 | 11/2006 |

(Continued)

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*

(Continued)

*Primary Examiner* — Gary Counts
(74) *Attorney, Agent, or Firm* — Robert C. Netter, Jr.; Dann, Dorfman, Herrell & Skillman

(57) ABSTRACT

The present invention provides a method for diagnosing or determining a pancreatic cancer-associated disease state comprising or consisting of the steps of: (a) providing a sample from an individual to be tested; and (b) determining a biomarker signature of the test sample by measuring the presence and/or amount in the test sample of two or more biomarkers selected from the group defined in Table A; wherein the presence and/or amount in the test sample of two or more biomarkers selected from the group defined in Table A is indicative of the pancreatic cancer-associated disease state in the individual; uses and methods of determining a pancreatic cancer-associated disease state, and methods of treating pancreatic cancer, together with arrays and kits for use in the same.

18 Claims, 9 Drawing Sheets

Specification includes a Sequence Listing.

(56) References Cited

FOREIGN PATENT DOCUMENTS

| | | |
|---|---|---|
| WO | 2007/045966 A2 | 4/2007 |
| WO | 2007/107774 A2 | 9/2007 |
| WO | 2007/122820 A1 | 11/2007 |
| WO | 2008/021174 A2 | 2/2008 |
| WO | 2008/079269 A2 | 7/2008 |
| WO | 2008/117067 A2 | 10/2008 |
| WO | 2008/127718 A2 | 10/2008 |
| WO | 2008/139169 A1 | 11/2008 |
| WO | 2008/143533 A1 | 11/2008 |
| WO | 2009/006439 A1 | 1/2009 |
| WO | 2009/062050 A2 | 5/2009 |
| WO | 2009/068857 A1 | 6/2009 |
| WO | 2009/111067 A2 | 9/2009 |
| WO | 2010/023458 A1 | 3/2010 |
| WO | 2010/102195 A2 | 9/2010 |
| WO | 2010/105235 A2 | 9/2010 |
| WO | 2011/010969 A1 | 1/2011 |
| WO | 2012/021407 A2 | 2/2012 |
| WO | 2012/120288 A2 | 9/2012 |
| WO | 2013/052480 A1 | 4/2013 |
| WO | 2013/106844 A2 | 7/2013 |
| WO | 2014/089241 A2 | 6/2014 |
| WO | 2014/141683 A1 | 9/2014 |
| WO | 2014/160499 A2 | 10/2014 |
| WO | 2015/067969 A2 | 5/2015 |
| WO | 2015/112429 A1 | 7/2015 |
| WO | 2015/157557 A1 | 10/2015 |
| WO | 2015/171736 A2 | 11/2015 |
| WO | 2015174585 A1 | 11/2015 |
| WO | 2016/124947 A1 | 8/2016 |
| WO | 2017/008388 A1 | 1/2017 |
| WO | 2017/008389 A1 | 1/2017 |
| WO | 2017/050939 A2 | 3/2017 |
| WO | 2017/194613 A2 | 11/2017 |
| WO | 2018/141804 A1 | 8/2018 |
| WO | 2019/232361 A1 | 12/2019 |

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
Galli, C., et al. "CA 19-9: handle with care" Clin Chem Lab Med. (2013) 51(7):1369-83.
Borrebaeck, C., "Precision diagnostics: moving towards protein biomarker signatures of clinical utility in cancer" Nat Rev Cancer (2017) 17(3):199-204.
Hanash, S., et al. "Mining the plasma proteome for cancer biomarkers" Nature (2008) 452(7187):571-9.
Radon, T., et al "Identification of a Three-Biomarker Panel in Urine for Early Detection of Pancreatic Adenocarcinoma" Clin Cancer Res. (2015) 21(15):3512-21.
Mayers, J., et al. "Elevation of circulating branched-chain amino acids is an early event in human pancreatic adenocarcinoma development" Nat Med. (2014) 20(10):1193-8.
Jenkinson, C., et al. "Decreased Serum Thrombospondin-1 Levels in Pancreatic Cancer Patients Up to 24 Months Prior to Clinical Diagnosis: Association with Diabetes Mellitus" Clin Cancer Res. (2016) 22(7):1734-43.
Kim, J., et al. "Detection of eraly pancreatic ductal adenocarcinoma with thrombospondin-2 and CA19-9 blood markers" Sci. Transl. Med. (2017) 12;9(398) doi: 10.1126/scitranslmed.aah5583.
Bossuyt, P., et al. "STARD 2015: an updated list of essential items for reporting diagnostic accuracy studies" BMJ. (2015) 351:h5527.
Batabyal, P., et al. "Association of diabetes mellitus and pancreatic adenocarcinoma: a meta-analysis of 88 studies" Ann Surg Oncol. (2014) 21(7):2453-62.
Wang, F., et al. "The relationship between diabetes and pancreatic cancer" Mol Cancer. (2003) 2:4.
Lopez-Lazaro, M. "Pancreatic cancer formation is gradual" ResearchGate (2017) doi10.13140/RG.2.2.16865.92009.
Notta, F., et al. "A renewed model of pancreatic cancer evolution based on genomic rearrangement patterns" Nature (2016) 538(7625):378-82.
Chari, S., et al. "Probability of Pancreatic Cancer Following Diabetes: A Population-Based Study" Gastroenterology (2005) 129(2):504-511.
Aggarwal, G., et al. "New-onset diabetes in pancreatic cancer: A study in the primary care setting" Pancreatology (2012) 12(2):156-161.
Roberts, S., et al. "The PDZ protein discs-large (DLG): the 'Jekyll and Hyde' of the epithelial polarity proteins" FEBS J. (2012) 279(19):3549-58.
Kranjec, C., et al. "Restoration of MAGI-1 expression in human papillomavirus-positive tumor cells induces cell growth arrest and apoptosis" J Virol. (2014) 88(13):7155-69.
Lan, X., et al. "Whole-exome sequencing identifies variants in invasive pituitary adenomas" Oncol Lett. (2016)12(4):2319-28.
Huang, Y., et al. "Four genetic polymorphisms of lymphotoxin-alpha gene and cancer risk: a systematic review and meta-analysis" PLoS One (2013) 8(12):e82519.
Human Protein Atlas "Expression of LTA in cancer—The Human Protein Atlas" (2017) [Available from: http://www.proteinatlas.org/ENSG00000226979-LTA/cancer].
Mamidi, S., et al. "The complement system in cancer: Ambivalence between tumour destruction and promotion" Immunobiology (2017) 222(1):45-54.
Pio, R., et al. "The role of complement in tumor growth" Adv Exp Med Biol. (2014):772:229-62.
Grande, C., et al. "Interleukin-2 for the treatment of solid tumors other than melanoma and renal cell carcinoma" Anticancer Drugs (2006) 17(1):1-12.
Nobili C., et al, "Prolonged survival of a patient affected by pancreatic adenocarcinoma with massive lymphocyte and dendritic cell infiltration after interleukin-2 immunotherapy" Report of a case. Tumori (2008) 94(3):426-30.
Stark, A., et al. "Pancreatic Ductal Adenocarcinoma" (2015) [Available from: https://www.pancreapedia.org/reviews/pancreatic-ductal-adenocarcinoma.
Leek, J., et al. "sva: Surrogate Variable Analysis" R package version 3.22.0. (2016) available at http://bioconductor.org/packages/release/bioc/html/sva.html.
Delfani, P., et al. "Technical Advances of the Recombinant Antibody Microarray Technology Platform for Clinical Immunoproteomics" PLoS One (2016) 11(7):e0159138.
Borrebaeck, C., et al. "Recombinant antibodies for the generation of antibody arrays" Methods Mol Biol (2011) 785:247-62.
Zola, "Monoclonal Antibodies: A manual of techniques" CRC Press, Florida (1988) pp. 17-61.
Hurrell, "Monoclonal Hybridoma Antibodies: Techniques and Applications" CRC Press, Florida (1982) pp. 1-57.
Thompson, et al. "CLUSTAL W: improving the sensitivity of progressive multiple sequence alignment through sequence weighting, position-specific gap penalties and weight matrix choice" Nucl. Acid Res. (1994) 22:4673-4680.
Kunik, A., et al. (2012) "Paratome: an online tool for systematic identification of antigen-binding regions in antibodies based on sequence or structure" Nucl. Acids Res., 40:W521-W524.
Wu, et al. "An analysis of the sequences of the variable regions of Bence Jones proteins and myeloma light chains and their implications for antibody complementarity" J. Exp. Med. (1970) 132:211-250.
Chothia, et al. "Canonical structures for the hypervariable regions of immunoglobulins" J. Mol. Biol., (1987) 196:901-917.
Lefranc, et al. (2003) "IMGT unique numbering for immunoglobulin and T cell receptor variable domains and Ig superfamily V-like domains" Dev. Comp. Immunol. 27:55-77.
Lefrranc, et al. "IMGT unique numbering for immunoglobulin and T cell receptor constant domains and Ig superfamily C-like domains" Dev. Comp. Immunol. (2005) 29:185-203.
Harlow, et al. "Antibodies: A Laboratory Manual" (1988) Cold Spring Harbor Press, New York, pp. 139-243.
Chothia, et al. "Conformations of immunoglobulin hypervariable regions" (1989) Nature, 342:877-883.

(56) References Cited

OTHER PUBLICATIONS

Seeja, et al., "Identification of co-regulated signature genes in pancreas cancer—a data mining approach" Advanced Intelligent Computing Theories and Applications: With Aspects of Theoretical and Methodological Issues; 4th International Conference on Intelligent Computing, ICIC 2008, Shanghai, China, Sep. 15-18, 2008.
Cheng, et al., "Molecular mechanism for USP7-mediated DNMT1 stabilization by acetylation" Nature Communications (2015) 6(1):7023.
Ballehaninna, U.K., et al., "The clinical utility of serum CA 19-9 in the diagnosis, prognosis and management of pancreatic adenocarcinoma: An evidence based appraisal" J. Gastrointest. Oncol. (2012) 3(2):105-19.
Ballehaninna, U.K., et al., "Serum CA 19-9 as a Biomarker for Pancreatic Cancer—A Comprehensive Review" Indian J. Surg. Oncol. (2011) 2(2):88-100.
Bettac, L., "Complement in Pancreatic Disease—Perpetrator or Savior?" Front. Immunol. (2017) 8:15.
Del Villano, B.C., et al., "Radioimmunometric Assay for a Monoclonal Antibody-Defined Tumor Marker, CA 19-9" Clin. Chem. (1983) 29(3):549-552.
Felder, M., et al., "MUC16 (CA125): tumor biomarker to cancer therapy, a work in progress" Molecular Cancer (2014) 13:129.
Ferguson, T.W., et al., "Cystatin C as a biomarker for estimating glomerular filtration rate" Curr. Opin. Nephrol. Hypertens. (2015) 24:295-300.
Goonetilleke, K.S., et al., "Systematic review of carbohydrate antigen (CA 19-9) as a biochemical marker in the diagnosis of pancreatic cancer" Eur. J. Surg. Oncol. (2007) 33:266-270.
Gronborg, M., et al., "Comprehensive Proteomic Analysis of Human Pancreatic Juice" J. Proteome Res. (2004) 3:1042-1055.
Haeno, H., et al., "Computational Modeling of Pancreatic Cancer Reveals Kinetics of Metastasis Suggesting Optimum Treatment Strategies" Cell (2012) 148:362-375.
Hippisley-Cox, J., et al., "Identifying patients with suspected pancreatic cancer in primary care: derivation and validation of an algorithm" Br. J. Gen. Pract. (2012) 62(594):e38-e45.
Ilic, M., et al., "Epidemiology of pancreatic cancer" World J. Gastroenterol. (2016) 22(44): 9694-9705.
Kauffmann, A., et al., "Microarray data quality control improves the detection of differentially expressed genes" Genomics (2010) 95:138-142.
Kauffmann, A., et al., "arrayQualityMetrics—a bioconductor package for quality assessment of microarray data" Bioinformatics (2009) 25(3):415-416.
Keane, M.G., et al., "A case-control study comparing the incidence of early symptoms in pancreatic and biliary tract cancer" BMJ Open (2014) 4:e005720.
Keane, M.G., et al., "Sociodemographic Trends in the Incidence of Pancreatic and Biliary Tract Cancer in UK Primary Care" PLoS ONE (2014) 9(9): e108498.
Kenner, B.J., et al., "Early Detection of Pancreatic Cancer—a Defined Future Using Lessons From Other Cancers: A White Paper" Pancreas (2016) 45(8):1073-9.
Kloppel, G., et al., "Chronic Pancreatitis and the Differential Diagnosis Versus Pancreatic Cancer" Arch. Pathol. Lab. Med. (2009) 133:382-387.
Kos, J., et al., "Cysteine proteinases and their inhibitors in extracellular fluids: Markers for diagnosis and prognosis in cancer" Intl. J. Biol. Markers (2000) 15(1):84-89.
Lacroix, M., et al., "Residue Lys57 in the Collagen-Like Region of Human L-Ficolin and Its Counterpart Lys47 in H-Ficolin Play a Key Role in the Interaction with the Mannan-Binding Lectin-Associated Serine Proteases and the Collectin Receptor Calreticulin" J. Immunol. (2009) 182:456-465.
Lee, M.J., et al., "Identification of Human Complement Factor B as a Novel Biomarker Candidate for Pancreatic Ductal Adenocarcinoma" J. Proteome Res. (2014) 13:4878-4888.
Liu, L., et al., "The clinical utility of CA125/MUC16 in pancreatic cancer: A consensus of diagnostic, prognostic and predictive updates by the Chinese Study Group for Pancreatic Cancer (CSPAC)" Intl. J. Oncol. (2016) 48:900-907.
Misek, D.E., et al., "Eady Detection and Biomarkers in Pancreatic Cancer" J. Nat. Comp. Cancer Net. (2007) 5:1034-1041.
Ni, X.G., et al., "The Ubiquitin-Proteasome Pathway Mediates Gelsolin Protein Downregulation in Pancreatic Cancer" Mol. Med. (2008) 14(9-10): 582-589.
Pang, W.W., et al., "Can the acute-phase reactant proteins be used as cancer biomarkers?" Intl. J. Biol. Markers (2010) 25(1):1-11.
Poruk, K.E., et al., "The Clinical Utility of CA 19-9 in Pancreatic Adenocarcinoma: Diagnostic and Prognostic Updates" Curr. Mol. Med. (2013) 13(3):340-351.
Sall, A., et al., "Generation and analyses of human synthetic antibody libraries and their application for protein microarrays" Protein Engineering Design Selection (2016) 29(10):427-437.
Shahbazi, S., et al., "Characterization of the interaction between von Willebrand factor and osteoprotegerin" J. Thrombosis Haemostasis (2007) 5:1956-1962.
Shi, W., et aql., "Osteoprotegerin is up-regulated in pancreatic cancers and correlates with cancer-associated new-onset diabetes" BioScience Trends (2014) 8(6):322-326.
Stapley, S., et al., "The risk of pancreatic cancer in symptomatic patients in primary care: a large case-control study using electronic records" Brit. J. Cancer (2012) 106:1940-1944.
Steinberg, W., "The Clinical Utility of the CA 19-9 Tumor-Associated Antigen" Am. J. Gastroenterol. (1990) 85(4):350-355.
Yoneyama, T., et al., "Identification of IGFBP2 and IGFBP3 As Compensatory Biomarkers for CA19-9 in Early-Stage Pancreatic Cancer Using a Combination of Antibody-Based and LC-MS/MS-Based Proteomics" PLoS ONE (2016) 11(8):e0161009.
Zhang, Z., et al., "Cancer Proteomics: In Pursuit of "True" Biomarker Discovery" Cancer Epidemiol. Biomarkers Prev. (2005) 14(10):2283-6.
Sumiyoshi, K., et al., "Biosynthesis and Secretion of MHC Class III Gene Products (Complement C4 and Factor B) in the Exocrine Pancreas" J. Gastroenterol. (1997) 32:367-373.
Mantovani, L.T., et al., "Folate Binding Protein Distribution in Normal Tissues and Biological Fluids from Ovarian Carcinoma Patients as Detected by the Monoclonal Antibodies MOv18 and MOv19" Eur. J. Cancer (1994) 30A(3):363-369.
Faille, D., et al., "Biomarkers for the risk of thrombosis in pancreatic adenocarcinoma are related to cancer process" Oncotarget (2018) 9(41):26453-26465.
Fredolini, C., et al., "Systematic assessment of antibody selectivity in plasma based on a resource of enrichment profiles" Scientific Reports (2019) 9:8324.
McGuigan, A., et al., "Pancreatic cancer: A review of clinical diagnosis, epidemiology, treatment and outcomes" World J. Gastroenterol. (2018) 24(43):4846-4861.
Mellby, L.D., et al., "Serum Biomarker Signature-Based Liquid Biopsy for Diagnosis of Early-Stage Pancreatic Cancer" J. Clin. Oncol. (2018) 36:2887-2894.
Orth, M., et al., "Pancreatic ductal adenocarcinoma: biological hallmarks, current status, and future perspectives of combined modality treatment approaches" Radiation Oncology (2019) 14:141.
Rawla, P., et al., "Epidemiology of Pancreatic Cancer: Global Trends, Etiology and Risk Factors" World J. Oncol. (2019) 10(1):10-27.
Singhi, A.D., et al., "Early Detection of Pancreatic Cancer: Opportunities and Challenges" Gastroenterology (2019) 156:2024-2040.
Copur, M.S., et al., "Hereditary vs Familial Pancreatic Cancer: Associated Genetic Syndromes and Clinical Perspective" Oncology (2020) 34(6):196-201.
Goggins, M., et al., "Management of patients with increased risk for familial pancreatic cancer: updated recommendations from the International Cancer of the Pancreas Screening (CAPS) Consortium" Gut (2020) 69:7-17.
Juiz, N.A., et al., "Pancreatic Cancer Heterogeneity Can Be Explained Beyond the Genome" Frontiers Oncology (2019) 9:246.

(56) References Cited

OTHER PUBLICATIONS

Klein, A.P., et al., "Prospective Risk of Pancreatic Cancer in Familial Pancreatic Cancer Kindreds" Cancer Research (2004) 64:2634-2638.
Scheufele, F., et al., "Treatment of pancreatic cancer-neoadjuvant treatment in borderline resectable/locally advanced pancreatic cancer" Transl Gastroenterol. Hepatol. (2019) 4:32.
Peterson, G.M., "Familial Pancreatic Cancer" Semin Oncol. Oct. 2016 ; 43(5): 548-553.
Siegel, R.L., et al., "Cancer Statistics, 2021" CA Cancer J. Clin. (2021) 71:7-33.
Trevethan, R., et al., "Sensitivity, Specificity, and Predictive Values: Foundations, Pliabilities, and Pitfalls in Research and Practice" Front. Public Health (2017) 5:307.
Klein, A.P., et al., "Prospective Risk of Pancreatic Cancer in Familial Pancreatic Cancer Kindreds" (2004) Cancer Res., 64:2634-2638.
Petersen, G.M., "Familial Pancreatic Cancer" (2016) Semin. Oncol., 43(5):548-553.
Trevethan, R., "Sensitivity, Specificity, and Predictive Values: Foundations, Pliabilities, and Pitfalls in Research and Practice" (2017) Front. Public Health, 5:307.
Lignelid, H., et al., "Cystatin C in the human pancreas and gut: an immunohistochemical study of normal and neoplastic tissues" (1992) Virchows Archiv. A Pathol. Anat., 421:491-495.
Zhang, P., et al., "Development of serum parameters panels for the early detection of pancreatic cancer" (2014) Int. J. Cancer, 134:2646-2655.
Kunovsky, L., et al., "The Use of Biomarkers in Early Diagnosis of pancreatic Cancer" (2018) Canadian J. Gastroenter. Hepatol., 2018:5389820.
Kim, J., et al., "Detection of Early Pancreatic Ductal Adenocarcinoma Using Thrombospondin-2 and CA19-9 Blood Markers" (2017) Sci. Transl. Med., 9(398):eaah5583.
Markocka-Maczka, K., "Von Willebrand Factor (vWF) in Plasma of Patients with Pancreatic Carcinoma" (2002) Wspolczesna Onkologia, 6:322-326 [Abstract only].
Muniyan, S., et al., "MUC16 Contributes to the Metastasis of Pancreatic Ductal Adenocarcinoma through Focal Adhesion Mediated Signaling Mechanism" (2016) Genes Cancer, 7:110-124.
Shi, W., et al., "Osteoprotegerin is Up-Regulated in Pancreatic Cancers and Correlates with Cancer-Associated New-Onset Diabetes" (2014) BioScience Trends, 8:322-326.
Aptamer, Wikipedia: The Free Encyclopedia, Wikimedia Foundation, Available from https://en.wikipedia.org/wiki/Aptamer [Retrieved Feb. 23, 2012], Feb. 2012.
Crnogorac-Jurcevic, et al., "Proteomic Analysis of Chronic Pancreatitis and Pancreatic Adenocarcinoma" Gastroenterology, (2005) 129:1454-1463.
Orr, F. W., et al. "Detection of a complement derived chemo tactic factor for tumor cells in human inflammatory and neoplastic effusions" (1983) 110(1):41-7.
Fujiwara, et al. "Transforming activity of the lymphotoxin-B receptor revealed by expression screening" (2005) Biochem. & Biophys. Res. Com., 338(2):1256-1262.
Geetha, et al., "Assessment of Immunity Status in Patients with Pancreatic Cancer" J. Clin. Biochem. Nutr,, (2006) vol. 39, pp. 18-26.
Ingvarsson, J. et al. "Detection of pancreatic cancer using antibody microarray-based serum protein profiling. Proteomics" (2008) 8(11):2211-2219.
Jiang, et al.,"Angiomotin and angiomotin like proteins, their expression and correlation with angiogenesis and clinical outcome in human breast cancer" BMC Cancer (2006) 6:16.
Karayiannakis, et al., "Serum vascular endothelial growth factor levels in pancreatic cancer patients correlate with advanced and metatastatic disease and poor prognosis" Cancer Letters (2003) 194:119-124.
Li, et al., "Cyclophilin A Is Overexpressed in Human Pancreatic Cancer Cells and Stimulates Cell Proliferation through CD147" Cancer (2006) 106:2284-2294.
Li, et al., "Expression of Syk and VEGF-D Protein in Pancreatic Cancer and Their Clinical Signfiicance" Chinese J. Cancer Prevention & Treatment (2008) 15(15):1166-1168 [Abstract only].
Meng, et al., "Overexpression of NDC80 is correlated with prognosis of pancreatic cancer and regulates cell proliferation" Am J Cancer Res (2015) 5(5):1730-1740.
Monti, et al., "The CC Chemokine MCP-1/CCL2 in Pancreatic Cancer Progression: Regulation of Expression and Potential Mechanisms of Antimalignant Activity" Cancer Res, (2003) 63:7451-7461.
Pauly, et al., "Protein Expression Profiling of Formalin-Fixed Paraffin-Embedded Tissue Using Recombinant Antibody Microarrays" Journal of Proteome Research (2013) 12(12):5943-5953.
Pepe, et al., "Phases of Biomarker Development for Early Detection of Cancer" J. Nat. Cancer Inst. (2001) 93(14):1054-1061.
Szajda, et al., "Carbohydrate markers of pancreatic cancer" Biochem Society Trans. (2011) 39(1):340-3.
Xie, et al. (2006) "Mining of microarray, proteomics, and clinical data for improved identification of chronic fatigue syndrome" Critical Assessment of Microarray Data Analysis Conference, Durham, North Carolina.
Zhang, et al., "Expression of c-erbB-2 oncogene protein, epidermal growth factor receptor, and TGF-B1 in human pancreatic ductal adenocarcinoma" Hepatobiliary & Pancreatic Diseases International (2002) 1:620-623.
Zhou, et al., "Clinical Research and Empirical Study of Combination Treatment with Gemcitabine Chemotherapy and Huai'er Granula on Pancreatic Cancer" Master's Thesis Full-Text Database, Medicine and Health Sciences, (2009) 5:E72-130 [Abstract only].
Duell, et al., "Inflammation, Genetic Polymorphisms in Proinflammatory Genes TNF-A, RANTES and CCR5, and Risk of Pancreatic Adenocarcinoma" Cancer Epidemiology, Biomarkers and Prevention (2006) 15(4):726-731.
Bloomston, et al. "Fibrinogen gamma overexpression in pancreatic cancer identified by large-scale proteomic analysis of serum samples" Cancer Research, (2006) 66, 5:2592-2599.
Garcea, et al. "Molecular prognostic markers in pancreatic cancer: A systematic review" European Journal of Cancer (2005) 41, 15:2213-2236.
Gry, et al. "Correlations between RNA and protein expression profiles in 23 human cell lines" BMC Genomics (2009) 10: 365.
Chen, et al. "Discordant protein and mRNA expression in lung adenocarcinomas" Molecular and Cellular Proteomics (2002) 1: 304-313.
Alarcon-Segovia, et al. "Antibody penetration into living cells" Clin. Exp. Immunol. (1979) 35:364-375.
Sousa-Abreu, et al. "Global signatures of protein and mRNA expression levels" Mol. BioSyst. (2009) 5:1512-1526.
Avrameas, et al. "Polyreactive anti-DNA monoclonal antibodies and a derived peptide as vectors for the intracytoplasmic and intranuclear translocation of macromolecules" Proc. Nat. Acad. Sci. USA (1998) 95:5601-5606.
Yanase, et al. "Nuclear localising anti-DNA antibodies enter cells via caveoli and modulate expression of caveolin and p53" J Autoimmun (2005) 24(2):145-151.
Wolff, et al. Pathology. In: Kufe DW et al., editors. Holland-Frei Cancer Medicine, 6th edition. Hamilton (ON): BC Decker; 2003. Available from http://www.ncbi.nim.nih.gov/books/NBK12710/.
Zhao, et al. "Comparative Serum Glycoproteomics Using Lectin Selected Sialic Acid Glycoproteins with Mass Spectrometric Analysis: Application to Pancreatic Cancer Serum" (2006) J. Proteome Res. 5:1792-1802.
NCBI entry for C1—Complement C1 Inhibitor Protein—MeSH—NCBI (2006) (available from http://www.ncbi.nlm.nih.gov/mesh/68050718).
Kang, et al. "Normal C1 inhibitor mRNA expression level in type I hereditary angioedema patients: newly found C1 inhibitor gene mutations" Allergy (2006) 61:260-264.
Phillips, C. "Study Raises Concerns about using cancer cell" National Cancer Institute Cancer Bulletin (2011) 8:23.

(56) References Cited

OTHER PUBLICATIONS

Applied Biosystems, "TAQMAN Gene Expression Assays Product Guide" (2005).
NCBI entry for C5—C5-MeSH-NCBI (MeSH-NCBI) (2006) http://www.ncbi.nlm.nih.gov/mesh.
NCBI entry Factor B—MeSH-NCBI (MeSH-NCBI) (1999) http://www.ncbi.nlm.nih.gov/mesh.
GLP-1, iHOP-Information Hyperlinked over Proteins (2013).
MCP-1, iHOP-Information Hyperlinked over Proteins (2013).
Kobayashi, et al. "Usefulness of plasma vascular endothelial growth factor in the diagnosis of pancreatic carcinoma: differential diagnosis, tumor progression, and patient survival" Pancreas (2005) 31(1):74-78.
ELISA Kit and Reagent Set (http://genycell.es/images/productos/referencias/dkh0_.pdf) Euroclone Ltd. (2012) pp. 1-27.
Winikoff, et al. "A novel method of pancreatic cancer detection by simultaneous analysis of multiple serum markers" American Society of Clinical Oncology (2004) Gastrointestinal Cancers Symposium, Abs. No. 166, http://www.asco.org.
Grzesiak, et al. "The Integrin-Extracellular Matrix Axis In Pancreatic Cancer" Pancreas (2007) 35, No. 4:293-301.
Grizzle, et al . . . "Abstract 2732: Multiplex Immunoanalysis of Cytokines in EUS-FNAs and in Plasma to Detect Pancreatic Cancer" Cancer Res. (2010) 70(8 Suppl.):Abstract 2732.
Al-Rawi, et al., "Aberrant expression of interleukin-7 (IL-7) and its signalling complex in human breast cancer" Eur. J. Cancer (2004) 40:494-502.
Wenke, et al. "Expression of integrin alpha10 is induced in malignant melanoma" Cellular Oncology (2007) 29:373-386.
Rutkowski, et al., "Cancer and the Complement Cascade" Mol. Cancer Res. (2010) 8:1453-65.
Derin, et al., "Serum levels of apoptosis biomarkers, survivin and TNF-alpha in nonsmall cell lung cancer" Lung Cancer (2007) 59:240-245.
Herman, et al., "Bruton tyrosine kinase represents a promising therapeutic target for treatment of chronic lymphocytic leukemia and is effectively targeted by PCI-32765" Blood (2011) 117:6287-6296.
Lambeck, et al. "Serum Cytokine Profiling as a Diagnostic and Prognostic Tool in Ovarian Cancer: A Potential Role for Interleukin 7" Clin Cancer Res. (2007) 13:2385-2391.
Huang, et al., "A biotin label-based antibody array for high-content profiling of protein expression" Cancer Genomics and Proteomics (2010) 7:129-142.
Budman, et al., "Biomarkers for Detection and Surveillance of Bladder Cancer" CUAJ (2008) 2,3:212-221.
Chu, D., et a. "Identification and screening of individuals at increased risk for pancreatic cancer with emphasis on known environmental and genetic factors and hereditary syndromes" JOP (2010) 11(3):203-12.
Clackson, et al., "Making antibody fragments using phage display libraries" Nature (1991) 352:624-628.
Conlon, K. et al. "Long-term survival after curative resection for pancreatic ductal adenocarcinoma" Clinicopathologic analysis of 5-year survivors. Annals of surgery (1996) 223(3):273-9.
Coussens, L., et al. "Inflammation and cancer" Nature (2002) 420(6917):860-7.
Daugherty, et al., "Antibody affinity maturation using bacterial surface display" Protein Eng, (1998) 11, 9:825-32.
Daugherty, et al., "Development of an optimized expression system for the screening of antibody libraries displayed on the *Escherichia coli* surface" Protein Eng, (1999) 12, 7:613-21.
Dexlin-Mellby, L., et al. "Tissue proteomic profiling of preeclamptic placenta tissue using recombinant antibody microarrays" Proteomics—Clinical Applications (2010) 4(10-11):794-807.
Ducreux, et al., (2015) "Cancer of the pancreas: ESMO Clinical Practice Guidelines for diagnosis, treatment and follow-up" Annals of Oncology, 26 (Supplement 5): v56-v68.

Duffy, M., et al. J. "Tumor markers in pancreatic cancer: a European Group on Tumor Markers (EGTM) status report" Ann Oncol (2010) 21(3):441-7.
Duraker, N., et al. "CEA, CA 19-9, and CA 125 in the differential diagnosis of benign and malignant pancreatic diseases with or without jaundice" Journal of Surgical Oncology (2007) 95(2):142-7.
Eisen, M., et al. "Closter analysis and display of genome-wide expression patterns" Proc Natl Acad Sci USA. (1998) 95: 14863-14868.
Ellmark, P., et al. "Identification of protein expression signatures associated with Helicobacter pylori infection and gastric adenocarcinoma using recombinant antibody microarrays" Mol Cell Proteomics (2006) 5:1638-46.
Johnson, W., et al. "Adjusting batch effects in microarray expression data using empirical Bayes methods" Biostatistics (2007) 8(1):118-27.
Faca, V., et a. "A mouse to human search for plasma proteome changes associated with pancreatic tumor development" PLoS Medicine (2008) 5:e123.
Feldmann, G., et al. "Cyclin-dependent kinase inhibitor Dinaciclib (SCH727965) inhibits pancreatic cancer growth and progression in murine xenograft models" Cancer Biology & Therapy (2011) 12(7):598-609.
Firpo, M., et al. "Improved diagnosis of pancreatic adenocarcinoma using haptoglobin and serum amyloid A in a panel screen" World Journal of Surgery (2009) 33(4):716-22.
FMA (Foundational Model of Anatomy) browser (2019) accessible at http://xiphoid.biostr.washington.edu/fma/index.html.
Fraker, et al., Protein and Cell Membrane Iodinations With a Sparingly Soluble Chloroamide, 1,3,4,6-Tetrachloro-3a,6a-Diphenylglycoluril: Biochem. Biophys. Res. Comm. (1978) 80:849-57.
Freelove, et al. "Pancreatic Cancer: Diagnosis and Management" American Family Physician (2006) 73(3):485-492.
Frick, V. et al. "Enhanced ENA-78 and IL-8 expression in patients with malignant pancreatic diseases" Pancreatology (2008) 8(4-5):488-497.
Fry, L., et al. "Molecular markers of pancreatic cancer: development and clinical relevance" Langenbecks Arch Surg. (2008) 393(6):883-890.
Furukawa, H., et al. "Clinicopathologic features of small pancreatic adenocarcinoma. A collective study". Cancer. (1996) 78(5):986-90.
Gabitass, R., et al. "Elevated myeloid-derived suppressor cells in pancreatic, esophageal and gastric cancer are an independent prognostic factor and are associated with significant elevation of the Th2 cytokine interleukin-13" Cancer Immunology, Immunotherapy: CII. (2011) 60(10):1419-30.
Galasso, D., et al. "Pancreatic cancer: diagnosis and endoscopic staging". Eur Rev Med Pharmacol Sci, (2010) 14(4):375-85.
Gangi, S., et al. Time interval between abnormalities seen on CT and the clinical diagnosis of pancreatic cancer: retrospective review of CT scans obtained before diagnosis AJR (2004) 182:897-903.
Gao, W., et al. "Distinctive serum protein profiles involving abundant proteins in lung cancer patients based upon antibody microarray analysis" BMC Cancer (2005) 5:110.
Gerdtsson, A., et al. "A Multicenter Trial Defining a Serum Protein Signature Associated with Pancreatic Ductal Adenocarcinoma" Int J Proteomics (2015) 2015:587250.
Ghatnekar, O., et al. "Modelling the benefits of early diagnosis of pancreatic cancer using a biomarker signature" International Journal of Cancer Journal International du Cancer (2013) 133(10):2392-7.
Gunneriusson, et al., "Staphylococcal Surface Display of Immunoglobulin A (IgA)- and IgE-Specific In Vitro-Selected Binding Proteins (Affibodies) Based on *Staphylococcus aureus* Protein A": Appl Environ Microbiol (1999) 65, 9:4134-40.
Gupta, S., et al. "Challenges and prospects for biomarker research: a current perspective from the developing world" Biochimica et Biophysica Acta. (2014) 1844(5):899-908.
Haab, B., et al. "Immunoassay and antibody microarray analysis of the HUPO Plasma Proteome Project reference specimens: systematic variation between sample types and calibration of mass spectrometry data" Proteomics (2005) 5(13):3278-91.

(56) References Cited

OTHER PUBLICATIONS

Haab, B., et al., "Protein microarrays for highly parallel detection and quantitation of specific proteins and antibodies in complex solutions" Genome Biology (2001) 2(2):research0004.1-0004.13.

Hanes, et al.,"In vitro selection and evolution of functional proteins by using ribosome display" Proc Natl Acad Sci USA (1997) 94, 10:4937-42.

He, et al., "Antibody-ribosome-mRNA (ARM) complexes as efficient selection particles for in vitro display and evolution of antibody combining sites" Nucleic Acids Res (1997) 25, 24:5132-4.

Hidalgo, M. "Pancreatic cancer" The New England Journal of Medicine (2010) 362(17):1605-17.

Honda K., et al. "Altered plasma apolipoprotein modifications in patients with pancreatic cancer: protein characterization and multi-institutional validation" PLoS One. (2012) 7(10):e46908.

Hou, J., et al. "Estrogen-sensitive PTPRO expression represses hepatocellular carcinoma progression by control of STAT3" Hepatology (2013) 57(2):678-88.

Meyer, et al., "CRAN—Package e1071" (2019) available at http://cran.r-project.org/web/packages/e1071/index.html.

Huang, Y., et al. "PTPRO promoter methylation is predictive of poorer outcome for HER2-positive breast cancer: indication for personalized therapy" Journal of Translational Medicine (2013)11:245.

Huston, et al., "Protein engineering of antibody binding sites: Recovery of specific activity in an anti-digoxin single-chain Fv analogue produced in *Escherichia coli*" Proc. Natl. Acad. Sci. USA (1988) 85:5879-83.

Ihaka, et al. "R: A language for data analysis and graphics" J. Comp. Graph. Stat. (1996) 5:299-314.

Ingvarsson, J., et al. "Design of recombinant antibody microarrays for serum protein profiling: targeting of complement proteins" Journal of Proteome Research (2007) 6:3527-36.

Ishikawa, O., et al. "Minute carcinoma of the pancreas measuring 1 cm or less in diameter—collective review of Japanese case reports" Hepato-gastroenterology (1999) 46:8-15.

Itakura, J., et al. "Enhanced expression of vascular endothelial growth factor in human pancreatic cancer correlates with local disease progression" Clinical Cancer Research: An Official Journal of the American Association for Cancer Research (1997) 3(8):1309-16.

Jemal, A., et al. "Cancer statistics" CA Cancer J Clin (2009)59:225-49.

Jenkins, R., et al., "Arrays for protein expression profiling: Towards a viable alternative to two-dimensional gel electrophoresis?" Proteomics, (2001) 1:13-29.

Jiang, J., et al. (2004) "Serum level of TSGF, CA242 and CA19-9 in pancreatic cancer" World Journal of Gastroenterology : WJG 10(11):1675-7.

Jimenez-Vidal, M., et al. "Nuclear-localized calcineurin homologous protein CHP1 interacts with upstream binding factor and inhibits ribosomal RNA synthesis" The Journal of Biological Chemistry (2010) 285(47):36260-6.

Jin, Q., et al. "Overexpression of CHP2 enhances tumour cell growth, invasion and metastasis in ovarian cancer" In vivo (2007) 21(4):593-8.

Siegel, R., et al. (2012) "Cancer Statistics (2012)" CA: a cancer journal for clinicians 62(1):10-29.

Skerra, et al. "Assembly of a Functional Immunoglobulin Fv Fragment in *Escherichia coli*" Science (1988) 240:1038-41.

Smith, D. "Filamentous Fusion Phage: Novel Expression Vectors That Display Cloned Antigens on the Virion Surface" Science (1985) 228:1315-7.

Soderlind, E., et al. "Recombining germline-derived CDR sequences for creating diverse single-framework antibody libraries". Nat Biotechnol. (2000) 18(8):852-856.

Sohn, T., et al. "Resected adenocarcinoma of the pancreas-616 patients: results, outcomes, and prognostic indicators" Journal of Gastrointestinal Surgery : Official Journal of the Society for Surgery of the Alimentary Tract. (2000) 4(6):567-79.

Song, M., et al. The deubiquitinylation and localization of PTEN are regulated by a HAUSP-PML network. Nature. (2008) 455(7214):813-7.

Steinhauer, C., et al. "Single framework recombinant antibody fragments designed for protein chip applications" BioTechniques Suppl (2002) 33:S38-S45.

Steinhauer, et al., "Biocompatibility of surfaces for antibody microarrays: design of macroporous silicon substrates" Anal Biochem (2005) 341:204-13.

Stoevesandt O., et al. "European and international collaboration in affinity proteomics" New biotechnology. (2012) 29(5):511-4.

Surinova, S., et al. "On the development of plasma protein biomarkers. Journal of proteome research" (2011) 10(1):5-16.

Ungefroren, H., et al. "Immunological escape mechanisms in pancreatic carcinoma" Ann N Y Acad Sci (1999) 880:243-51.

Van De Vijver, et al., "A Gene-Expression Signature as a Predictor of Survival in Breast Cancer" N. Eng. J. Med (2002) 347:1999-2009.

Ward, et al., "Binding activities of a repertoire of single immunoglobulin variable domains secreted from *Escherichia coli*" Nature (1989) 341:544-6.

Warshaw, A., et al. "Pancreatic carcinoma" N Engl J Med (1992) 326(7):455-65.

Watanabe, I., et al. "Onset symptoms and tumour locations as prognostic factors of pancreatic cancer" Pancreas. (2004) 28(2):160-5.

Wigmore, S., et al. "Cytokine regulation of constitutive production of interleukin-8 and -6 by human pancreatic cancer cell lines and serum cytokine concentrations in patients with pancreatic cancer" Int J Oncol. (2002) 21(4):881-886.

Wingren, C., et al. "Antibody microarray analysis of directly labelled complex proteomes" Current Opinion in Biotechnology (2008) 19(1):55-61.

Wingren C., et al. "Design of recombinant antibody microarrays for complex proteome analysis: choice of sample labeling-tag and solid support" (2007) Proteomics 7(17):3055-65.

Wingren, C., et al. "Identification of serum biomarker signatures associated with pancreatic cancer" Cancer Research (2012) 72(10):2481-90.

Wingren, C., et al. "Microarrays based on affinity-tagged single-chain Fv antibodies: sensitive detection of analyte in complex proteomes" Proteomics (2005) 5(5):1281-91.

Wingren, et al., "High-throughput proteomics using antibody microarray" Exp. Rev. Proteomics (2004) 1:355-364.

Wingren, C., et al. "Antibody Microarrays: Current Status and Key Technological Advances" OMICS (2006) 3:411-427.

Winter, et al. "Man-made Antibodies" Nature, (1991) 349:293-299.

Winter, J., et la. "A novel survival-based tissue microarray of pancreatic cancer validates MUC1 and mesothelin as biomarkers" PLoS One (2012) 7, e40157.

Wu, T., et al. "Surgical effect of malignant tumour of body and tail of the pancreas: compare with pancreatic head cancer" Zhonghua wai ke za zhi [Chinese journal of surgery] (2007) 45(1):30-3 [Abstract Only].

Wu, Y., et al. "The impact of centering first-level predictors on individual and contextual effects in multilevel data analysis" Nursing Research (2005) 54(3):212-6.

Xia, C., et al. "GGAPs, a new family of bifunctional GTP-binding and GTPase-activating proteins" Molecular and Cellular Biology (2003) 23(7):2476-88.

Yachida, S., et al. "Distant metastasis occurs late during the genetic evolution of pancreatic cancer" Nature (2010) 467(7319):1114-7.

Yeo, et al., "Epidemiology and Risk Factors" Curr. Probl. Cancer (2002) 26:176-275.

Yu, K., et al. "Characterization of proteins in human pancreatic cancer serum using differential gel electrophoresis and tandem mass spectrometry" J Proteome Res., (2005) 4(5):1742-1751.

Zhang, H., et al. "Mass spectrometric detection of tissue proteins in plasma" Molecular & cellular proteomics : MCP (2007) 6(1):64-7.

Zhao, G., et al. "USP7 overexpression predicts a poor prognosis in lung squamous cell carcinoma and large cell carcinoma" Tumour Biol. (2015) 36:1721-1729.

(56) References Cited

OTHER PUBLICATIONS

American Cancer Society, "Pancreatic Cancer Stages" (2017) available at http://www.cancer.org/cancer/pancreaticcancer/detailedguide/pancreatic-cancer-staging.
Edge, et al., AJCC Cancer Staging Manual (7th ed.) (2011) Springer, New York.
Hanada, K., et al. "Effective screening for early diagnosis of pancreatic cancer" Best Pract Res Clin Gastroenterol. (2015) 29(6):929-939.
Chari, S., et al."Early detection of sporadic pancreatic cancer: summative review" Pancreas (2015) 44(5):693-712.
Brentnall, T. "Progress in the Earlier Detection of Pancreatic Cancer" J Clin Oncol. (2016) 34(17):1973-4.
Lewis, et al. "Pancreatic cancer: Are "liquid biopsies" ready for prime-time?" World J Gastroenterol. (2016) 22(32):7175-7185.
Thota, et al., "Treatment of Metastatic Pancreatic Adenocarcinoma: A Review" (2014) Oncology 28(1):70-4.
Torre, L., et al. "Global cancer statistics, 2012" CA Cancer J Clin. (2015) 65(2):87-108.
Kamisawa,T. et al. "Pancreatic cancer" Lancet. (2016) 388(10039):73-85.
Okano, K., et al. "Strategies for early detection of resectable pancreatic cancer" World J Gastroenterol (2014) 20(32):11230-40.
Ryan, D., et al. "Pancreatic adenocarcinoma" N Engl J Med. (2014) 371(22):2140-1.
Zhang, H., et al. "Systematic review and meta-analysis of minimally invasive versus open approach for pancreaticoduodenectomy" Surg Endosc. (2016) 30(12):5173-84.
Matsuno, S., et al. "Pancreatic Cancer Registry in Japan: 20 years of experience". Pancreas (2004) 28(3):219-30.
Vasen, H., et al. "Benefit of Surveillance for Pancreatic Cancer in High-Risk Individuals: Outcome of Long-Term Prospective Follow-Up Studies From Three European Expert Centers" J Clin Oncol. (2016) 34(17):2010-9.
Kenan, et al., "In Vitro Selection of Aptamers from RNA Libraries" Methods Mol Biol (1999)118:217-31.
Kieke, et al., "Selection of functional T cell receptor mutants from a yeast surface-display library" Proc Natl Acad Sci USA (1999) 96,10:5651-6.
Konstantinou, F., et al. (2013) "Pancreatic cancer: what about screening and detection" JOP : Journal of the Pancreas 14(4):312-5.
Koopmann, J., et al. "Serum markers in patients with resectable pancreatic adenocarcinoma: macrophage inhibitory cytokine 1 versus CA19-9" Clinical Cancer Research: An Official Journal of the American Association for Cancer Research (2006) 12:442-6.
Kudo-Saito, C., et al. "CCL2 is critical for immunosuppression to promote cancer metastasis" Clinical & Experimental Metastasis (2013) 30(4):393-405.
Lal, et al., "Antibody arrays: an embryonic but rapidly growing technology" Drug Discov Today (2002)15;7 (18 Suppl):S143-9).
Lau, M., et al. (2010) "Incidence and survival of pancreatic head and body and tail Cancers: a population-based study in the United States" Pancreas 39(4):458-62.
Ling, Q., et al. "The diversity between pancreatic head and body/tail cancers: clinical parameters and in vitro models" Hepatobiliary & Pancreatic Diseases International: HBPD INT. (2013) 12(5):480-7.
Locker, G., et al. "ASCO 2006 update of recommendations for the use of tumor markers in gastrointestinal cancer" Journal of Clinical Oncology: Official Journal of the American Society of Clinical Oncology (2006) 24:5313-27.
Ma, Y., et al. (2013) "Dynamic mast cell-stromal cell interactions promote growth of pancreatic cancer" Cancer Research 73(13):3927-37.
Malvezzi, M., et al. "European cancer mortality predictions for the year" Annals of oncology (2014) 25(8):1650-6.
Marks, et al., "By-passing Immunization Human Antibodies from V-gene Libraries Displayed on Phage" J Mol Biol (1991) 222:581-97.

McDade, T., et al. "Salicylates inhibit NF-kappaB activation and enhance TNF-alpha-induced apoptosis in human pancreatic cancer cells" The Journal of Surgical Research (1999) 83(1): 56-61.
McShane, L., et al. "Reporting recommendations for tumor MARKer prognostic studies (REMARK)". Nat Clin Pract Oncol (2005) 2:416-22.
Melo, S., et al. (2015) "Glypican-1 identifies cancer exosomes and detects early pancreatic cancer" Nature 523: 177-182.
Miller, J., et al. "Antibody microarray profiling of human prostate cancer sera: antibody screening and identification of potential biomarkers" Proteomics (2003) 3(1):56-63.
Mor, G., et al., "Serum protein markers for early detection of ovarian cancer" Proc. Natl. Acad. Sci (2005) 102, 7677-7682.
Morrison, et al., "Chimeric human antibody molecules: mouse antigen-binding domains with human constant region domains" Proc. Natl. Acad. Sci. USA, (1984) 81:6851-6855.
Motiwala, T., et al. "Protein tyrosine phosphatase receptor-type O (PTPRO) exhibits characteristics of a candidate tumour suppressor in human lung cancer" Proceedings of the National Academy of Sciences of the United States of America (2004) 101(38):13844-9.
Nakano M., et al. "Site-specific analysis of N-glycans on haptoglobin in sera of patients with pancreatic cancer: a novel approach for the development of tumor markers" Int J Cancer. (2008) 122(10):2301-2309.
Nemoto, et al., "In vitro virus: Bonding of mRNA bearing puromycin at the 3'-terminal end to the C-terminal end of its encoded protein on the ribosome in vitro" Febs lett, (1997) 414(2):405-8.
Ni, X., et al. "The clinical value of serum CEA, CA19-9, and CA242 in the diagnosis and prognosis of pancreatic cancer" European Journal of Surgical Oncology: The Journal of the European Society of Surgical Oncology and the British Association of Surgical Oncology (2005) 31:164-9.
Olsson, N., et al. "Epitope-specificity of recombinant antibodies reveals promiscuous peptide-binding properties" Protein Science: A Publication of the Protein Society (2012) 21(12):1897-910.
Orchekowski, R., et al. "Antibody microarray profiling reveals individual and combined serum proteins associated with pancreatic cancer" Cancer Research (2005) 65:11193-202.
Pannala, R., et al. "New-onset diabetes: a potential clue to the early diagnosis of pancreatic cancer" The Lancet Oncology (2009) 10(1):88-95.
Parker, L., et al. "Clinical validity of detecting K-ras mutations for the diagnosis of exocrine pancreatic cancer: a prospective study in a clinically-relevant spectrum of patients" European Journal of Epidemiology (2011) 26(3):229-36.
Pauly, F., et al. "Identification of B-cell lymphoma subsets by plasma protein profiling using recombinant antibody microarrays" Leukemia Res. (2014) 38:682-690.
Pavlickova, P., et al. "Advances in recombinant antibody microarrays" Clin. Chim. Acta. (2004) 342:17-35.
Pawlak, M., et al. "Zeptosens' protein microarrays: A novel high performance microarray platform for low abundance protein analysis" Proteomics (2002) 2:383-393.
Pelaez-Luna, M., et al. Resectability of presymptomatic pancreatic cancer and its relationship to onset of diabetes: a retrospective review of CT scans and fasting glucose values prior to diagnosis The American Journal of Gastroenterology (2007) 102(10):2157-63.
Poch, B., et al. "Systemic immune dysfunction in pancreatic cancer patients" Langenbecks Arch Surg. (2007) 392(3):353-358.
Porta, M., et al. "Validity of the hospital discharge diagnosis in epidemiologic studies of biliopancreatic pathology" Pankras II Study Group. European Journal of Epidemiology (2000) 16(6):533-41.
Porta, M., et al. "Exocrine pancreatic cancer: symptoms at presentation and their relation to tumour site and stage" Clinical & Translational Oncology (2005) 7(5):189-97.
Porta, M., et al. "Serum concentrations of organochlorine compounds and K-ras mutations in exocrine pancreatic cancer" PANKRAS II Study Group. Lancet. (1999) 354(9196):2125-9.
Quackenbush, J. "Computational analysis of microarray data" Nature reviews Genetics (2001) 2(6):418-27.

(56) References Cited

OTHER PUBLICATIONS

Rahib, L., et al. "Projecting cancer incidence and deaths to 2030: the unexpected burden of thyroid, liver, and pancreas cancers in the United States" Cancer Research (2014) 74(11):2913-21.
Rastogi, T., et al. "Opportunities for cancer epidemiology in developing countries" Nature reviews Cancer (2004) 4(11):909-17.
Rosenwald, A.,et al. "The proliferation gene expression signature is a quantitative integrator of oncogenic events that predicts survival in mantle cell lymphoma" Cancer Cell (2003) 3, 185-197.
Rosse, et al. "A reference ontology for biomedical informatics: the Foundational Model of Anatomy" J. Biomed. Informatics (2003) 36(6):478-500.
Rustgi, A., et al. "Pancreatic cancer: novel approaches to diagnosis and therapy" Gastroenterology (2005) 129(4):1344-7.
Sanchez-Carbayo, M., et al., "Profiling Bladder Cancer Using Targeted Antibody Arrays" (2006) Am. J. Pathol. 168:93-103.
Sandstrom A., et al. "Serum proteome profiling of pancreatitis using recombinant antibody microarrays reveals disease-associated biomarker signatures" Proteomics Clinical Applications (2012) 6(9-10):486-96.
Santi, et al., "Bacteriophage Lambda Display of Complex cDNA Libraries: A New Approach to Functional Genomics" J Mol Biol, (2000) 296:497-508.
Schaler, et al. "Antibody Array Profiling Reveals Serum TSP-1 as a Marker to Distinguish Benign From Malignant Prostatic Disease" The Prostate (2007) 67:255-267.
Schervish, M., "A Review of Multivariate Analysis" Statistical Science (1987) 2(4):396-413.
Schmitz-Winnenthal, F., et al. "High frequencies of functional tumor-reactive T cells in bone marrow and blood of pancreatic cancer patients" Cancer Res. (2005) 65(21):10079-87.
Shaib, Y., et al. "The epidemiology of pancreatic cancer in the United States: changes below the surface" Alimentary Pharmacology & Therapeutics (2006) 24(1):87-94.
Shaw, V., et al. "Serum cytokine biomarker panels for discriminating pancreatic cancer from benign pancreatic disease" Molecular Cancer (2014) 13:114.
Shimizu, Y., et al. "Small carcinoma of the pancreas is curable: new computed tomography finding, pathological study and postoperative results from a single institute" Journal of Gastroenterology and Hepatology (2005) 20(10):1591-4.
Shusta, et al., "Yeast Polypeptide Fusion Surface Display Levels Predict Thermal Stability and Soluble Secretion Efficiency" J Mol Biol, (1999) 292(5):949-56.
Paul, W.E., Fundamental Immunology, 3rd edition, Raven Press, New York (1993) pp. 292-295.
Bendig, M.M. "Humanization of Rodent Monoclonal Antibodies by CDR Grafting" Methods: A Companion to Methods in Enzymology (1995) 8:83-93.
Layton, et al., "Syk Tyrosine Kinase Acts as a Pancreatic Adenocarcinoma Tumor Suppressor by Regulating Cellular Growth and Invasion" The American Journal of Pathology (2009) 175,6:2625-2636.
Ludwig, et al., "Biomarkers in Cancer Staging, Prognosis, and Treatment Selection" Nature Reviews: Cancer (2005)5:845-856.
Mettlin, et al. "Relative Sensitivity and Specificity of Serum Prostate Specific Antigen (PSA) Level Compared with Age-Referenced PSA, PSA Density, and PSA Change" Cancer (1994) 74,5:1615-1620.
Brawer, et al. "Measurement of Complexed PSA Improves Specificity for Early Detection of Prostate Cancer" Urology (1998) 52,3: 372-378.
Cho, et al. "WI412 Expression of Sox-11 and Sox-4 is involved in pathogenesis of solid pseudopapillary tumor in pancreas" Gastroenterology (2008) 134, 4:A-699.
Imai, et al. Database WPI Week 201518 Thomson Scientific, London, GB for JP 2015.033381 (2015).
Xiang-Yi, et al. "Advances in pancreatic cancer research: Moving towards early detection" World Journal of Gastroenterology (2014) 20, 32 :11241.
Le, et al. "Prognostic and predictive markers in pancreatic adenocarcinoma, Digestive and Liver Disease" (2015) 48, 3:223-230.
Yu, et al. "Expression profiling during mammary epithelial cell three-dimensional morphogenesis and ErbB2-mediated transformation" Molecular and Cellular Biology (2012) 32, 19:3913-3924.
The Human Protein Atlas, "Expression of PTPRO in cancer—Summary" (2015) available at http://www.proteinatlas.brb/ENSG00000151490-PTPROIcancer.
Carlsson, et al. "Antibody Microarray Based Oncoproteomics—Analysis of Breast Cancer Proteomes" Presented at 29th Annual San Antonio Breast Cancer Symposium (2006) Poster #1002.
Perez-Galan, et al. "The proteasome inhibitor bortezomib induces apoptosis in mantle-cell lymphoma through generation of ROS and Noxa activation independent of p53 status" Blood (2006) 107:257-264.
Gerdtsson, et al. "Plasma protein profiling in a stage defined pancreatic cancer cohort—Implications for early diagnosis" Molecular Oncology (2016) 10, 8:1306-1316.
Duffy, et al. "The Gap Junction Protein Connexin32 Interacts with the Src Homology 3/Hook Domain of Discs Large Homolog 1" Journal of Biological Chemistry (2007) 282, 13: 9789-9796.
Veronique, M, et al. "Global gene expression profiling in human lung cells exposed to cobalt" BMC Genomics (2007) 8:147.
Quantikine Elisa—Human VEGF Immunoassay-Package Insert, Cat. No. DVE00, SVE00, PDVE00, R&D Systems Inc. 2019.
Hornbeck, et al. "Enzyme-Linked Immunosorbent Assays (ELISA)" Current Protocols in Molecular Biology (1991) 11.2.1-11.2.22.
Barak, et al. "Serum inflammatory cytokines, complement components, and soluble interleukin 2 receptor in primary biliary cirrhosis" J Autoimmun (2009) 33(3-4):178-82.
Chen, et al. "The relationship between CD4-CD8-T cells in the peripheral blood of patients with pancreatic carcinoma and IL-4, IFN-gamma levels" Chinese Journal of Surgery (2009) 47,13:995-998, [Abstract only].
Suemizu, et al. "Identification of a key molecular regulator of liver metastasis in human pancreatic carcinoma using a novel quantitative model of metastasis in NOD/SCID/ycnull (NOG) mice", Intl. J. Oncol. (2007) 31:741-751.
Okada, et al. "Elevated Serum Interleukin-6 Levels in Patients with Pancreatic Cancer", Japanese Journal of Clinical Oncology (1998) 28, 1:12-15.
Kannagi, et al. "Quantitative and Qualitative Characterization of Human Cancer-associated Serum Glycoprotein Antigens Expressing Fucosyl or Sialyl-Fucosyl Type 2 Chain Polylactosamine", Cancer Research (1986) 46:2619-2626.
Alonzo, et al. "Sample size calculations for comparative studies of medical tests for detecting presence of disease" Statistics in Medicine (2002) 21(6):835-52.
Anderson, N., et al. "The human plasma proteome: history, character, and diagnostic prospects". Molecular & Cellular Proteomics: MCP (2002) 1(11):845-67.
Arlt, A., et al. "Targeting apoptosis pathways in pancreatic cancer" Cancer letters (2013) 332(2):346-58.
Bauden, M., et al. "Circulating nucleosomes as epigenetic biomarkers in pancreatic cancer" Clin Epigenet (2015) 7:106.
Bellone, et al., "Tumor-Associated Transforming Growth Factor-b and Interleukin-10 Contribute to a Systemic Th2 Immune Phenotype in Pancreatic Carcinoma Patients" Am J Pathol (1999) 155(2):537-47.
Bellone, G., et al. "Cytokine expression profile in human pancreatic carcinoma cells and in surgical specimens: implications for survival" Cancer Immunology, Immunotherapy (2006) 55(6):684-98.
Better, et al. "*Escherichia coli* Secretion of an Active Chimeric Antibody Fragment" Science (1988) 240:1041-3.
Biankin, A., et al. "Molecular pathogenesis of precursor lesions of pancreatic ductal adenocarcinoma" Pathology, (2003) 35(1):14-24.
Bird, et al., "Single-Chain Antigen-Binding Proteins" Science (1988) 242:423-6.
Boeck, S., et al. "Prognostic and therapeutic significance of carbohydrate antigen 19-9 as tumor marker in patients with pancreatic cancer" Oncology (2006) 70(4):255-264.

(56) References Cited

OTHER PUBLICATIONS

Borrebaeck, C., et al. "Design of high-density antibody microarrays for disease proteomics: key technological issues" Journal of Proteomics (2009) 72(6):928-35.
Borrebaeck, C., et al. "High-throughput proteomics using antibody microarrays: an update" Expert Rev Mol Diagn (2007) 7:673-86.
Borrebaeck, C. "Antibody Microarray-based Oncoproteomics" Expert Opin. Biol. Ther (2006) 6(8):833-8.
Brand, R., et al. "Serum biomarker panels for the detection of pancreatic cancer" Clinical Cancer Research: An Official Journal of the American Association for Cancer Research (2011) 17(4):805-16.
Bunger, S., et al. "Serum biomarkers for improved diagnostic of pancreatic cancer: a current overview" Journal of Cancer Research and Clinical Oncology (2011) 137(3):375-89.
Burges, et al., "A Tutorial on Support Vector Machines for Pattern Recognition" Data Mining and Knowledge Discovery (1998) 2:121-167.
Carlsson, A., et al. "Plasma proteome profiling reveals. biomarker patterns associated with prognosis and therapy selection in glioblastoma multiforme patients" Proteomics Clinical applications (2010) 4(6-7): 591-602.
Carlsson, A., et al. "Serum proteome profiling of metastatic breast cancer using recombinant antibody microarrays" Eur J Cancer. (2008) 44(3):472-80.
Carlsson, A., et al. "Molecular serum portraits in patients with primary breast cancer predict the development of distant metastases" Proceedings of the National Academy of Sciences of the United States of America (2011) 108(34):14252-7.
Carlsson, A., et al. "Serum protein profiling of systemic lupus erythematosus and systemic sclerosis using recombinant antibody microarrays" Molecular & cellular proteomics (2011) 10(5):M110 005033.
Chang, S., et al. "Identification of a biomarker panel using a multiplex proximity ligation assay improves accuracy of pancreatic cancer diagnosis" J Transl Med., (2009) 7:105.

Chechlinska, M., et al. "Systemic inflammation as a confounding factor in cancer biomarker discovery and validation" Nat Rev Cancer (2010) 10(1):2-3.
Chen, J., et al. "Expression and clinical significance of complement C3, complement C4b1 and apolipoprotein E in pancreatic cancer" Oncology letters (2013) 6(1):43-8.
Chen, R., et al. "Comparison of pancreas juice proteins from cancer versus pancreatitis using quantitative proteomic analysis" Pancreas (2007) 34(1):70-79.
Chen, R., et al. "Proteomics studies of pancreatic cancer" Proteomics Clin Appl (2007) 1(12):1582-1591.
Chang, et al. "LIBSVM: a library for support vector machines" (2018) available at http://www.csie.ntu.edu.tw/~cjlin/libsvm.
Nolen, et al., "Prediagnostic Serum Biomarkers as Early Detection Tools for Pancreatic Cancer in a Large Prospective Cohort Study" PLoS ONE (2014) 9(4): e94928.
Peng, et al., "Predictive proteomic signatures for response of pancreatic cancer patients receiving chemotherapy" Clin. Proteom. (2019) 16:31.
Peng, et al., "Systemic Proteome Alterations Linked to Early Stage Pancreatic Cancer in Diabetic Patients" Cancers (2020) 12:1534.
Lee, et al., "Identification of Human Complement Factor B as a Novel Biomarker Candidate for Pancreatic Ductal Adenocarcinoma" J. Proteome Res. (2014) 13:4878-4888.
Artinyan, et al., "The anatomic location of pancreatic cancer is a prognostic factor for survival" HPB (2008) 10:371-376.
Diaz-Rodriguez, et al., "Hec1 overexpression hyperactivates the mitotic checkpoint and induces tumor formation in vivo" PNAS (2008) 105(43):16719-16724.
Gerdtsson, et al., "Plasma protein profiling in a stage defined pancreatic cancer cohort—Implications for early diagnosis" Mol. Oncol. (2016) 10:1305-1316.
Imai, et al., "Development of diagnostic method for intractable breast cancer and pancreatic cancer using new biomarker PRDM14" (2014) available at https://app.dimensions.ai/details/grant/grant.9493967.

* cited by examiner

METHODS, ARRAYS AND USES THEREOF

This application claims priority to UK patent application No. GB2010970.8, filed Jul. 16, 2020. The entire disclosure of the foregoing application is incorporated by reference herein.

Incorporated herein by reference in its entirety is the Sequence Listing being concurrently submitted via EFS-Web as a text file named Seqlist.txt, created Jul. 15, 2021, and having a size of 90,139 bytes.

FIELD OF INVENTION

The present invention provides in vitro methods for determining a pancreatic cancer-associated disease state (such as pancreatic cancer presence or risk of pancreatic cancer), as well as arrays and kits for use in such methods.

BACKGROUND

Pancreatic cancer is a relatively rare but highly lethal cancer with a 5-year survival rate of less than 10% (Ilic and Ilic, 2016). Its high mortality makes it the third leading cause of cancer-related death in the United States (Rawla et al., 2019). One factor behind this dismal record is the lack of early and disease specific clinical symptoms. At the time of diagnosis, patients have often developed late-stage disease and only approximately 15-20% of the patients have resectable tumors (Conlon et al., 1996; Sohn et al., 2000). Significantly better outcomes have been reported for smaller tumors detected at an earlier stage. A 5-year survival rate of 30% to 60% in tumors less than 20 mm in size and even exceeding 75% in tumors less than 10 mm have been reported (Shimizu et al., 2005, Kenner et al., 2016).

Pancreatic ductal adenocarcinoma (PDAC) is the most common type of pancreatic cancer accounting for more than 90% of all pancreatic malignancies (McGuigan et al., 2018). Rapid tumor progression, early metastasis, and resistance to conventional chemotherapies are hallmarks of PDAC (Orth et al., 2019). Since complete surgical removal is the only potentially curative treatment for PDAC, biomarkers for early detection are urgently needed. The most evaluated biomarker for PDAC, CA19-9, suffers from inadequate specificity and sensitivity with elevated levels in several benign diseases (e.g. chronic pancreatitis and obstructive jaundice), as well as a complete absence in patients that are Lewis blood type negative (about 5-10% of the population). Consequently, the use of serum CA19-9 by itself is not recommended for screening, but can provide important information concerning prognosis, response to chemotherapy as well as predict post-operative recurrence (Ballehaninna and Chamberlain, 2011).

Taken together, there remains a need for improved methods of diagnosing pancreatic cancers such as PDAC, particularly in the early stages of the disease and it has been postulated that earlier diagnosis would result in increased survival for patients with PDAC and that selected high-risk groups could benefit greatly from a non-invasive test for detecting cancer development.

SUMMARY OF THE INVENTION

Accordingly, a first aspect of the invention provides a method for diagnosing or determining a pancreatic cancer-associated disease state comprising or consisting of the steps of:
(a) providing a sample from an individual to be tested; and
(b) determining a biomarker signature of the test sample by measuring the presence and/or amount in the test sample of one or more biomarkers selected from the group defined in Table A;
wherein the presence and/or amount in the test sample of the one or more biomarkers selected from the group defined in Table A is indicative of the pancreatic cancer-associated disease state in the individual.

In a preferred embodiment, step (b) comprises determining a biomarker signature of the test sample measuring the presence and/or amount in the test sample of two or more biomarkers selected from the group defined in Table A, wherein the presence and/or amount in the test sample of the two or more biomarkers selected from the group defined in Table A is indicative of the pancreatic cancer-associated disease state in the individual.

In an additional or alternative embodiment, step (b) comprises determining a biomarker signature of the test sample measuring the presence and/or amount in the test sample of two or more biomarkers selected from the group defined in Table A(i)-(vi), wherein the presence and/or amount in the test sample of the two or more biomarkers selected from the group defined in Table A(i)-(vi) is indicative of the pancreatic cancer-associated disease state in the individual.

TABLE A

| Biomarkers (and associated Uniprot IDs where available) |
| --- |
| Part (i) |
| OPG (O00300)/VWF (P04275) |
| Part (ii) |
| GSN (P06396)/HADH2 (Q99714) |
| Part (iii) |
| IGFBP3 (P17936) |
| Part (iv) |
| Complement Factor B (P00751) |
| Part (v) |
| MUC16 (CA125) (Q8WXI7)/FCN2 (Q15485)/MASP2 (O00187) |
| Part (vi) |
| Complement C4 (P0C0L4/5) Complement C5 (P01031) Cystatin C (P01034) |
| Part (vii) |
| Carbohydrate Antigen 19-9 (CA19-9) |

Thus, in one embodiment, the method comprises determining a biomarker signature of the test sample, which enables a diagnosis to be reached in respect of the individual from which the sample is obtained.

By "pancreatic cancer associated disease state" we include pancreatic cancer presence per se and the risk of having or of developing pancreatic cancer. In particular, we include the presence of pancreatic ductal adenocarcinoma (PDAC) at various stages.

In specific embodiments, the methods of the invention permit:
(i) diagnosis of early pancreatic cancer; and/or
(ii) diagnosis of pancreatic cancer (i.e. early or late).

By "biomarker" we include any naturally occurring biological molecule, or component or fragment thereof, the measurement of which can provide information useful in the diagnosis of pancreatic cancer. Thus, in the context of Table A, the biomarker may be the protein, or a polypeptide fragment or carbohydrate moiety thereof. Alternatively, the biomarker may be a nucleic acid molecule, such as a mRNA, cDNA or circulating tumour DNA molecule, which encodes the protein or part thereof.

By "diagnosis" we include determining the presence or absence of a disease state in an individual (e.g., determining whether an individual is or is not suffering from early stage pancreatic cancer or late stage pancreatic cancer).

By "early pancreatic cancer" we include or mean pancreatic cancer comprising or consisting of stage I and/or stage II pancreatic cancer.

The methods of the invention are suitable for testing a sample from any individual who is suspected of having, or at risk of developing, a pancreatic cancer-associated disease state. For example, the individual may be from one of the following groups with an elevated risk of having or developing pancreatic cancer:
(i) Individuals with a family history of pancreatic cancer or certain hereditary predispositions (e.g. Peutz-Jeghers syndrome);
(ii) Individuals diagnosed with diabetes, e.g. new-onset diabetes (e.g. type II), especially those aged 50 years or over; and/or
(iii) Individuals with symptoms suggestive or consistent with pancreatic cancer, e.g. pain in the upper abdomen or upper back, loss of appetite, weight loss, jaundice (yellow skin and eyes, and dark urine), indigestion, nausea, vomiting and/or extreme tiredness (fatigue)).

The individual may also be an individual with a benign pancreatic or biliary disease, e.g. acute and chronic pancreatitis, diabetes, liver disease, pancreatic cyst, gallstone disease and IgG4 disease.

In an additional or alternative embodiment the method is suitable for distinguishing an individual with a pancreatic cancer-associated disease state from an individual without pancreatic cancer but with symptoms suggestive or consistent with pancreatic cancer. For example, the individual without pancreatic cancer from which an individual with a pancreatic cancer-associated disease state may be distinguished may have a benign pancreatic or biliary disease, e.g. acute and chronic pancreatitis, diabetes, liver disease, pancreatic cyst, gallstone disease and IgG4 disease.

Thus, in one embodiment, the methods of the invention provide a qualitative result for the detection of pancreatic abnormalities in individuals with increased risk of developing PDAC.

In a specific embodiment, the methods of the invention permit:
(a) the diagnosis of early pancreatic cancer; and
(b) the diagnosis of late pancreatic cancer.

Advantageously, the methods of the invention also enable the differentiation between pancreatic cancer and chronic pancreatitis in an individual.

By "early pancreatic cancer" (or "early stage pancreatic cancer") we include or mean pancreatic cancer comprising or consisting of stage I and/or stage II pancreatic cancer, for example as determined by the American Joint Committee on Cancer (AJCC) TNM system (e.g., see: cancer.org/cancer/pancreaticcancer/detailedguide/pancreatic-cancer-staging and AJCC Cancer Staging Manual ($7^{th}$ ed.), 2011, Edge et al., Springer which are incorporated by reference herein).

The TNM cancer staging system is based on 3 key pieces of information:
T describes the size of the main (primary) tumour and whether it has grown outside the pancreas and into nearby organs.
N describes the spread to nearby (regional) lymph nodes.
M indicates whether the cancer has metastasized (spread) to other organs of the body. (The most common sites of pancreatic cancer spread are the liver, lungs, and the peritoneum—the space around the digestive organs.)

Numbers or letters appear after T, N, and M to provide more details about each of these factors.
T categories
TX: The main tumour cannot be assessed.
T0: No evidence of a primary tumour.
Tis: Carcinoma in situ (the tumour is confined to the top layers of pancreatic duct cells). (Very few pancreatic tumours are found at this stage.)
T1: The cancer is still within the pancreas and is 2 centimetres (cm) (about ¾ inch) or less across.
T2: The cancer is still within the pancreas but is larger than 2 cm across.
T3: The cancer has grown outside the pancreas into nearby surrounding tissues but not into major blood vessels or nerves.
T4: The cancer has grown beyond the pancreas into nearby large blood vessels or nerves.
N Categories
NX: Nearby (regional) lymph nodes cannot be assessed.
N0: The cancer has not spread to nearby lymph nodes.
N1: The cancer has spread to nearby lymph nodes.
M Categories
M0: The cancer has not spread to distant lymph nodes (other than those near the pancreas) or to distant organs such as the liver, lungs, brain, etc.
M1: The cancer has spread to distant lymph nodes or to distant organs.

Once the T, N, and M categories have been determined, this information is combined to assign an overall stage of 0, I, II, III, or IV (sometimes followed by a letter). This process is called stage grouping.

Stage 0 (Tis, N0, M0): The tumour is confined to the top layers of pancreatic duct cells and has not invaded deeper tissues. It has not spread outside of the pancreas. These tumours are sometimes referred to as pancreatic carcinoma in situ.

Stage IA (T1, N0, M0): The tumour is confined to the pancreas and is 2 cm across or smaller (T1). It has not spread to nearby lymph nodes (N0) or distant sites (M0).

Stage IB (T2, N0, M0): The tumour is confined to the pancreas and is larger than 2 cm across (T2). It has not spread to nearby lymph nodes (N0) or distant sites (M0).

Stage IIA (T3, N0, M0): The tumour is growing outside the pancreas but not into major blood vessels or nerves (T3). It has not spread to nearby lymph nodes (N0) or distant sites (M0).

Stage IIB (T1-3, N1, M0): The tumour is either confined to the pancreas or growing outside the pancreas but not into major blood vessels or nerves (T1-T3). It has spread to nearby lymph nodes (N1) but not to distant sites (M0).

Stage III (T4, Any N, M0): The tumour is growing outside the pancreas into nearby major blood vessels or nerves (T4). It may or may not have spread to nearby lymph nodes (Any N). It has not spread to distant sites (M0).

Stage IV (Any T, Any N, M1): The cancer has spread to distant sites (M1).

Alternatively or additionally, by "early pancreatic cancer" (or "early stage pancreatic cancer") we include or mean asymptomatic pancreatic cancer. Common presenting symptoms of pancreatic cancers include jaundice, abdominal pain, weight loss, steatorrhoea, and new-onset diabetes. For example, the pancreatic cancer may be present at least 1 week before symptoms (e.g., common symptoms) are observed or observable, for example, $\geq 2$ weeks, $\geq 3$ weeks, $\geq 4$ weeks, $\geq 5$ weeks, $\geq 6$ weeks, $\geq 7$ weeks, $\geq 8$ weeks, $\geq 3$ months, $\geq 4$ months, $\geq 5$ months, $\geq 6$ months, $\geq 7$ months, $\geq 8$ months, $\geq 9$ months, $\geq 10$ months, $\geq 11$ months, $\geq 12$ months, ≥18 months, ≥2 years, ≥3 years, ≥4 years, or ≥5 years, before symptoms are observed or observable.

Thus, by "early pancreatic cancer" (or "early stage pancreatic cancer") we include pancreatic cancers that are of insufficient size and/or developmental stage to be diagnosed by conventional clinical methods. For example, by "early pancreatic cancer" or "early stage pancreatic cancer" we include or mean pancreatic cancers present at least 1 week before the pancreatic cancer is diagnosed or diagnosable by conventional clinical methods, for example, ≥2 weeks, ≥3 weeks, ≥4 weeks, ≥5 weeks, ≥6 weeks, ≥7 weeks, ≥8 weeks, ≥3 months, ≥4 months, ≥5 months, ≥6 months, ≥7 months, ≥8 months, ≥9 months, ≥10 months, ≥11 months, ≥12 months, ≥18 months, ≥2 years, ≥3 years, ≥4 years, or ≥5 years, before the pancreatic cancer is diagnosed or diagnosable by convention clinical methods.

The contemporary best practice for clinical pancreatic cancer diagnosis will be well known to the person of skill in the art, however, for a detailed review see Ducreux et al., 2015, 'Cancer of the pancreas: ESMO Clinical Practice Guidelines for diagnosis, treatment and follow-up' *Annals of Oncology*, 26 (Supplement 5): v56-v68 which is incorporated by reference herein.

Conventional clinical diagnoses (e.g., "diagnosed by conventional clinical methods") include CT scan, ultrasound, endoscopic ultrasound, biopsy (histopathology) and/or physical examination (e.g., of the abdomen and, possibly, local lymph nodes). In one embodiment by "conventional clinical diagnoses" (and the like) we include the pancreatic cancer diagnosis procedures set out in Ducreux et al., 2015, supra.

Conventional clinical diagnoses (and the like) may include or exclude the use of molecular biomarkers present in bodily fluids (such as blood, serum, interstitial fluid, lymph, urine, mucus, saliva, sputum, sweat) and or tissues.

It will be appreciated by persons skilled in the art that the early pancreatic cancer may be a resectable pancreatic cancer.

By "resectable pancreatic cancer" we include or mean that the pancreatic cancer comprises or consists of tumours that are (and/or are considered) capable of being removed by surgery (i.e., are resectable). For example, the pancreatic cancer may be limited to the pancreas (i.e., it does not extend beyond the pancreas and/or have not metastasized).

In one embodiment, the early pancreatic cancer comprises tumours of 30 mm or less in all dimensions (i.e., in this embodiment individuals with early pancreatic cancer do not comprise pancreatic cancer tumours of greater than 30 mm in any dimension), for example, equal to or less than 29 mm, 28 mm, 27 mm, 26 mm, 25 mm, 24 mm, 22 mm, 21 mm, 20 mm, 19 mm, 18 mm, 17 mm, 16 mm, 15 mm, 14 mm, 13 mm, 12 mm, 11 mm, 10 mm, 9 mm, 8 mm, 7 mm, 6 mm, 5 mm, 4 mm, 3 mm, 2 mm, 1 mm or equal to or 0.1 mm in all dimensions. Alternatively or additionally, the pancreatic cancer tumours of 30 mm or less in all dimensions are at least 2 mm in one dimension.

Alternatively or additionally, the pancreatic cancer tumours of 30 mm or less in all dimensions are at least 2 mm all dimensions.

It will be appreciated by persons skilled in the art that the methods of the invention will typically be used to provide an initial diagnosis, for example to identify an individual at risk of having or developing pancreatic cancer, after which further clinical investigations (such as biopsy testing, in vivo imaging and the like) may be performed to confirm the diagnosis.

By "sample to be tested", "test sample" or "control sample" we include a tissue or fluid sample taken or derived from an individual, wherein the sample comprises endogenous proteins and/or nucleic acid molecules and/or carbohydrate moieties. Preferably, the sample to be tested is provided from a mammal. Most preferably, the mammal is human.

The sample to be tested in the methods of the invention may be a cell, tissue or fluid sample (or derivative thereof) comprising or consisting of blood (fractionated or unfractionated), plasma, plasma cells, serum, tissue cells or equally preferred, protein or nucleic acid derived from a cell or tissue sample.

In one embodiment, the sample is a pancreatic tissue sample. In an alternative or additional embodiment, the sample is a sample of pancreatic cells.

Preferably, the sample may be a blood or serum sample.

In the methods of the invention, step (b) comprises or consists of measuring the presence and/or amount of one or more biomarker(s) listed in Table A, for example at least 2, 3, 4, 5, 6, 7, 8, 9, 10, 11, 12 or all 13 of the biomarkers listed in Table A.

In a particular additional or alternative embodiment, step (b) comprises or consists of measuring the presence and/or amount of six or more biomarker(s) listed in Table A, for example at least 7, 8, 9, 10, 11, 12 or all 13 of the biomarkers listed in Table A.

In the methods of the invention, step (b) comprises or consists of measuring the presence and/or amount of one or more biomarker(s) listed in Table A(i)-(vi), for example at least 2, 3, 4, 5, 6, 7, 8, 9, 10, 11, or all 12 of the biomarkers listed in Table A(i)-(vi).

In a particular additional or alternative embodiment, step (b) comprises or consists of measuring the presence and/or amount of six or more biomarker(s) listed in Table A(i)-(vi), for example at least 7, 8, 9, 10, 11 or all 12 of the biomarkers listed in Table A(i)-(vi).

In an additional or alternative embodiment, step (b) comprises or consists of measuring the presence and/or amount of three or more biomarkers listed in Table A(i)-(v), for example at least 4, 5, 6, 7, 8, or 9 of the biomarkers listed in Table A(i)-(v).

In an additional or alternative embodiment, step (b) comprises or consists of measuring the presence and/or amount of one or more, e.g. 2, 3, 4, 5, 6, 7, or all 8 of the following biomarkers, and/or one or more secondary target(s) thereof: OPG, GSN, IGFBP3, Complement Factor B, MUC16, Complement C4, Complement C5, Cystatin C.

Optionally, the one or more secondary target(s) are selected from: VWF, HADH2, FCN2, MASP2.

By "secondary target(s)" we include any target bound by off-target binding, by the antibody or other binding agent, to one or more additional biomarker(s) other than the primary target biomarker (direct co-enrichment), and/or one or more additional biomarker(s) bound, by the antibody or other binding agent, due to interaction of the one or more additional biomarker(s) with the intended primary target biomarker (indirect co-enrichment). Note that the primary target does not need to be biologically or clinically more relevant than the secondary target(s).

For example, FCN2 and MASP2 are secondary targets of the MUC16 (1) clone as the scFv antibody directed against MUC16 was also shown to bind FCN2 and MASP2 (direct co-enrichment). As another example, VWF is a secondary target of the OPG (2) clone as it was bound by the same scFv antibody, which is expected to be due to the ability of OPG to form a complex with VWF (indirect co-enrichment). See Tables 3 and 4 for details of those antibodies and their sequences.

In an additional or alternative embodiment, step (b) comprises or consists of measuring the presence and/or amount of the following biomarkers:

OPG, GSN, IGFBP3, Complement Factor B, MUC16, Complement C4, Complement C5, and Cystatin C; and optionally, measuring the presence and/or amount of one or more additional biomarkers selected from: VWF, HADH2, FCN2, MASP2.

In an additional or alternative embodiment, step (b) comprises or consists of measuring the presence and/or amount of all of the biomarkers listed in Table A (e.g. at the protein, mRNA and/or ctDNA level).

In an additional or alternative embodiment, step (b) comprises or consist of measuring the presence and/or amount of two or more of: OPG, VWF, GSN, IGFBP3, MUC16, FCN2, MASP2.

In an additional or alternative embodiment, step (b) comprises or consists of measuring the presence and/or amount of: (i) GSN and/or HADH2; and/or (ii) OPG and/or VWF.

In an additional or alternative embodiment, step (b) comprises or consists of measuring the presence and/or amount of: (i) GSN and/or HADH2; (ii) OPG and/or VWF; (iii) IGFBP3; and/or (iv) Complement Factor B.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C4; (vi) Complement C5; (vii) Cystatin C; and/or (viii) MUC16, FCN2 and/or MASP2.

In an additional or alternative embodiment, step (b) comprises or consists of measuring the presence and/or amount of: (i) GSN and/or HADH2; and (ii) OPG and/or VWF.

In an additional or alternative embodiment, step (b) comprises or consists of measuring the presence and/or amount of: (i) GSN and/or HADH2; (ii) OPG and/or VWF; (iii) IGFBP3; and (iv) Complement Factor B.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C4; (vi) Complement C5; (vii) Cystatin C; and (viii) MUC16, FCN2 and/or MASP2.

In an additional or alternative embodiment, step (b) comprises or consists of measuring the presence and/or amount of VWF, FCN2, and/or MASP2.

In an additional or alternative embodiment, step (b) comprises or consists of measuring the presence and/or amount of one or more of: OPG, VWF, GSN, IGFBP3, MUC16, FCN2 and/or MASP2.

In an additional or alternative embodiment, step (b) comprises or consists of measuring the presence and/or amount of CA 19-9 (carbohydrate antigen 19-9). In particular, embodiments of any of the methods described herein may comprise measuring the presence and/or amount of CA 19-9 together with measuring the presence and/or amount of any combination of biomarkers listed in Table A(i)-(vi). CA 19-9 may be measured at the same or different time to the measurement of the other biomarkers.

In an additional or alternative embodiment, step (b) excludes measuring the presence and/or amount of CA 19-9 (carbohydrate antigen 19-9). In particular, embodiments of any of the methods described herein may exclude measuring the presence and/or amount of CA 19-9.

In an additional or alternative embodiment, step (b) excludes measuring the presence and/or amount of Complement Factor B. In particular, embodiments of any of the methods described herein may exclude measuring the presence and/or amount of Complement Factor B.

In an additional or alternative embodiment, step (b) comprises or consists of measuring the presence and/or amount of: (i) GSN and/or HADH2; (ii) OPG and/or VWF; and (iii) CA 19-9.

In an additional or alternative embodiment, step (b) comprises or consists of measuring the presence and/or amount of: (i) GSN and/or HADH2; (ii) OPG and/or VWF; (iii) Complement Factor B; and (iv) CA 19-9.

In an additional or alternative embodiment, step (b) comprises or consists of measuring the presence and/or amount of: (i) GSN and/or HADH2; (ii) OPG and/or VWF; (iii) IGFBP3; and (iv) CA 19-9.

In an additional or alternative embodiment, step (b) comprises or consists of measuring the presence and/or amount of: (i) OPG and/or VWF; (ii) Complement Factor B; (iii) IGFBP3; and (iv) CA 19-9.

In an additional or alternative embodiment, step (b) comprises or consists of measuring the presence and/or amount of: (i) GSN and/or HADH2; (ii) IGFBP3; (iii) MUC16 and/or FCN2 and/or MASP2; and (iv) CA 19-9.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; and (v) CA 19-9.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C5; and (vi) CA 19-9.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C5; (vi) MUC16 and/or FCN2 and/or MASP2; and (vii) CA 19-9.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C5; (vi) Cystatin C; (vii) MUC16 and/or FCN2 and/or MASP2; and (viii) CA 19-9.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C4; (vi) Complement C5; (vii) Cystatin C; (viii) MUC16 and/or FCN2 and/or MASP2; and (ix) CA 19-9.

In an additional or alternative embodiment, step (b) comprises or consists of measuring the presence and/or amount of: (i) GSN and/or HADH2; (ii) Complement Factor B; (iii) Complement C5; (iv) Cystatin C; (v) Complement C4; and (vi) CA 19-9.

In an additional or alternative embodiment, step (b) comprises or consists of measuring the presence and/or amount of: (i) IGFBP3; (ii) Complement Factor B; (iii) Complement C5; (iv) Cystatin C; (v) Complement C4; and (vi) CA 19-9.

In an additional or alternative embodiment, step (b) comprises or consists of measuring the presence and/or amount of: (i) MUC16 and/or FCN2 and/or MASP2; (ii)

Complement Factor B; (iii) Complement C5; (iv) Cystatin C; (v) Complement C4; and (vi) CA 19-9.

In an additional or alternative embodiment, step (b) comprises or consists of measuring the presence and/or amount of: (i) OPG and/or VWF; (ii) Complement Factor B; (iii) Complement C5; (iv) Cystatin C; (v) Complement C4; and (vi) CA 19-9.

In an additional or alternative embodiment, step (b) comprises or consists of measuring the presence and/or amount of: (i) Complement Factor B; (ii) Complement C5; (iii) Cystatin C; (iv) Complement C4; and (v) CA 19-9.

In an additional or alternative embodiment, step (b) comprises or consists of measuring the presence and/or amount of: (i) GSN and/or HADH2; and (ii) OPG and/or VWF.

In an additional or alternative embodiment, step (b) comprises or consists of measuring the presence and/or amount of: (i) GSN and/or HADH2; (ii) OPG and/or VWF; and (iii) Complement Factor B.

In an additional or alternative embodiment, step (b) comprises or consists of measuring the presence and/or amount of: (i) GSN and/or HADH2; (ii) OPG and/or VWF; and (iii) IGFBP3.

In an additional or alternative embodiment, step (b) comprises or consists of measuring the presence and/or amount of: (i) OPG and/or VWF; (ii) Complement Factor B; and (iii) IGFBP3.

In an additional or alternative embodiment, step (b) comprises or consists of measuring the presence and/or amount of: (i) GSN and/or HADH2; (ii) IGFBP3; and (iii) MUC16 and/or FCN2 and/or MASP2.

In an additional or alternative embodiment, step (b) comprises or consists of measuring the presence and/or amount of: (i) GSN and/or HADH2; (ii) OPG and/or VWF; (iii) Complement Factor B; and (iv) IGFBP3.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; and (v) Complement C5.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C5; and (vi) MUC16 and/or FCN2 and/or MASP2.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C5; (vi) Cystatin C; and (vii) MUC16 and/or FCN2 and/or MASP2.

In an additional or alternative embodiment, step (b) comprises or consists of measuring the presence and/or amount of: (i) GSN and/or HADH2; (ii) OPG and/or VWF; (iii) Complement Factor B; (iv) IGFBP3; (v) Complement C4; (vi) Complement C5; (vii) Cystatin C; and (viii) MUC16 and/or FCN2 and/or MASP2.

In an additional or alternative embodiment, step (b) comprises or consists of measuring the presence and/or amount of: (i) GSN and/or HADH2; (ii) Complement Factor B; (iii) Complement C5; (iv) Cystatin C; and (v) Complement C4.

In an additional or alternative embodiment, step (b) comprises or consists of measuring the presence and/or amount of: (i) IGFBP3; (ii) Complement Factor B; (iii) Complement C5; (iv) Cystatin C; and (v) Complement C4.

In an additional or alternative embodiment, step (b) comprises or consists of measuring the presence and/or amount of: (i) MUC16 and/or FCN2 and/or MASP2; (ii) Complement Factor B; (iii) Complement C5; (iv) Cystatin C; and (v) Complement C4.

In an additional or alternative embodiment, step (b) comprises or consists of measuring the presence and/or amount of: (i) OPG and/or VWF; (ii) Complement Factor B; (iii) Complement C5; (iv) Cystatin C; and (v) Complement C4.

In an additional or alternative embodiment, step (b) comprises or consists of measuring the presence and/or amount of one or more biomarker(s) listed in Table A, part (i) and/or part (ii).

In an additional or alternative embodiment, step (b) comprises or consists of measuring the presence and/or amount of one or more biomarker(s) listed in Table A, part (i) and/or part (iii) and/or part (v).

In an additional or alternative embodiment, step (b) comprises or consists of measuring the presence and/or amount of GSN and OPG.

In an additional or alternative embodiment, step (b) comprises or consists of measuring the presence and/or amount of GSN, OPG, and IGFBP3.

In an additional or alternative embodiment, step (b) comprises or consists of measuring the presence and/or amount of GSN, OPG, Complement Factor B, and IGFBP3.

In an additional or alternative embodiment, step (b) comprises or consists of measuring the presence and/or amount of GSN, OPG, Complement Factor B, IGFBP3, Complement C4, Complement C5, Cystatin C, and MUC16.

In an additional or alternative embodiment, step (b) comprises or consists of measuring the presence and/or amount of GSN, OPG, IGFBP3, Complement C4, Complement C5, Cystatin C, and MUC16.

In an additional or alternative embodiment of any of the aspects of the invention described herein, in step (b) the presence and/or amount in the test sample of VWF is measured in addition to the presence and/or amount of OPG.

In an additional or alternative embodiment of any of the aspects of the invention described herein, in step (b) the presence and/or amount in the test sample of VWF is measured instead of the presence and/or amount of OPG. In an additional or alternative embodiment of each of the aspects of the invention described herein, in step (b) the presence and/or amount in the test sample of OPG is measured instead of VWF.

As detailed in Tables 3 and 5, the antibody sequence referred to herein as binding OPG may also bind VWF.

In an additional or alternative embodiment of any of the aspects of the invention described herein, measuring the presence and/or amount in the test sample of OPG and/or VWF in step (b) is replaced by measuring the presence and/or amount in the test sample of one or more protein bound by the antibody sequence of SEQ ID NO: 36. Preferably the protein bound by the antibody sequence of SEQ ID NO: 36 is OPG and/or VWF.

In an additional or alternative embodiment of any of the aspects of the invention described herein, in step (b) presence and/or amount in the test sample of HADH2 is measured in addition to the presence and/or amount of GSN (gelsolin).

In an additional or alternative embodiment of any of the aspects of the invention described herein, in step (b) the presence and/or amount in the test sample of HADH2 is measured instead of the presence and/or amount of GSN. In an additional or alternative embodiment of each of the aspects of the invention described herein, in step (b) the presence and/or amount in the test sample of GSN is measured instead of HADH2.

As detailed in Tables 3 and 5, the antibody sequence referred to herein as binding GSN may also bind HADH2.

In an additional or alternative embodiment of any of the aspects of the invention described herein, measuring the presence and/or amount in the test sample of GSN and/or HADH2 in step (b) is replaced by measuring the presence and/or amount in the test sample of one or more protein bound by the antibody sequence of SEQ ID NO: 20. Preferably the protein bound by the antibody sequence of SEQ ID NO: 20 is GSN and/or HADH2.

In an additional or alternative embodiment of any of the aspects of the invention described herein, in step (b) the presence and/or amount in the test sample of FCN2 and/or MASP2 is measured in addition to the presence and/or amount of MUC16 (CA125).

In an additional or alternative embodiment of any of the aspects of the invention described herein, in step (b) the presence and/or amount in the test sample of FCN2 and/or MASP2 is measured instead of the presence and/or amount of MUC16. In an additional or alternative embodiment of each of the aspects of the invention described herein, in step (b) the presence and/or amount in the test sample of MUC16 is measured instead of FCN2 and/or MASP2.

As detailed in Table 3, the antibody sequence referred to herein as binding MUC16 may also bind FCN2 and/or MASP2.

In an additional or alternative embodiment of any of the aspects of the invention described herein, measuring the presence and/or amount in the test sample of MUC16, FCN2 and/or MASP2 in step (b) is replaced by measuring the presence and/or amount in the test sample of one or more protein bound by the antibody sequence of SEQ ID NO: 30. Preferably the protein bound by the antibody sequence of SEQ ID NO: 30 is MUC16, FCN2 and/or MASP2.

In an additional or alternative embodiment of any of the aspects of the invention described herein, measuring the presence and/or amount in the test sample of one or more biomarkers in step (b) is replaced by measuring the presence and/or amount in the test sample of one or more protein bound by one or more binding agent comprising one or more of the antibody sequences described in Table 5 and/or Table 6.

In an additional or alternative embodiment of any of the aspects of the invention described herein, measuring the presence and/or amount in the test sample of one or more biomarkers in step (b) is replaced by measuring the presence and/or amount in the test sample of one or more protein bound by one or more binding agents comprising one or more of the antibody sequences defined in Table 5, specifically one or more of SEQ ID NOs: 6, 11, 13, 15, 20, 30, 32, and 36.

In an additional or alternative embodiment, step (b) may comprise, consist of or exclude measuring the expression of OPG. Alternatively or additionally, step (b) comprises, consists of or excludes measuring the expression of VWF. Alternatively or additionally, step (b) comprises, consists of or excludes measuring the expression of GSN. Alternatively or additionally, step (b) comprises, consists of or excludes measuring the expression of HADH2. Alternatively or additionally, step (b) comprises, consists of or excludes measuring the expression of Complement Factor B. Alternatively or additionally, step (b) comprises, consists of or excludes measuring the expression of IGFBP3. Alternatively or additionally, step (b) comprises, consists of or excludes measuring the expression of Complement C4. Alternatively or additionally, step (b) comprises, consists of or excludes measuring the expression of Complement C5. Alternatively or additionally, step (b) comprises, consists of or excludes measuring the expression of Cystatin C. Alternatively or additionally, step (b) comprises, consists of or excludes measuring the expression of MUC16. Alternatively or additionally, step (b) comprises, consists of or excludes measuring the expression of FCN2. Alternatively or additionally, step (b) comprises, consists of or excludes measuring the expression of MASP2. Alternatively or additionally, step (b) comprises, consists of or excludes measuring the expression of CA19-9.

Thus, in an additional or alternative embodiment, step (b) comprises or consists of measuring the presence and/or amount of one or more biomarker listed in:
(i) Table A, part (i), for example both of the biomarkers listed in Table A(i); and/or
(ii) Table A, part (ii), for example both of the biomarkers listed in Table A(ii); and/or
(iii) Table A, part (iii); and/or
(iv) Table A, part (iv); and/or
(v) Table A, part (v), for example 2 or all of the biomarkers listed in Table A(v); and/or
(vi) Table A, part (vi), for example 2 or all of the biomarkers listed in Table A(vi); and/or
(vii) Table A, part (vii).

It will be appreciated that step (b) may additionally comprise measuring the presence and/or amount of one or more further biomarkers not listed in Table A, wherein the further biomarkers may provide additional diagnostic information.

For example, step (b) may comprise or consist of measuring the presence and/or amount of one or more biomarker(s) listed in Table 1.

For example, step (b) may comprise or consist of measuring the presence and/or amount of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or all of the biomarkers in Table 1.

As another example, step (b) may comprise or consist of measuring the presence and/or amount of one or more biomarker(s) listed in Table 2.

In one preferred embodiment of the first aspect of the invention, step (b) comprises measuring the presence and/or amount of all of the biomarkers listed in Table A, e.g. at the protein level. Use of this biomarker signature allows the diagnosis of pancreatic cancer (i.e. PDAC) at any stage, including early stages of the disease, and including distinguishing from healthy individuals and individuals with symptoms suggestive or consistent with pancreatic cancer. Preferably, step (b) comprises measuring the presence and/or amount of CA19-9.

It will be appreciated by persons skilled in the art that, in addition to measuring the biomarkers in a sample from an individual to be tested, the methods of the invention may also comprise measuring those same biomarkers in one or more control samples.

Thus, in one embodiment, the method further comprises or consists of the steps of:
(c) providing one or more (negative) control samples from:
(i) an individual not afflicted with pancreatic cancer; and/or
(ii) an individual afflicted with a benign pancreatic and/or biliary disease, e.g. chronic pancreatitis or diabetes, e.g. new-onset diabetes (e.g. type II); and (d) determining a biomarker signature of the one or more control samples by measuring the presence and/or amount in the control sample of the one or more biomarkers measured in step (b);

wherein the pancreatic cancer-associated disease state is identified in the event that the presence and/or amount in the test sample of the one or more biomarkers measured in step (b) is different from the presence and/or amount in the control sample of the one or more biomarkers measured in step (d).

By "is different to the presence and/or amount in a control sample" we include that the presence and/or amount of the one or more biomarker(s) in the test sample differs from that of the one or more control sample(s) (or to predefined reference values representing the same). Preferably, the presence and/or amount in the test sample differs from the presence or amount in one or more control sample(s) (or mean of the control samples) by at least ±5%, for example, at least ±6%, ±7%, ±8%, ±9%, ±10%, ±11%, ±12%, ±13%, ±14%, ±15%, ±16%, ±17%, ±18%, ±19%, ±20%, ±21%, ±22%, ±23%, ±24%, ±25%, ±26%, ±27%, ±28%, ±29%, ±30%, ±31%, ±32%, ±33%, ±34%, ±35%, ±36%, ±37%, ±38%, ±39%, ±40%, ±41%, ±42%, ±43%, ±44%, ±45%, ±41%, ±42%, ±43%, ±44%, ±55%, ±60%, ±65%, ±66%, ±67%, ±68%, ±69%, ±70%, ±71%, ±72%, ±73%, ±74%, ±75%, ±76%, ±77%, ±78%, ±79%, ±80%, ±81%, ±82%, ±83%, ±84%, ±85%, ±86%, ±87%, ±88%, ±89%, ±90%, ±91%, ±92%, ±93%, ±94%, ±95%, ±96%, ±97%, ±98%, ±99%, ±100%, ±125%, ±150%, ±175%, ±200%, ±225%, ±250%, ±275%, ±300%, ±350%, ±400%, ±500% or at least ±1000% of the one or more control sample(s) (e.g., the negative control sample).

Alternatively or additionally, the presence or amount in the test sample differs from the mean presence or amount in the control samples by at least >1 standard deviation from the mean presence or amount in the control samples, for example, ≥1.5, ≥2, ≥3, ≥4, ≥5, ≥6, ≥7, ≥8, ≥9, ≥10, ≥11, ≥12, ≥13, ≥14 or ≥15 standard deviations from the mean presence or amount in the control samples. Any suitable means may be used for determining standard deviation (e.g., direct, sum of square, Welford's), however, in one embodiment, standard deviation is determined using the direct method (i.e., the square root of [the sum the squares of the samples minus the mean, divided by the number of samples]).

Alternatively or additionally, by "is different to the presence and/or amount in a control sample" we include that the presence or amount in the test sample does not correlate with the amount in the control sample in a statistically significant manner. By "does not correlate with the amount in the control sample in a statistically significant manner" we mean or include that the presence or amount in the test sample correlates with that of the control sample with a p-value of >0.001, for example, >0.002, >0.003, >0.004, >0.005, >0.01, >0.02, >0.03, >0.04 >0.05, >0.06, >0.07, >0.08, >0.09 or >0.1. Any suitable means for determining p-value known to the skilled person can be used, including z-test, t-test, Student's t-test, f-test, Mann-Whitney U test, Wilcoxon signed-rank test and Pearson's chi-squared test.

In an additional or alternative embodiment, a decrease in the amount of GSN and/or HADH2 measured in step (b) as compared to a negative control sample is indicative of the pancreatic cancer-associated disease state in the individual.

In an additional or alternative embodiment, a decrease in the amount of IGFBP3 measured in step (b) as compared to a negative control sample is indicative of the pancreatic cancer-associated disease state in the individual.

In an additional or alternative embodiment, a decrease in the amount of MUC16, FCN2 and/or MASP2 measured in step (b) as compared to a negative control sample is indicative of the pancreatic cancer-associated disease state in the individual.

In an additional or alternative embodiment, an increase in the amount of OPG and/or VWF measured in step (b) as compared to a negative control sample is indicative of the pancreatic cancer-associated disease state in the individual.

In an additional or alternative embodiment, an increase in the amount of Complement Factor B measured in step (b) as compared to a negative control sample is indicative of the pancreatic cancer-associated disease state in the individual.

In an additional or alternative embodiment, an increase in the amount of Complement C5 measured in step (b) as compared to a negative control sample is indicative of the pancreatic cancer-associated disease state in the individual.

In an additional or alternative embodiment, an increase in the amount of Complement C4 measured in step (b) as compared to a negative control sample is indicative of the pancreatic cancer-associated disease state in the individual.

In an additional or alternative embodiment, an increase in the amount of Cystatin C measured in step (b) as compared to a negative control sample is indicative of the pancreatic cancer-associated disease state in the individual.

In an additional or alternative embodiment, an increase in the amount of CA 19-9 measured in step (b) as compared to a negative control sample is indicative of the pancreatic cancer-associated disease state in the individual.

In one embodiment, the method of the invention may further comprise or consist of the steps of:
(e) providing one or more (positive) control sample from an individual afflicted with pancreatic cancer; and
(f) determining a biomarker signature of the control sample by measuring the presence and/or amount in the control sample of the one or more biomarkers measured in step (b);

wherein the pancreatic cancer-associated disease state is identified in the event that the presence and/or amount in the test sample of the one or more biomarkers measured in step (b) corresponds to the presence and/or amount in the control sample of the one or more biomarkers measured in step (f).

Thus, the methods of the invention may comprise steps (c)+(d) and/or steps (e)+(f).

By "corresponds to the presence and/or amount in a control sample" we include that the presence and/or amount is identical to that of a positive control sample; or closer to that of one or more positive control sample than to one or more negative control sample (or to predefined reference values representing the same). Preferably the presence and/or amount is within ±40% of that of the one or more control sample (or mean of the control samples), for example, within ±39%, ±38%, ±37%, ±36%, ±35%, ±34%, ±33%, ±32%, ±31%, ±30%, ±29%, ±28%, ±27%, ±26%, ±25%, ±24%, ±23%, ±22%, ±21%, ±20%, ±19%, ±18%, ±17%, ±16%, ±15%, ±14%, ±13%, ±12%, ±11%, ±10%, ±9%, ±8%, ±7%, ±6%, ±5%, ±4%, ±3%, ±2%, ±1%, ±0.05% or within 0% of the one or more control sample (e.g., the positive control sample).

Alternatively or additionally, the difference in the presence or amount in the test sample is ≤5 standard deviation from the mean presence or amount in the control samples, for example, ≤4.5, ≤4, ≤3.5, ≤3, ≤2.5, ≤2, ≤1.5, ≤1.4, ≤1.3, ≤1.2, ≤1.1, ≤1, ≤0.9, ≤0.8, ≤0.7, ≤0.6, ≤0.5, ≤0.4, ≤0.3, ≤0.2, ≤0.1 or 0 standard deviations from the from the mean presence or amount in the control samples, provided that the standard deviation ranges for differing and corresponding biomarker expressions do not overlap (e.g., abut, but no not overlap).

Alternatively or additionally, by "corresponds to the presence and/or amount in a control sample" we include that the presence or amount in the test sample correlates with the amount in the control sample in a statistically significant manner. By "correlates with the amount in the control sample in a statistically significant manner" we mean or include that the presence or amount in the test sample correlates with the that of the control sample with a p-value of ≤0.05, for example, ≤0.04, ≤0.03, ≤0.02, ≤0.01, ≤0.005, ≤0.004, ≤0.003, ≤0.002, ≤0.001, ≤0.0005 or ≤0.0001.

Differential expression (up-regulation or down regulation) of biomarkers, or lack thereof, can be determined by any suitable means known to a skilled person. Differential expression is determined to a p value of a least less than 0.05 (p=<0.05), for example, at least <0.04, <0.03, <0.02, <0.01, <0.009, <0.005, <0.001, <0.0001, <0.00001 or at least <0.000001. For example, differential expression may be determined using a support vector machine (SVM).

In one embodiment, the SVM is, or is derived from, the SVM script described in Table 7.

It will be appreciated by persons skilled in the art that differential expression may relate to a single biomarker or to multiple biomarkers considered in combination (i.e., as a biomarker signature). Thus, a p value may be associated with a single biomarker or with a group of biomarkers. Indeed, proteins having a differential expression p value of greater than 0.05 when considered individually may nevertheless still be useful as biomarkers in accordance with the invention when their expression levels are considered in combination with one or more other biomarkers.

As exemplified in the accompanying Example, the expression of certain proteins in a tissue, blood, serum or plasma test sample may be indicative of pancreatic cancer in an individual. For example, the relative expression of certain serum proteins in a single test sample may be indicative of the presence of pancreatic cancer in an individual.

In an alternative or additional embodiment, the presence and/or amount in the test sample of the one or more biomarkers measured in step (b) may be compared against predetermined reference values representative of the measurements in steps (d) and/or (f), i.e., reference negative and/or positive control values.

As detailed above, the methods of the invention may also comprise measuring, in one or more negative or positive control samples, the presence and/or amount of the one or more biomarkers measured in the test sample in step (b).

For example, one or more negative control samples may be from an individual who was not, at the time the sample was obtained, afflicted with:
  (a) a pancreatic cancer, for example adenocarcinoma (e.g., pancreatic ductal adenocarcinoma or tubular papillary pancreatic adenocarcinoma), pancreatic sarcoma, malignant serous cystadenoma, adenosquamous carcinoma, signet ring cell carcinoma, hepatoid carcinoma, colloid carcinoma, undifferentiated carcinoma, and undifferentiated carcinomas with osteoclast-like giant cells; and/or
  (b) a non-cancerous pancreatic disease or condition, for example acute pancreatitis, chronic pancreatitis and autoimmune pancreatitis; and/or
  (c) any other disease or condition.

Thus, the negative control sample may be obtained from a healthy individual.

Likewise, one or more positive control samples may be from an individual who, at the time the sample was obtained, was afflicted with a pancreatic cancer, for example adenocarcinoma (e.g., pancreatic ductal adenocarcinoma or tubular papillary pancreatic adenocarcinoma), pancreatic sarcoma, malignant serous cystadenoma, adenosquamous carcinoma, signet ring cell carcinoma, hepatoid carcinoma, colloid carcinoma, undifferentiated carcinoma, and undifferentiated carcinomas with osteoclast-like giant cells; and/or a non-cancerous pancreatic disease or condition, for example acute pancreatitis, chronic pancreatitis and autoimmune pancreatitis; and/or any other disease or condition.

In one preferred embodiment of the first aspect of the invention, the method is repeated on the individual. Thus, steps (a) and (b) may be repeated using a sample from the same individual taken at different time to the original sample tested (or the previous method repetition). Such repeated testing may enable disease progression to be assessed, for example to determine the efficacy of the selected treatment regime and (if appropriate) to select an alternative regime to be adopted.

Thus, in one embodiment, the method is repeated using a test sample taken between 1 day to 104 weeks to the previous test sample(s) used, for example, between 1 week to 100 weeks, 1 week to 90 weeks, 1 week to 80 weeks, 1 week to 70 weeks, 1 week to 60 weeks, 1 week to 50 weeks, 1 week to 40 weeks, 1 week to 30 weeks, 1 week to 20 weeks, 1 week to 10 weeks, 1 week to 9 weeks, 1 week to 8 weeks, 1 week to 7 weeks, 1 week to 6 weeks, 1 week to 5 weeks, 1 week to 4 weeks, 1 week to 3 weeks, or 1 week to 2 weeks.

Alternatively or additionally, the method may be repeated using a test sample taken every period from the group consisting of: 1 day, 2 days, 3 day, 4 days, 5 days, 6 days, 7 days, 10 days, 2 weeks, 3 weeks, 4 weeks, 5 weeks, 6 weeks, 7 weeks, 8 weeks, 9 weeks, 10 weeks, 15 weeks, 20 weeks, 25 weeks, 30 weeks, 35 weeks, 40 weeks, 45 weeks, 50 weeks, 55 weeks, 60 weeks, 65 weeks, 70 weeks, 75 weeks, 80 weeks, 85 weeks, 90 weeks, 95 weeks, 100 weeks, 104, weeks, 105 weeks, 110 weeks, 115 weeks, 120 weeks, 125 weeks and 130 weeks.

Alternatively or additionally, the method may be repeated at least once, for example, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23, 24 times or 25 times.

Alternatively or additionally, the method is repeated continuously.

In one embodiment, the method is repeated until pancreatic cancer is diagnosed in the individual using the methods of the present invention and/or conventional clinical methods (i.e., until confirmation of the diagnosis is made).

Suitable conventional clinical methods are well known in the art. For example, those methods described in Ducreux et al., 2015, 'Cancer of the pancreas: ESMO Clinical Practice Guidelines for diagnosis, treatment and follow-up' *Annals of Oncology*, 26 (Supplement 5): v56-v68 and/or Freelove & Walling, 2006, 'Pancreatic Cancer: Diagnosis and Management' *American Family Physician*, 73(3):485-492 which are incorporated herein by reference. Thus, the pancreatic cancer diagnosis may be confirmed using one or more method selected from the group consisting of computed tomography (preferably dual-phase helical computed tomography); transabdominal ultrasonography; endoscopic ultrasonography-guided fine-needle aspiration; endoscopic retrograde cholangio-pancreatography; positron emission tomography; magnetic resonance imaging; physical examination; and biopsy.

Alternatively and/or additionally, the pancreatic cancer diagnosis may be confirmed using known biomarker signatures for the diagnosis of pancreatic cancer. For example, the pancreatic cancer may be diagnosed with one or more biomarker or diagnostic method described in the group consisting of: WO 2008/117067 A9; WO 2012/120288 A2; WO 2015/067969 A2; WO 2017/050939 A2; WO 2017/194613 A2; and WO 2018/141804 A1.

In one preferred embodiment of the methods of the invention, step (a) comprises providing a serum sample from an individual to be tested and/or step (b) comprises measuring in the sample the expression of the protein or polypeptide of the one or more biomarker(s). Thus, a biomarker signature for the sample may be determined at the protein level.

In such an embodiment, step (b), (d) and/or step (f) may be performed using one or more first binding agents capable of binding to a biomarker (i.e., protein) listed in Table A. It will be appreciated by persons skilled in the art that the first binding agent may comprise or consist of a single species with specificity for one of the protein biomarkers or a plurality of different species, each with specificity for a different protein biomarker.

In an additional or alternative embodiment, one or more first binding agent(s) comprise(s) one or more of the antibody sequence(s) defined in Table 5 and/or Table 6.

In an additional or alternative embodiment, one or more first binding agent(s) comprise(s) one or more of the antibody sequences of SEQ ID NOs: 6, 11, 13, 15, 20, 30, 32, and 36.

In an additional or alternative embodiment, one or more first binding agent(s) comprise(s) one or more of the antibody sequences of SEQ ID NOs: 30, 32, and 36.

It will be appreciated that any combination of antibody sequences defined in Table 5 may be used in the methods of the invention, for example combinations correlating with each or any of the different combinations of biomarkers which may be measured as set out above.

Suitable binding agents (also referred to as binding molecules) can be selected from a library, based on their ability to bind a given target molecule, as discussed below.

In one preferred embodiment, at least one type of the binding agents, and more typically all of the types, may comprise or consist of an antibody or antigen-binding fragment of the same, or a variant thereof.

Methods for the production and use of antibodies are well known in the art, for example see *Antibodies: A Laboratory Manual,* 1988, Harlow & Lane, Cold Spring Harbor Press, ISBN-13: 978-0879693145, *Using Antibodies: A Laboratory Manual,* 1998, Harlow & Lane, Cold Spring Harbor Press, ISBN-13: 978-0879695446 and *Making and Using Antibodies: A Practical Handbook,* 2006, Howard & Kaser, CRC Press, ISBN-13: 978-0849335280 (the disclosures of which are incorporated herein by reference).

Thus, a fragment may contain one or more of the variable heavy ($V_H$) or variable light ($V_L$) domains. For example, the term antibody fragment includes Fab-like molecules (Better et al (1988) *Science* 240, 1041); Fv molecules (Skerra et al (1988) *Science* 240, 1038); single-chain Fv (scFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544).

For example, the binding agent(s) may be scFv molecules.

The term "antibody variant" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecule capable of binding to an antigen in an immunoassay format that is known to those skilled in the art.

A general review of the techniques involved in the synthesis of antibody fragments which retain their specific binding sites is to be found in Winter & Milstein (1991) *Nature* 349, 293-299.

Molecular libraries such as antibody libraries (Clackson et al, 1991, *Nature* 352, 624-628; Marks et al, 1991, *J Mol Biol* 222(3): 581-97), peptide libraries (Smith, 1985, *Science* 228(4705): 1315-7), expressed cDNA libraries (Santi et al (2000) *J Mol Biol* 296(2): 497-508), libraries on other scaffolds than the antibody framework such as affibodies (Gunneriusson et al, 1999, *Appl Environ Microbiol* 65(9): 4134-40) or libraries based on aptamers (Kenan et al, 1999, *Methods Mol Biol* 118, 217-31) may be used as a source from which binding molecules that are specific for a given motif are selected for use in the methods of the invention.

Conveniently, the binding agent(s) may be immobilised on a surface (e.g., on a multiwell plate or array); see Example below.

In one embodiment of the methods of the invention, step (b), (d) and/or step (f) is performed using an assay comprising a second binding agent capable of binding to the one or more biomarkers, the second binding agent comprising a detectable moiety. For example, an immobilised (first) binding agent may initially be used to 'trap' the protein biomarker on to the surface of a microarray, and then a second binding agent may be used to detect the 'trapped' protein.

The second binding agent may be as described above in relation to the (first) binding agent, such as an antibody or antigen-binding fragment thereof.

It will be appreciated by skilled person that the one or more biomarkers (e.g., proteins) in the test sample may be labelled with a detectable moiety, prior to performing step (b). Likewise, the one or more biomarkers in the control sample(s) may be labelled with a detectable moiety.

Alternatively, or in addition, the first and/or second binding agents may be labelled with a detectable moiety.

By a "detectable moiety" we include the meaning that the moiety is one which may be detected and the relative amount and/or location of the moiety (for example, the location on an array) determined.

Suitable detectable moieties are well known in the art. For example, the detectable moiety may be selected from the group consisting of: a fluorescent moiety; a luminescent moiety; a chemiluminescent moiety; a radioactive moiety; an enzymatic moiety.

In one preferred embodiment, the detectable moiety is biotin.

Thus, the detectable moiety may be a fluorescent and/or luminescent and/or chemiluminescent moiety which, when exposed to specific conditions, may be detected. For example, a fluorescent moiety may need to be exposed to radiation (i.e., light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

In a further alternative, the detectable moiety may be a radioactive atom which is useful in imaging. Suitable radioactive atoms include $^{99m}$Tc and $^{123}$I for scintigraphic studies. Other readily detectable moieties include, for example, spin labels for magnetic resonance imaging (MRI) such as $^{123}$I again, $^{131}$I, $^{111}$In, $^{19}$F, $^{13}$C, $^{15}$N, $^{17}$O, gadolinium, manganese or iron. Clearly, the agent to be detected (such as, for example, the one or more biomarkers in the test sample and/or control sample described herein and/or an antibody molecule for use in detecting a selected protein) must have sufficient of the appropriate atomic isotopes in order for the detectable moiety to be readily detectable.

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Conveniently, the assay is an ELISA (Enzyme Linked Immunosorbent Assay) which typically involves the use of enzymes giving a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemiluminescent systems based on enzymes such as luciferase can also be used.

ELISA methods are well known in the art, for example see The ELISA Guidebook (Methods in Molecular Biology), 2000, Crowther, Humana Press, ISBN-13: 978-0896037281 (the disclosures of which are incorporated by reference).

Alternatively, conjugation with the vitamin biotin is frequently used since this can readily be detected by its reaction with enzyme-linked avidin or streptavidin to which it binds with great specificity and affinity.

In one preferred embodiment, step (b), (d) and/or step (f) may be performed using an array.

Arrays per se are well known in the art. Typically, they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. By using well-known techniques, such as contact or non-contact printing, masking or photolithography, the location of each spot can be defined. For reviews see Jenkins, R. E., Pennington, S. R. (2001, *Proteomics*, 2, 13-29) and Lal et al (2002, *Drug Discov Today* 15; 7(18 Suppl):S143-9).

Typically, the array is a microarray. By "microarray" we include the meaning of an array of regions having a density of discrete regions of at least about 100/cm$^2$, and preferably at least about 1000/cm$^2$. The regions in a microarray have typical dimensions, e.g., diameters, in the range of between about 10-250 µm, and are separated from other regions in the array by about the same distance. The array may also be a macroarray or a nanoarray.

Once suitable binding molecules (discussed above) have been identified and isolated, the skilled person can manufacture an array using methods well known in the art of molecular biology.

Examples of array formats are described below in the Example and references cited therein; e.g., see Steinhauer et al., 2002; Wingren and Borrebaeck, 2008; Wingren et al., 2005, Delfani et al., 2016 (the disclosure of which are incorporated herein by reference).

Thus, in an exemplary embodiment the method comprises:

(i) labelling biomarkers present in the sample (e.g., serum) with biotin;
(ii) contacting the biotin-labelled proteins with an array comprising a plurality of scFv immobilised at discrete locations on its surface, the scFv having specificity for one or more of the proteins in Table A(i)-(vi);
(iii) contacting the biotin-labelled proteins (immobilised on the surface-bound scFv) with a streptavidin conjugate comprising a fluorescent dye; and
(iv) detecting the presence of the dye at discrete locations on the array surface wherein the expression of the dye on the array surface is indicative of the expression of a biomarker from Table A in the sample.

In an additional or alternative embodiment, the presence and/or amount CA 19-9 is measured as part of the method. CA 19-9 may be measured together with the other biomarkers defined in Table A, or separately. For example, CA 19-9 may be measured via a separate ELISA method. The data for CA 19-9 may then be analysed together with or separately from the data for the other biomarkers defined in Table A in order to determine the pancreatic cancer-associated disease state.

In an alternative embodiment, step (b), (d) and/or (f) comprises measuring the expression of a nucleic acid molecule encoding the one or more biomarkers.

The nucleic acid molecule may be a gene expression intermediate or derivative thereof, such as a mRNA or cDNA.

Thus, measuring the expression of the one or more biomarker(s) in step (b), (d) and/or (f) may be performed using a method selected from the group consisting of Southern hybridisation, Northern hybridisation, polymerase chain reaction (PCR), reverse transcriptase PCR (RT-PCR), quantitative real-time PCR (qRT-PCR), nanoarray, microarray, macroarray, autoradiography and in situ hybridisation.

For example, measuring the expression of the one or more biomarker(s) in step (b), (d) and/or (f) may be performed using one or more binding moieties, each individually capable of binding selectively to a nucleic acid molecule encoding one of the biomarkers identified in Table A.

Conveniently, the one or more binding moieties each comprise or consist of a nucleic acid molecule, such as DNA, RNA, PNA, LNA, GNA, TNA or PMO.

Advantageously, the one or more binding moieties are 5 to 100 nucleotides in length. For example, 15 to 35 nucleotides in length.

It will be appreciated that the nucleic acid-based binding moieties may comprise a detectable moiety.

Thus, the detectable moiety may be selected from the group consisting of: a fluorescent moiety; a luminescent moiety; a chemiluminescent moiety; a radioactive moiety (for example, a radioactive atom); or an enzymatic moiety.

Alternatively or additionally, the detectable moiety may comprise or consist of a radioactive atom, for example selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

Alternatively or additionally, the detectable moiety of the binding moiety may be a fluorescent moiety.

In a further embodiment, the nucleic acid molecule is a circulating tumour DNA molecule (ctDNA).

Methods suitable for detecting ctDNA are now well-established; for example, see Lewis et al., 2016, *World J Gastroenterol.* 22(32): 7175-7185, and references cited therein (the disclosures of which are incorporated herein by reference).

As detailed above, the sample provided in step (a) (and/or in step (c) and/or (e)) may be selected from the group consisting of unfractionated blood, plasma, serum, tissue fluid, pancreatic tissue, milk, bile and urine.

Conveniently, the sample provided in step (a), (c) and/or (e) is serum.

By appropriate selection of some or all of the biomarkers in Table A, optionally in conjunction with one or more further biomarkers, e.g. one or more additional biomarkers from Table 1, the methods of the invention exhibit high predictive accuracy for diagnosis of pancreatic cancer.

Thus, the predictive accuracy of the method, as determined by an ROC AUC value, may be at least 0.50, for example at least 0.55, 0.60, 0.65, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or at least 0.99.

Thus, in one embodiment, the predictive accuracy of the method, as determined by a ROC AUC value, is at least 0.80, or preferably at least 0.83.

Thus, in another embodiment, the predictive accuracy of the method, as determined by an ROC AUC value, is at least 0.90, or preferably at least 0.92.

In the methods of the invention, the 'raw' data obtained in step (b) (and/or in step (d) and/or (e)) undergoes one or more analysis steps before a diagnosis is reached. For example, the raw data may need to be standardised against one or more control values (i.e., normalised).

Typically, diagnosis is performed using a support vector machine (SVM), such as those available from cran.r-project.org/web/packages/e1071/index.html (e.g. e1071 1.5-24). However, any other suitable means may also be used.

Support vector machines (SVMs) are a set of related supervised learning methods used for classification and regression. Given a set of training examples, each marked as belonging to one of two categories, an SVM training algorithm builds a model that predicts whether a new example falls into one category or the other. Intuitively, an SVM model is a representation of the examples as points in space, mapped so that the examples of the separate categories are divided by a clear gap that is as wide as possible. New examples are then mapped into that same space and predicted to belong to a category based on which side of the gap they fall on.

More formally, a support vector machine constructs a hyperplane or set of hyperplanes in a high or infinite dimensional space, which can be used for classification, regression or other tasks. Intuitively, a good separation is achieved by the hyperplane that has the largest distance to the nearest training data points of any class (so-called functional margin), since in general the larger the margin the lower the generalization error of the classifier. For more information on SVMs, see for example, Burges, 1998, Data Mining and Knowledge Discovery, 2:121-167.

In one embodiment of the invention, the SVM is 'trained' prior to performing the methods of the invention using biomarker profiles from individuals with known disease status (for example, individuals known to have pancreatic cancer, individuals known to have acute inflammatory pancreatitis, individuals known to have chronic pancreatitis or individuals known to be healthy). By running such training samples, the SVM is able to learn what biomarker profiles are associated with pancreatic cancer. Once the training process is complete, the SVM is then able to determine whether or not the biomarker sample tested is from an individual with pancreatic cancer.

However, this training procedure can be by-passed by pre-programming the SVM with the necessary training parameters. For example, diagnoses can be performed according to the known SVM parameters using the SVM algorithm detailed in Table 7, based on the measurement of any or all of the biomarkers listed in Table A.

It will be appreciated by skilled persons that suitable SVM parameters can be determined for any combination of the biomarkers listed in Table A by training an SVM machine with the appropriate selection of data (i.e. biomarker measurements from individuals with known pancreatic cancer status). Alternatively, the data of the Examples and figures may be used to determine a particular pancreatic cancer-associated disease state according to any other suitable statistical method known in the art.

Preferably, the method of the invention has an accuracy of at least 60%, for example 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% accuracy.

Preferably, the method of the invention has a sensitivity of at least 60%, for example 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sensitivity. The method of the invention may have a sensitivity of at least 83%.

Preferably, the method of the invention has a specificity of at least 60%, for example 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% specificity. The method of the invention may have a specificity of at least 95%.

By "accuracy" we mean the proportion of correct outcomes of a method, by "sensitivity" we mean the proportion of all pancreatic cancer positive sample that are correctly classified as positives, and by "specificity" we mean the proportion of all pancreatic cancer negative samples that are correctly classified as negatives.

Signal intensities may be quantified using any suitable means known to the skilled person, for example using Array-Pro (Media Cybernetics). Signal intensity data may be normalised (i.e., to adjust technical variation). Normalisation may be performed using any suitable method known to the skilled person. Alternatively or additionally, data are normalised using the empirical Bayes algorithm ComBat (Johnson et al., 2007).

Further statistical analysis of the refined data may be performed using methods well-known in the art, such as PCA, q-value calculation by ANOVA, and/or fold change calculation.

As described above, a first ('training') data set may be used to identify a combination of biomarkers, e.g. from Table A, to serve as a biomarker signature for the diagnosis of pancreatic cancer. Mathematical analysis of the training data set may be performed using known algorithms to determine the most suitable biomarker signatures. The predictive accuracy of a given biomarker combination (signature) can then be verified against a new ('verification') data set.

It will be appreciated by persons skilled in the art that the individual(s) tested may be of any ethnicity or geographic origin. Alternatively, the individual(s) tested may be of a defined sub-population, e.g., based on ethnicity and/or geographic origin. For example, the individual(s) tested may be Caucasian and/or Chinese (e.g., Han ethnicity).

Typically, the sample(s) provided in step (a), (c) and/or (e) are provided before treatment of the pancreatic cancer (e.g., resection, chemotherapy, radiotherapy).

In one embodiment, the individual(s) being tested suffers from one or more condition selected from the group consisting of chronic pancreatitis, hereditary pancreatic ductal adenocarcinoma and Peutz-Jeghers syndrome.

The pancreatic cancer to be diagnosed may be selected from the group consisting of adenocarcinoma, adenosquamous carcinoma, signet ring cell carcinoma, hepatoid carcinoma, colloid carcinoma, undifferentiated carcinoma, and undifferentiated carcinomas with osteoclast-like giant cells. Preferably, the pancreatic cancer is a pancreatic adenocarcinoma. More preferably, the pancreatic cancer is pancreatic ductal adenocarcinoma, also known as exocrine pancreatic cancer.

One preferred embodiment of the first aspect of the invention includes the additional step (g), following positive diagnosis of the individual with a pancreatic cancer, of providing the individual with pancreatic cancer therapy.

Thus, a related aspect of the invention provides a method of treatment of an individual with a pancreatic cancer comprising the following steps:
(a) diagnosing an individual as having a pancreatic cancer using a method according to the first aspect of the invention; and
(b) treating the individual so diagnosed with a pancreatic cancer therapy (for example, see Thota et al., 2014, *Oncology* 28(1):70-4, the disclosures of which are incorporated herein by reference).

The pancreatic cancer therapy may be selected from the group consisting of surgery, chemotherapy, immunotherapy, chemoimmunotherapy, thermochemotherapy, radiotherapy and combinations thereof. For example, the pancreatic cancer therapy may be AC chemotherapy; Capecitabine and docetaxel chemotherapy (Taxotere®); CMF chemotherapy; Cyclophosphamide; EC chemotherapy; ECF chemotherapy; E-CMF chemotherapy (Epi-CMF); Eribulin (Halaven®); FEC chemotherapy; FEC-T chemotherapy; Fluorouracil (5FU); GemCarbo chemotherapy; Gemcitabine (Gemzar®); Gemcitabine and cisplatin chemotherapy (GemCis or Gem-Cisplat); GemTaxol chemotherapy; Idarubicin (Zavedos®); Liposomal doxorubicin (DaunoXome®); Mitomycin (Mitomycin C Kyowa®); Mitoxantrone; MM chemotherapy; MMM chemotherapy; Paclitaxel (Taxol®); TAC chemotherapy; Taxotere and cyclophosphamide (TC) chemotherapy; Vinblastine (Velbe®); Vincristine (Oncovin®); Vindesine (Eldisine®); and Vinorelbine (Navelbine®).

Accordingly, a further aspect of the invention provides an antineoplastic agent (or combination thereof) for use in treating pancreatic cancer wherein the dosage regime thereof is determined based on the results of the method of the first aspect of the invention.

A related aspect of the invention provides the use of an antineoplastic agent (or combination thereof) in treating pancreatic cancer wherein the dosage regime thereof is determined based on the results of the method of the first aspect of the invention.

A further related aspect of the invention provides the use of an antineoplastic agent (or combination thereof) in the manufacture of a medicament for treating pancreatic cancer wherein the dosage regime thereof is determined based on the results of the method of the first aspect of the invention.

Thus, the present invention also provides a method of treating pancreatic cancer comprising administering to a patient an effective amount of an antineoplastic agent (or combination thereof) wherein the amount of antineoplastic agent (or combination thereof) effective to treat the pancreatic cancer is determined based on the results of the method of the first aspect of the invention.

In one embodiment, the antineoplastic agent comprises or consists of an alkylating agent (ATC code L01a), an antimetabolite (ATC code L01b), a plant alkaloid or other natural product (ATC code L01c), a cytotoxic antibiotic or a related substance (ATC code L01d), or another antineoplastic agent (ATC code L01x).

Hence, in one embodiment the antineoplastic agent comprises or consists of an alkylating agent selected from the group consisting of a nitrogen mustard analogue (for example cyclophosphamide, chlorambucil, melphalan, chlormethine, ifosfamide, trofosfamide, prednimustine or bendamustine) an alkyl sulfonate (for example busulfan, treosulfan, or mannosulfan) an ethylene imine (for example thiotepa, triaziquone or carboquone) a nitrosourea (for example carmustine, lomustine, semustine, streptozocin, fotemustine, nimustine or ranimustine) an epoxides (for example etoglucid) or another alkylating agent (ATC code L01ax, for example mitobronitol, pipobroman, temozolomide or dacarbazine).

In another embodiment the antineoplastic agent comprises or consists of an antimetabolite selected from the group consisting of a folic acid analogue (for example methotrexate, raltitrexed, pemetrexed or pralatrexate), a purine analogue (for example mercaptopurine, tioguanine, cladribine, fludarabine, clofarabine or nelarabine) or a pyrimidine analogue (for example cytarabine, fluorouracil (5-FU), tegafur, carmofur, gemcitabine, capecitabine, azacitidine or decitabine).

In a still further embodiment the antineoplastic agent comprises or consists of a plant alkaloid or other natural product selected from the group consisting of a vinca alkaloid or a vinca alkaloid analogue (for example vinblastine, vincristine, vindesine, vinorelbine or vinflunine), a podophyllotoxin derivative (for example etoposide or teniposide) a colchicine derivative (for example demecolcine), a taxane (for example paclitaxel, docetaxel or paclitaxel poliglumex) or another plant alkaloids or natural product (ATC code L01cx, for example trabectedin).

In one embodiment the antineoplastic agent comprises or consists of a cytotoxic antibiotic or related substance selected from the group consisting of an actinomycine (for example dactinomycin), an anthracycline or related substance (for example doxorubicin, daunorubicin, epirubicin, aclarubicin, zorubicin, idarubicin, mitoxantrone, pirarubicin, valrubicin, amrubicin or pixantrone) or another (ATC code L01dc, for example bleomycin, plicamycin, mitomycin or ixabepilone).

In a further embodiment the antineoplastic agent comprises or consists of an antineoplastic agent selected from the group consisting of a platinum compound (for example cisplatin, carboplatin, oxaliplatin, satraplatin or polyplatillen) a methylhydrazine (for example procarbazine) a monoclonal antibody (for example edrecolomab, rituximab, trastuzumab, alemtuzumab, gemtuzumab, cetuximab, bevacizumab, panitumumab, catumaxomab or ofatumumab) a sensitizer used in photodynamic/radiation therapy (for example porfimer sodium, methyl aminolevulinate, aminolevulinic acid, temoporfin or efaproxiral) or a protein kinase inhibitor (for example imatinib, gefitinib, erlotinib, sunitinib, sorafenib, dasatinib, lapatinib, nilotinib, temsirolimus, everolimus, pazopanib, vandetanib, afatinib, masitinib or toceranib).

In a still further embodiment the antineoplastic agent comprises or consists of an antineoplastic agent selected from the group consisting of amsacrine, asparaginase, altretamine, hydroxycarbamide, lonidamine, pentostatin, miltefosine, masoprocol, estramustine, tretinoin, mitoguazone, topotecan, tiazofurine, irinotecan (camptosar), alitretinoin, mitotane, pegaspargase, bexarotene, arsenic trioxide, denileukin diftitox, bortezomib, celecoxib, anagrelide, oblimersen, sitimagene ceradenovec, vorinostat, romidepsin, omacetaxine mepesuccinate, eribulin or folinic acid.

In one embodiment the antineoplastic agent comprises or consists of a combination of one or more antineoplastic agent, for example, one or more antineoplastic agent defined herein. One example of a combination therapy used in the treatment of pancreatic cancer is FOLFIRINOX which is made up of the following four drugs:

FOL—folinic acid (leucovorin);
F—fluorouracil (5-FU);
IRIN—irinotecan (Camptosar); and
OX—oxaliplatin (Eloxatin).

Thus, by combining certain optional embodiments from the above-described methods, the invention may provide a method for diagnosing and treating pancreatic adenocarcinoma (e.g. stage I or II) in an individual, said method comprising:
  (a) obtaining or providing a serum or plasma sample for a human patient;
  (b) detecting the presence and/or amount of one or more (e.g. all) of the biomarkers from Table A in the sample (e.g. by contacting the sample with one or more antibodies, or antigen-binding fragments thereof, each having specificity for one of the biomarkers and detecting binding of said antibodies or fragments to said biomarkers);
  (c) diagnosing the patient with pancreatic adenocarcinoma (e.g. stage I or II) based on the presence and/or amount of the one or more biomarkers in the sample; and
  (d) administering an effective amount of a chemotherapeutic agent (e.g. gemcitabine) to the diagnosed patient and/or surgically removing the pancreas, in whole or in part, and/or administering radiotherapy.

It will be appreciated that step (b) may, for example, comprise determining the presence and/or amount in the sample of two or more, e.g. all, of the biomarkers listed in Table A. This step may comprise the use of an array, as described herein, e.g. comprising a plurality of scFvs, having specificity towards the biomarkers, immobilised on the surface of an array plate.

In an additional or alternative embodiment of any aspect of the invention, the presence and/or amount of CA 19-9 may be determined by a separate method, e.g. via an enzyme linked immunosorbent assay (ELISA) kit.

It will be appreciated that step (c) may comprise one or more further clinical investigations (such as testing a biopsy sample and/or in vivo imaging of the patient) in order to confirm or establish the diagnosis.

It will be appreciated that step (d) may comprise administration of combinations of chemotherapeutic agent and/or surgery and/or radiotherapy.

In one preferred embodiment, the patient is diagnosed with resectable pancreatic adenocarcinoma (e.g. stage I or II) and step (d) comprises surgical removal of the pancreas in whole or in part (e.g. using the Whipple procedure to remove the pancreas head or a total pancreatectomy) combined with chemotherapy (e.g. gemcitabine and/or 5-fluorouracil). It will be appreciated that the chemotherapy may be administered before and/or after the surgery.

In one embodiment, such methods permit the diagnosis of early stage pancreatic adenocarcinoma prior to the phenotypic presentation of the disease (i.e. before observable clinical symptoms develop). Thus, the methods may be used to diagnose pancreatic adenocarcinoma in asymptomatic patients, especially those at high risk of developing pancreatic cancer such as those with a family history of the disease, tobacco smokers, obese individuals, diabetics, and individuals with a chronic pancreatitis, chronic hepatitis B infection, cholelithiasis and/or an associated genetic predisposition (e.g. Peutz-Jeghers syndrome, familial atypical multiple mole melanoma syndrome, Lynch syndrome, BRCA1 mutations and/or BRCA2 mutations). Effective monitoring of such high-risk individuals can enable early diagnosis of pancreatic adenocarcinoma and so greatly increase the chances of survival.

Another aspect of the invention provides a method for treating a pancreatic cancer-associated disease state in a subject comprising or consisting of administering a pancreatic cancer therapy to a subject, wherein said subject has a biomarker signature of the present invention indicating the presence of the pancreatic cancer-associated disease state in the subject. The pancreatic cancer therapy may be resection, chemotherapy, and/or radiotherapy. In one embodiment, the pancreatic cancer therapy comprises the administration of at least one antineoplastic agent, as described hereinabove.

The method may further comprise (e.g. prior to treatment) measuring the presence and/or amount in a test sample of one or more biomarkers selected from the group defined in Table A (e.g. all the biomarkers in Table A). The method may comprise determining a biomarker signature of a test sample from the subject (e.g. prior to treatment), as described hereinabove.

Another aspect of the invention provides a method for detecting a biomarker signature of clinical significance (e.g. of diagnostic and/or prognostic value) in or of a biological sample (e.g. a serum sample), the method comprising steps (a) and (b) as defined above in relation to the first aspect of the invention. Preferably, the biomarker signature comprises or consists of all of the biomarkers in Table A.

A further aspect of the invention related to the first aspect of the invention provides a method for diagnosing or determining a pancreatic cancer-associated disease state comprising or consisting of the steps of:
(a) providing a sample from an individual to be tested; and
(b) determining a biomarker signature of the test sample by measuring the presence and/or amount in the test sample of one or more protein(s) bound by one or more of the antibody sequence(s) described in Table 5 and/or Table 6;
wherein the presence and/or amount in the test sample of the one or more protein(s) bound by one or more of the antibody sequence(s) described in Table 5 and/or Table 6 is indicative of the pancreatic cancer-associated disease state in the individual.

In an alternative or additional embodiment, step (b) comprises measuring the presence and/or amount in the test sample of one or more protein(s) bound by one or more of the antibody sequence(s) described in Table 5. For example, one or more protein(s) bound by one or more binding agent(s) comprising one or more of SEQ ID NO: 6, 11, 13, 15, 20, 30, 32, and 36.

All embodiments described in relation to the other aspects of the invention herein are equally applicable to this further aspect of the invention. Furthermore, this aspect of the invention may be combined with any embodiment of the first aspect of the invention. For example, the method may comprise, in step (b), measuring the presence and/or amount in the test sample of two or more biomarkers from Table A, together with measuring the presence and/or amount in the test sample of one or more protein(s) bound by one or more binding agent(s) comprising one or more of the antibody sequence(s) described in Table 5.

In one embodiment, the method comprises measuring the presence and/or amount in the test sample of one or more protein(s) bound by one or more binding agents comprising one or more of the antibody sequence(s) SEQ ID NO: 30, 32, and 36.

A further aspect of the invention provides an array for diagnosing or determining a pancreatic cancer-associated disease state in an individual comprising an agent or agents (such as any of the above-described binding agents) for detecting the presence in a sample of one or more of the biomarkers defined in Table A(i)-(vi), optionally additionally comprising an agent for detecting the presence of CA 19-9.

Thus, the array is suitable for performing a method according to the first or a subsequent aspect of the invention.

The array comprises one or more binding agents capable (individually or collectively) of binding to one or more of the biomarkers defined in Table A, either at the protein level or the nucleic acid level.

The array may comprise one or more, preferably two or more, binding agents, wherein the binding agents are each capable of binding selectively to a biomarker as defined in the first aspect. Therefore, the array may comprise or consist of a particular selection of biomarker-specific binding agents which correlates to any particular selection of biomarkers as defined in the first aspect.

In one preferred embodiment, the array comprises one or more antibodies, or antigen-binding fragments thereof, capable (individually or collectively) of binding to one or more of the biomarkers defined in Table A at the protein level. For example, the array may comprise scFv molecules capable (collectively) of binding to all of the biomarkers defined in Table A(i)-(vi) at the protein level, optionally the array may additionally comprise an agent for binding to CA 19-9.

In an alternative embodiment, the array comprises one or more antibodies, or antigen-binding fragments thereof, capable (individually or collectively) of binding to the following biomarkers:
(i) GSN and/or HADH2; (ii) OPG and/or VWF; (iii) Complement Factor B; (iv) IGFBP3; (v) Complement C4; (vi) Complement C5; (vii) Cystatin C; and (viii) MUC16, FCN2 and/or MASP2; and optionally one or more additional biomarkers from Table 1.

In an additional or alternative embodiment, the array comprises one or more antibodies, or antigen-binding fragments thereof, capable of binding to CA 19-9. However, CA 19-9 may be measured separately.

It will be appreciated that the array may comprise one or more positive and/or negative control samples. For example, conveniently the array comprises bovine serum albumin as a positive control sample and/or phosphate-buffered saline as a negative control sample.

Conveniently, the array comprises one or more, e.g. all, of the antibodies in Table 5.

Advantageously, the array comprises one or more, e.g. all, of the antibodies in Table 6.

A further aspect of the invention provides use of one or more biomarkers selected from the group defined in Table A as a biomarker for determining a pancreatic cancer associated disease states in an individual.

In an additional or alternative embodiment, the use comprises the following biomarkers:
(i) GSN and/or HADH2; (ii) OPG and/or VWF; (iii) Complement Factor B; (iv) IGFBP3; (v) Complement C4; (vi) Complement C5; (vii) Cystatin C; and (viii) MUC16 and/or FCN2 and/or MASP2; optionally including CA 19-19 and/or one or more additional biomarkers from Table 1.

For example, all of the biomarkers (e.g. proteins) defined in Table A may be used together as a diagnostic signature for determining the presence of pancreatic cancer in an individual.

A further aspect of the invention provides a kit for diagnosing or determining a pancreatic cancer-associated disease state in an individual comprising:
(a) an array according to the invention, or components for making the same; and
(b) instructions for performing the method as defined above (e.g., in the first or subsequent aspects of the invention).

A further aspect of the invention provides a use of one or more binding moieties to a biomarker as described herein (e.g. in Table A or specifically in Table A(i)-(vi)) in the preparation of a kit for diagnosing or determining a pancreatic cancer-associated disease state in an individual. Thus, multiple different binding moieties may be used, each targeted to a different biomarker, in the preparation of such as kit. In one embodiment, the binding moiety is an antibody or antigen-binding fragment thereof (e.g. scFv), as described herein.

A further aspect of the invention provides a method of treating pancreatic cancer in an individual comprising the steps of:
(a) determining a pancreatic cancer associated disease state according to the method defined in any the first or subsequent aspects of the invention; and
(b) providing the individual with pancreatic cancer therapy.

For example, the pancreatic cancer therapy may be selected from the group consisting of surgery (e.g., resection), chemotherapy, immunotherapy, chemoimmunotherapy and thermochemotherapy (see above).

A further aspect of the invention provides a computer program for operating the methods the invention, for example, for interpreting the expression data of step (c) (and subsequent expression measurement steps) and thereby diagnosing or determining a pancreatic cancer-associated disease state. The computer program may be a programmed SVM. The computer program may be recorded on a suitable computer-readable carrier known to persons skilled in the art. Suitable computer-readable-carriers may include compact discs (including CD-ROMs, DVDs, Blu-ray and the like), floppy discs, flash memory drives, ROM or hard disc drives. The computer program may be installed on a computer suitable for executing the computer program.

Preferred, non-limiting examples which embody certain aspects of the invention will now be described, with reference to the following figures:

The plot shows inverse unadjusted log 10 P-values plotted against log 2 fold change ratios (PDAC vs. controls) for the eight proteins included in the selected biomarker signature. Notice that the HADH2 (3) scFv clone mainly reflects the differential expression of gelsolin (GSN), and that the OPG (2) and MUC16 (1) clones may also reflect differential expression of the VWF and FCN2/MASP2, respectively.

Figure 2:
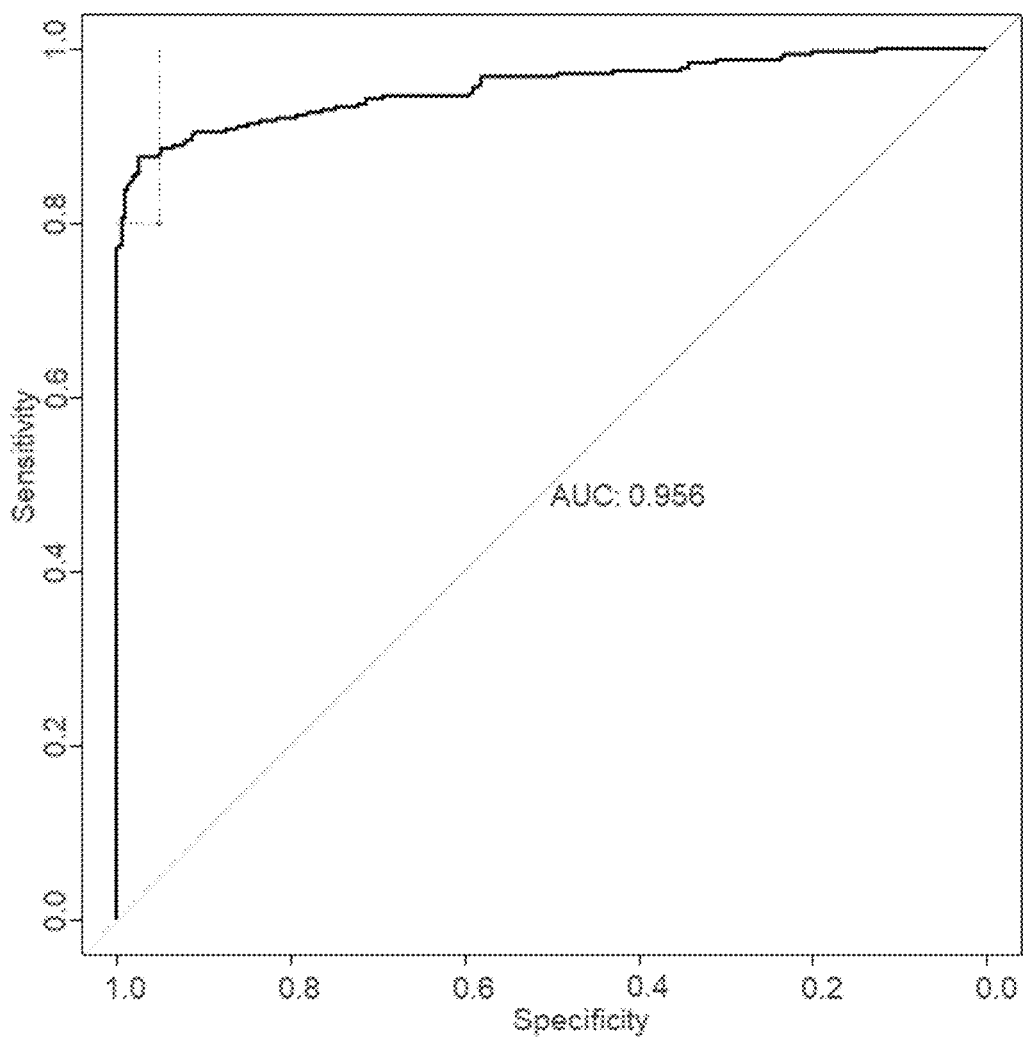

FIG. 2: Classification of Healthy Controls vs. PDAC Stage I-IV

Classification concerns healthy controls from patient samples of different PDAC stages. Data have been derived by the 8-plex microarray-based analysis in combination with CA19-9 ELISA. Results are presented as a ROC-curve with its corresponding AUC-value.

Figure 3:
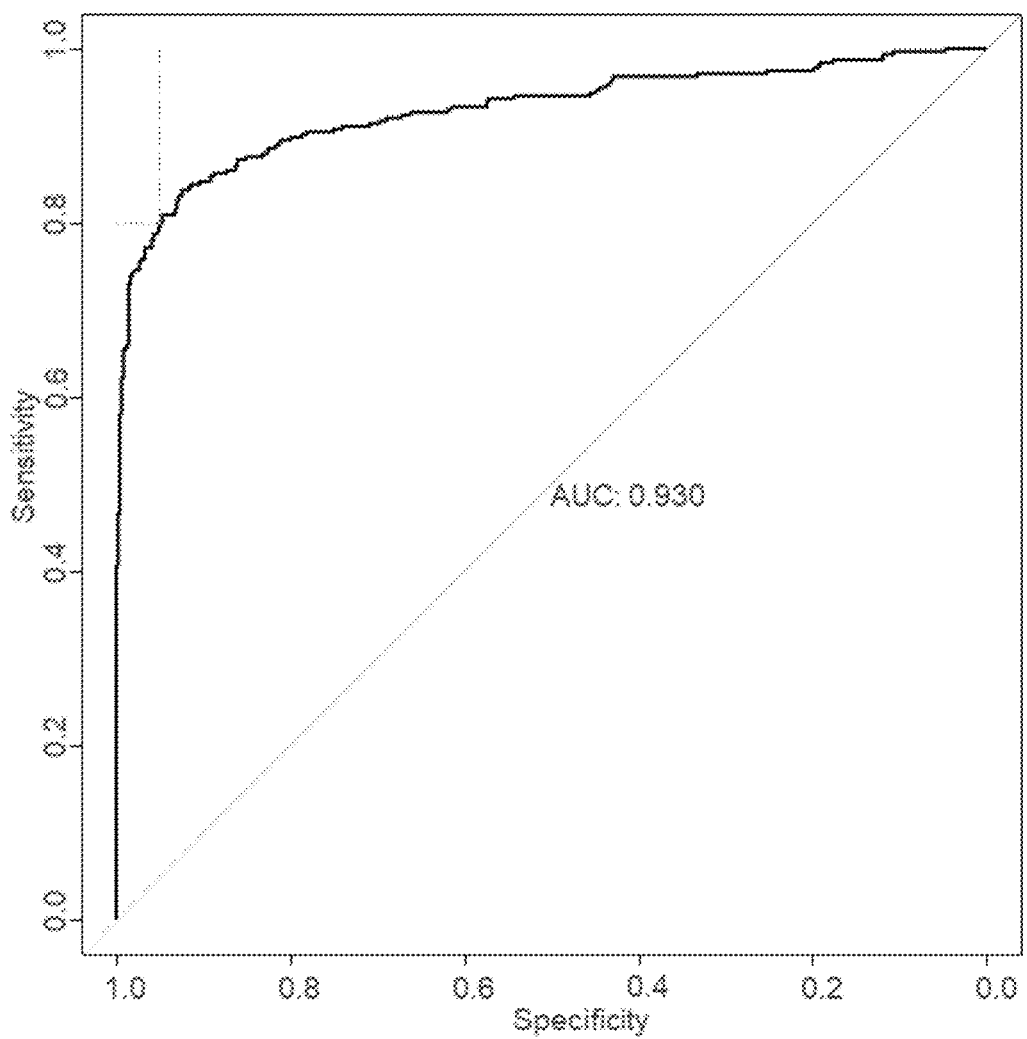

FIG. 3: Classification of Symptomatic Controls vs. PDAC Stage I-IV

Classification concerns symptomatic controls from patient samples of different PDAC stages. Data have been derived by the 8-plex microarray-based analysis in combination with CA19-9 ELISA. Results are presented as a ROC-curve with its corresponding AUC-value.

Figure 4:
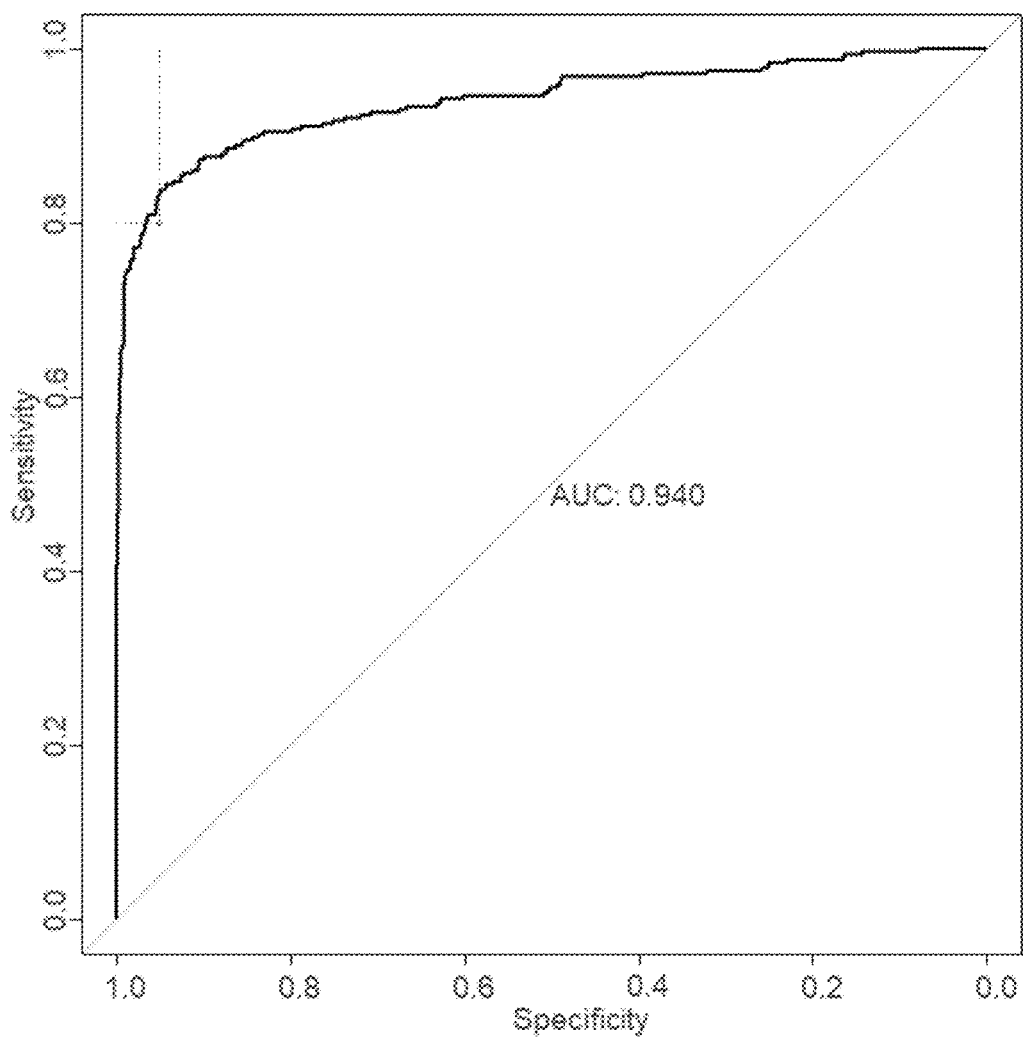

FIG. 4: Classification of All Controls vs. PDAC Stage I-IV

Classification of all controls (healthy and symptomatic) vs. patient samples of different PDAC stages. Data have been derived by the 8-plex microarray-based analysis in combination with CA19-9 ELISA. In total, 1113 samples were analyzed. The analysis yields a SVM ROC AUC-value of 0.94 differentiating PDAC from all controls.

Figure 5:
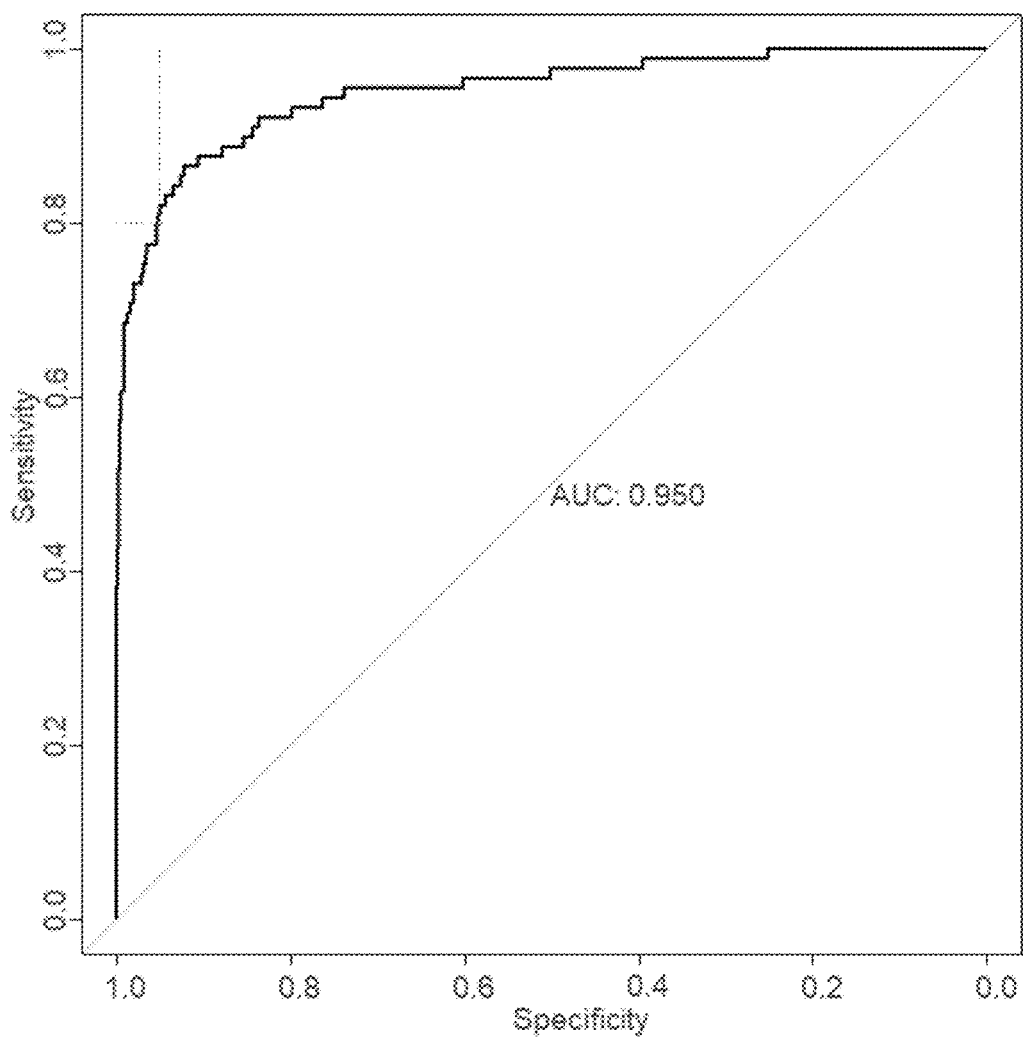

FIG. 5: Classification of All Controls vs. PDAC Stage I/II

Classification concerns all controls (healthy and symptomatic) from patient samples of early PDAC stages (I/II). Data have been derived by the 8-plex microarray-based analysis in combination with CA19-9 ELISA. The analysis yields a SVM ROC AUC-value of 0.95 differentiating 89 PDAC Stages I & II from all controls.

Figure 6:
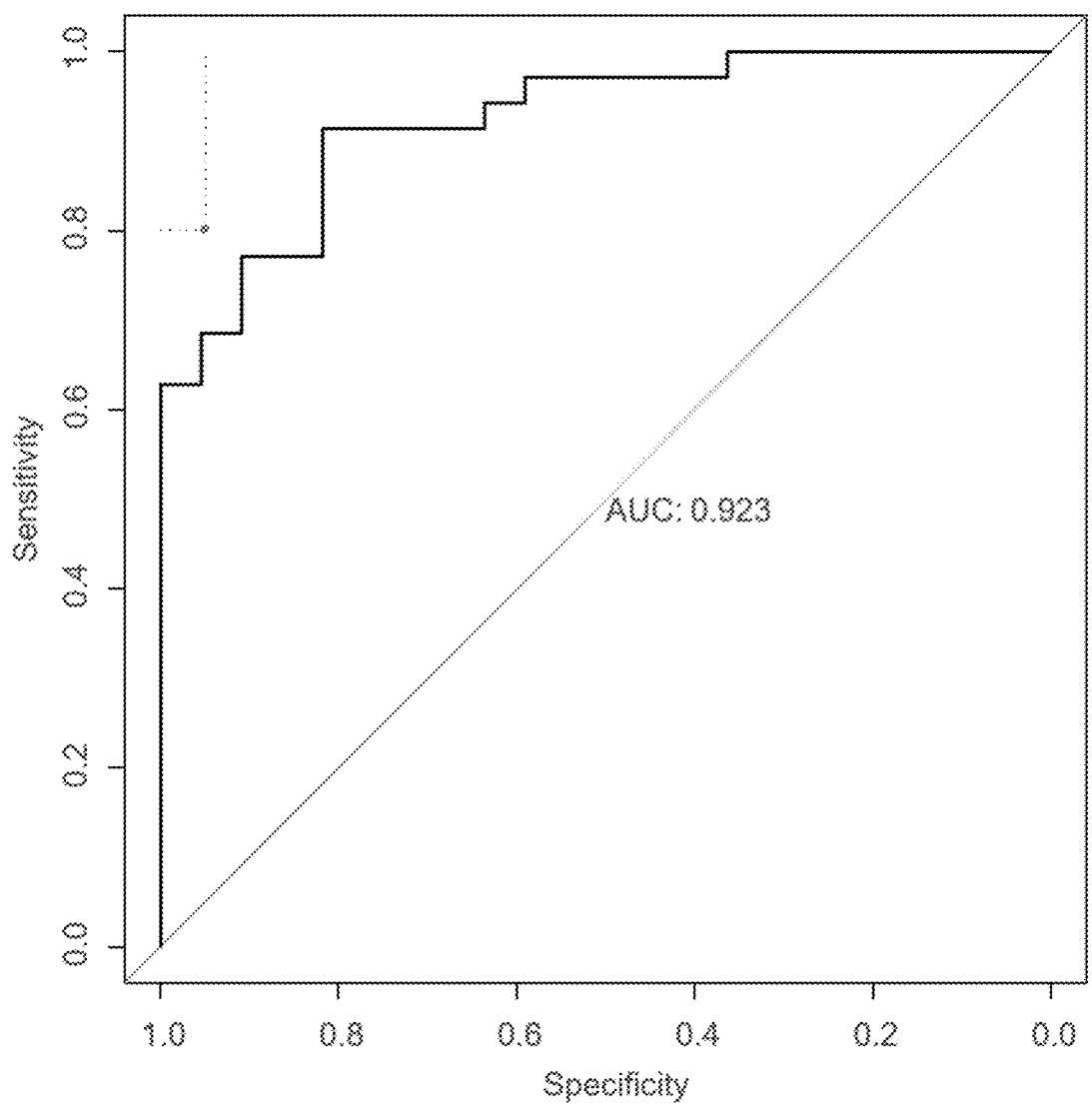

FIG. 6: Classification of Chronic Pancreatitis vs. PDAC Stage I/II

Classification concerns chronic pancreatitis controls (a subgroup of the symptomatic controls) from patient samples of early PDAC stages (I/II). Data have been derived by the 8-plex microarray-based analysis in combination with CA19-9 ELISA. Results are presented as a ROC-curve with its corresponding AUC-value.

Figure 7:
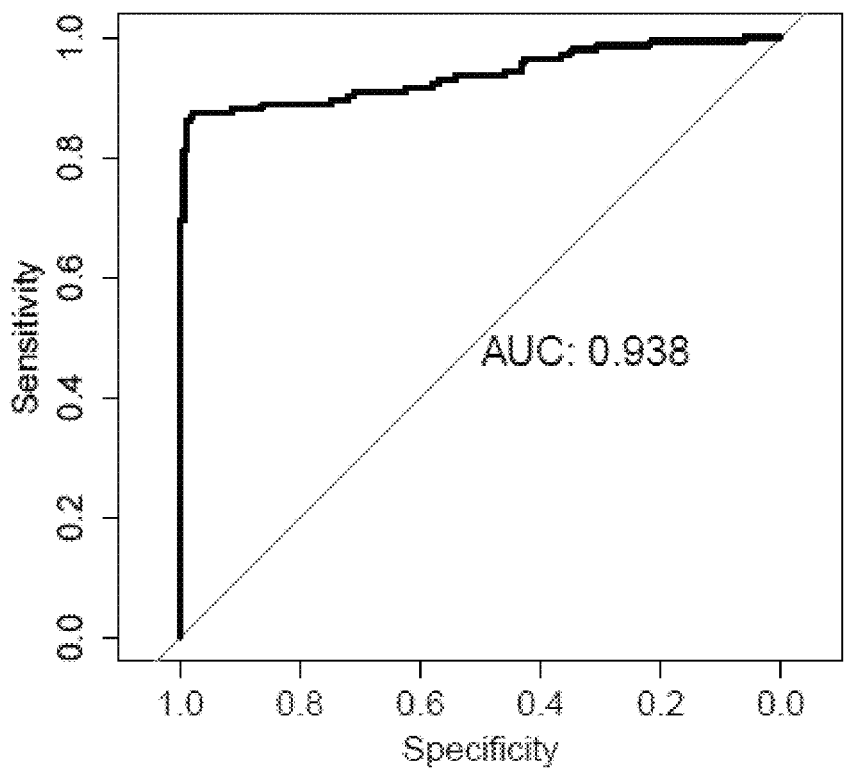

FIG. 7: Classification of PDAC Stage I-IV vs. Familial/Hereditary Controls

Classification of serum samples from patients with PDAC (all stages) vs. familial/hereditary controls in the blinded validation. Data have been derived by multiplex microarray-based analysis in combination with CA19-9 assessment. The analysis yields a ROC AUC-value of 0.94 differentiating PDAC samples (stages I-IV; n=167) from the familial/hereditary controls (n=203).

Figure 8:
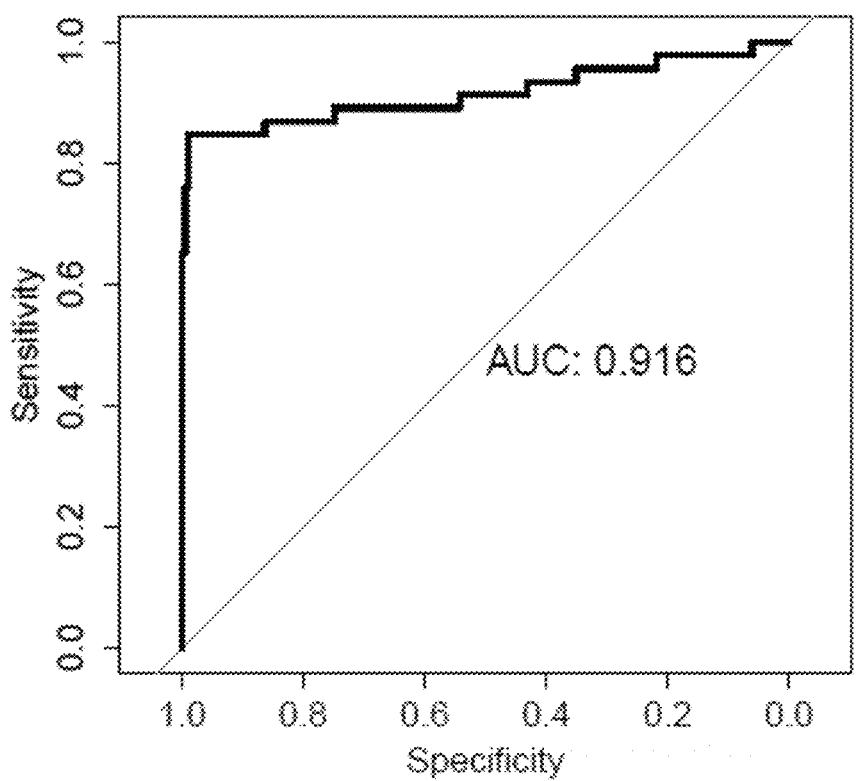

FIG. 8: Classification of PDAC Stage I/II vs. Familial/Hereditary Controls

Classification of serum samples from patients with early stage (stage I/II) PDAC vs. familial/hereditary controls in the blinded validation. Data have been derived by multiplex microarray-based analysis in combination with CA19-9 assessment. The analysis yields a ROC AUC-value of 0.92 differentiating early stage PDAC samples (stages I/II; n=56) from the familial/hereditary controls (n=203).

Figure 9:
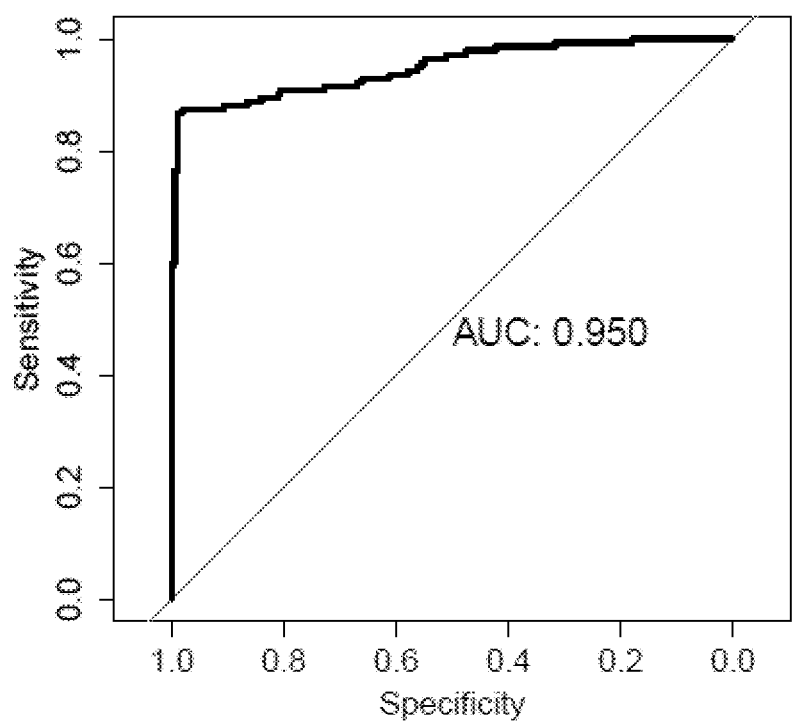

FIG. 9: Classification of PDAC Stage I-IV vs. Healthy Controls

Classification of serum samples from patients with PDAC (all stages) vs. healthy controls in the blinded validation. Data have been derived by multiplex microarray-based analysis in combination with CA19-9 assessment. The analysis yields a ROC AUC-value of 0.95 differentiating PDAC samples (stages I-IV; n=167) from the healthy controls (n=221).

Figure 10:
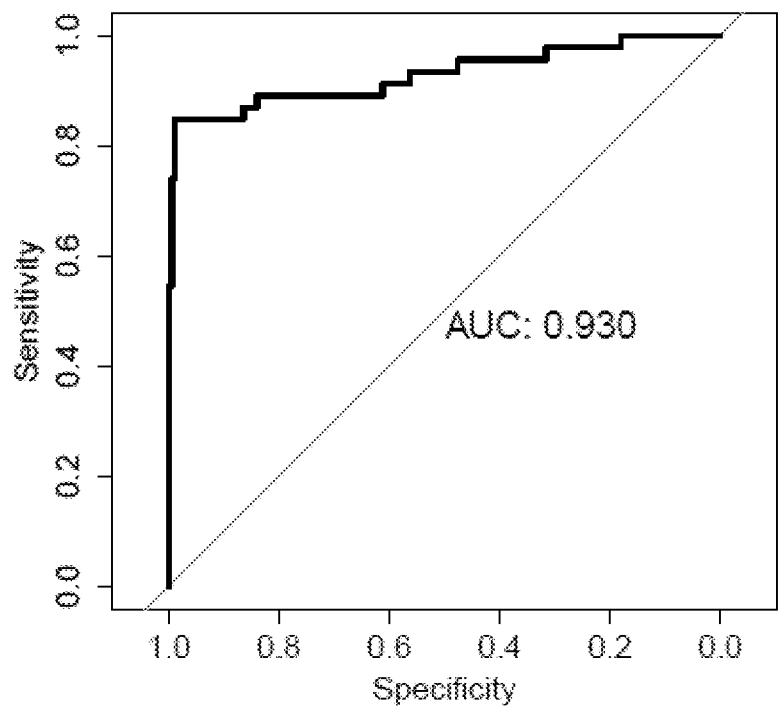

FIG. 10: Classification of PDAC Stage I-II vs. Healthy Controls

Classification of serum samples from patients with early stage (stage I/II) PDAC vs. healthy controls in the blinded validation. Data have been derived by multiplex microarray-based analysis in combination with CA19-9 assessment. The analysis yields a ROC AUC-value of 0.93 differentiating early stage PDAC samples (stages I/II; n=56) from the healthy controls (n=221).

Figure 11:
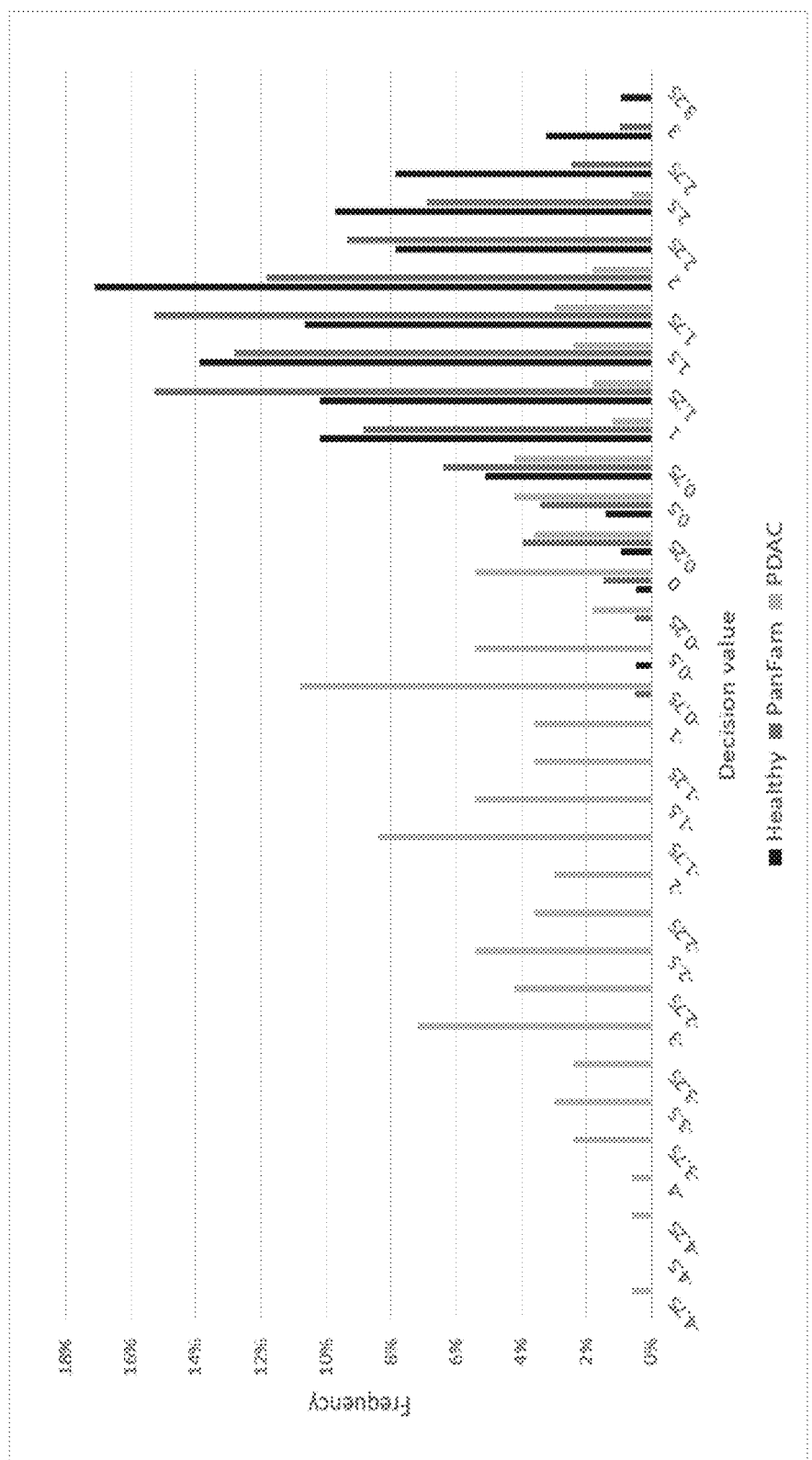

FIG. 11: Distribution of Mean Decision Values

Distribution of mean decision values for PDAC (all stages) samples, hereditary/FPC risk group samples (designated PanFam) and healthy controls, respectively, in the blinded validation. The plot shows the frequency of individuals from each of the three subgroups binned into decision values intervals of 0.25.

EMBODIMENT EXAMPLES

The invention may further be defined by the following embodiments:

1. A method for diagnosing or determining a pancreatic cancer-associated disease state comprising or consisting of the steps of:
   (a) providing a sample from an individual to be tested; and
   (b) measuring the presence and/or amount in the test sample of two or more biomarkers selected from the group defined in Table A;
   wherein the presence and/or amount in the test sample of the two or more biomarkers selected from the group defined in Table A is indicative of the pancreatic cancer-associated disease state in the individual.
2. The method according to item 1 wherein the pancreatic cancer-associated disease state is selected from the group consisting of:
   (i) diagnosis of pancreatic cancer;
   (ii) diagnosis of early pancreatic cancer 3. The method according to any one of the preceding items wherein the pancreatic cancer-associated disease state is early pancreatic cancer.
4. The method according to item 3 wherein the method is for the diagnosis of stage I or stage II pancreatic cancer.
5. The method according to any previous item wherein the method is for distinguishing an individual with a pancreatic cancer-associated disease state from an individual without pancreatic cancer but with symptoms suggestive or consistent with pancreatic cancer, optionally wherein the individual without pancreatic cancer has a benign pancreatic or biliary disease, e.g. acute and chronic pancreatitis, diabetes, liver disease, pancreatic cyst, gallstone disease and IgG4 disease.
6. The method according to any previous item wherein the sample in step (a) is from an individual in one or more of the following risk groups:
   (a) Individuals with a family history of pancreatic cancer or certain hereditary predispositions (e.g. Peutz-Jeghers syndrome);
   (b) Individuals diagnosed with diabetes (e.g. new-onset diabetes, in particular those aged 50 years or over); and/or
   (c) Individuals with symptoms suggestive or consistent with pancreatic cancer.
7. The method according to any previous item wherein the sample in step (a) is from an individual with a benign pancreatic or biliary disease, e.g. acute and chronic pancreatitis, diabetes, liver disease, pancreatic cyst, gallstone disease and IgG4 disease.
8. The method according to any one of the preceding items wherein step (b) comprises or consists of measuring the presence and/or amount of two or more biomarkers listed in Table A(i)-(vi), for example at least 3, 4, 5, 6, 7, 8, 9, 10, 11, or 12 of the biomarkers listed in Table A(i)-(vi).
9. The method according to any one of the preceding items wherein step (b) comprises or consists of measuring the presence and/or amount of six or more biomarkers listed in Table A, for example at least 7, 8, 9, 10, 11, 12 or 13 of the biomarkers listed in Table A.
10. The method according to any one of the preceding items wherein step (b) comprises or consists of measuring the presence and/or amount of three or more biomarkers listed in Table A(i)-(v), for example at least 4, 5, 6, 7, 8, or 9 of the biomarkers listed in Table A(i)-(v).
11. The method according to any one of the preceding items wherein step (b) comprises or consists of measuring the presence and/or amount of one or more biomarker(s) listed in Table A, part (i) and/or part (iii) and/or part (v).
12. The method according to any one of the preceding items wherein step (b) comprises or consists of measuring the presence and/or amount of: (i) OPG and/or VWF; and (ii) GSN and/or HADH2.
13. The method according to any one of the preceding items wherein step (b) comprises or consists of measuring the presence and/or amount of: (i) OPG and/or VWF; (ii) GSN and/or HADH2; and (iii) IGFBP3.
14. The method according to any one of the preceding items wherein step (b) comprises or consists of measuring the presence and/or amount of: (i) OPG and/or VWF; (ii) IGFBP3; and (iii) MUC16 and/or FCN2 and/or MASP2.
15. The method according to any one of the preceding items wherein step (b) comprises or consists of measuring the presence and/or amount of: (i) OPG and/or VWF; (ii) GSN and/or HADH2; (iii) IGFBP3, and (iv) Complement Factor B.
16. The method according to any one of the preceding items wherein step (b) comprises or consists of measuring the presence and/or amount of VWF, FCN2, and/or MASP2
17. The method according to any one of the preceding items wherein step (b) comprises or consists of measuring the presence and/or amount of two or more of the following biomarkers: (i) OPG and/or VWF; (ii) GSN and/or HADH2; (iii) IGFBP3; (iv) MUC16, FCN2, and/or MASP2.
18. The method according to any one of the preceding items wherein step (b) comprises or consists of measuring the presence and/or amount of: (i) OPG and/or VWF; (ii) GSN and/or HADH2; (iii) IGFBP3; (iv) Complement Factor B; (v) MUC16 and/or FCN2 and/or MASP2; (vi) Complement C4; (vii) Complement C5; and (viii) Cystatin C.
19. The method according to any one of the preceding items wherein step (b) comprises or consists of measuring the presence and/or amount of two or more of the following biomarkers and/or one or more secondary target(s) thereof: OPG, GSN, IGFBP3, Complement Factor B, MUC16, Complement C4, Complement C5, Cystatin C; optionally wherein the one or more secondary targets are selected from VWF, HADH2, FCN2, MASP2.
20. The method according to any one of the preceding items wherein step (b) comprises or consists of measuring the presence and/or amount of the following biomarkers: OPG, GSN, IGFBP3, Complement Factor B, MUC16, Complement C4, Complement C5, Cystatin C; and optionally including measuring the presence and/or amount of one or more biomarkers selected from VWF, HADH2, FCN2, MASP2.
21. The method according to any one of the preceding items wherein step (b) comprises measuring the presence and/or amount of CA 19-9.
22. The method according to any one of the preceding items wherein step (b) comprises or consists of measuring the presence and/or amount of: (i) OPG and/or VWF; (ii) GSN and/or HADH2; and (iii) CA 19-9.
23. The method according to any one of the preceding items wherein step (b) comprises or consists of measuring the presence and/or amount of: (i) OPG and/or VWF; (ii) GSN and/or HADH2; (iii) IGFBP3; and (iv) CA 19-9.
24. The method according to any one of the preceding items wherein step (b) comprises or consists of measuring the presence and/or amount of: (i) OPG and/or VWF; (ii) IGFBP3; (iii) MUC16, FCN2 and/or MASP2; and (iv) CA 19-9.
25. The method according to any one of the preceding items wherein step (b) comprises or consists of measuring the presence and/or amount of: (i) OPG and/or VWF; (ii) GSN and/or HADH2; (iii) IGFBP3; (iv) Complement Factor B; (v) MUC16, FCN2 and/or MASP2; (vi) Complement C4; (vii) Complement C5; (viii) Cystatin C; and (ix) CA 19-9.
26. The method according to any one of the preceding items wherein step (b) comprises measuring the presence and/or amount of one or more biomarker(s) listed in Table 1, for example 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the biomarkers in Table 1.
27. The method according to any one of the preceding items wherein step (b) comprises measuring the presence and/or amount of all of the biomarkers listed in Table A (e.g. at the protein, mRNA and/or ctDNA level).
28. The method according to any one of the preceding items further comprising or consisting of the steps of:

(c) providing one or more control samples from:
  i. an individual not afflicted with pancreatic cancer; and/or
  ii. an individual afflicted with a benign pancreatic and/or biliary disease; and
(d) determining a biomarker signature of the one or more control samples by measuring the presence and/or amount in the control sample of the one or more biomarkers measured in step (b);
wherein the pancreatic cancer-associated disease state is identified in the event that the presence and/or amount in the test sample of the one or more biomarkers measured in step (b) is different from the presence and/or amount in the control sample of the one or more biomarkers measured in step (d).

29. The method according to any one of the preceding items further comprising or consisting of the steps of:
  (e) providing one or more control samples from an individual afflicted with pancreatic cancer; and
  (f) determining a biomarker signature of the control sample by measuring the presence and/or amount in the control sample of the one or more biomarkers measured in step (b);
  wherein the pancreatic cancer-associated disease state is identified in the event that the presence and/or amount in the test sample of the one or more biomarkers measured in step (b) corresponds to the presence and/or amount in the control sample of the one or more biomarkers measured in step (f).

30. The method according to item 29 wherein the individual not afflicted with pancreatic cancer is a healthy individual.

31. The method according to items 29 or 30 wherein the one or more individual afflicted with pancreatic cancer is afflicted with a pancreatic cancer selected from the group consisting of adenocarcinoma (e.g., pancreatic ductal adenocarcinoma or tubular papillary pancreatic adenocarcinoma), pancreatic sarcoma, malignant serous cystadenoma, adenosquamous carcinoma, signet ring cell carcinoma, hepatoid carcinoma, colloid carcinoma, undifferentiated carcinoma, and undifferentiated carcinomas with osteoclast-like giant cells.

32. The method according to any one of the preceding items wherein the pancreatic cancer is pancreatic ductal adenocarcinoma.

33. The method according to any one of the preceding items wherein step (b) comprises measuring the expression of the protein or polypeptide of one or more biomarker(s).

34. The method according to item 33 wherein step (b), (d) and/or step (f) is performed using one or more first binding agent capable of binding to a biomarker protein or polypeptide listed in Table A.

35. The method according to item 34 wherein the one or more first binding agent comprises one or more of the antibody sequences defined in Table 5 and/or Table 6.

36. The method according to item 35 wherein the one or more first binding agent comprises one or more antibody sequences selected from the group consisting of: SEQ ID NO: 6, 11, 13, 15, 20, 30, 32, and 36.

37. The method according to item 35 wherein the one or more first binding agent comprises one or more of the antibody sequences SEQ ID NO: 30, 32, and 36.

38. The method according to any one of items 33-37 wherein the first binding agent comprises or consists of an antibody or an antigen-binding fragment thereof.

39. The method according to item 38 wherein the antibody or antigen-binding fragment thereof is a recombinant antibody or antigen-binding fragment thereof.

40. The method according to any one of items 35 to 38 wherein the antibody or antigen-binding fragment thereof is selected from the group consisting of: scFv; Fab; a binding domain of an immunoglobulin molecule.

41. The method according to any one of items 34 to 40 wherein the first binding agent is immobilised on a surface.

42. The method according to one of the preceding items wherein the one or more biomarkers in the test and/or control sample(s) are labelled with a detectable moiety.

43. The method according to item 42 wherein the detectable moiety is selected from the group consisting of: a fluorescent moiety; a luminescent moiety; a chemiluminescent moiety; a radioactive moiety; an enzymatic moiety.

44. The method according to item 42 or 43 wherein the detectable moiety is biotin.

45. The method according to any one of items 33 to 44 wherein step (b), (d) and/or step (f) is performed using an assay comprising a second binding agent capable of binding to the one or more biomarkers, the second binding agent comprising a detectable moiety.

46. The method according to item 45 wherein the second binding agent comprises or consists of an antibody or an antigen-binding fragment thereof.

47. The method according to item 46 wherein the antibody or antigen-binding fragment thereof is a recombinant antibody or antigen-binding fragment thereof.

48. The method according to item 46 or 47 wherein the antibody or antigen-binding fragment thereof is selected from the group consisting of: scFv; Fab; a binding domain of an immunoglobulin molecule.

49. The method according to any one of items 45 to 48 wherein the detectable moiety is selected from the group consisting of: a fluorescent moiety; a luminescent moiety; a chemiluminescent moiety; a radioactive moiety; an enzymatic moiety.

50. The method according to item 49 wherein the detectable moiety is fluorescent moiety (for example an Alexa Fluor dye, e.g. Alexa647).

51. The method according to any one of the preceding items wherein the method comprises or consists of an ELISA (Enzyme Linked Immunosorbent Assay).

52. The method according to any one of the preceding items wherein step (b), (d) and/or step (f) is performed using an array.

53. The method according to items 52 wherein the array is selected from the group consisting of: macroarray; microarray; nanoarray.

54. The method according to any one of the preceding items wherein the method comprises:
  (i) labelling biomarkers present in the sample with biotin;
  (ii) contacting the biotin-labelled proteins with an array comprising a plurality of scFv immobilised at discrete locations on its surface, the scFv having specificity for one or more of the proteins in Table A(i)-(vi);
  (iii) contacting the biotin-labelled proteins (immobilised on the scFv) with a streptavidin conjugate comprising a fluorescent dye; and
  (iv) detecting the presence of the dye at discrete locations on the array surface
  wherein the expression of the dye on the array surface is indicative of the expression of a biomarker from Table A in the sample.

55. The method according to any one of items 1 to 32 wherein step (b), (d) and/or (f) comprises measuring the expression of a nucleic acid molecule encoding the one or more biomarkers.

56. The method according to item 55, wherein measuring the expression of the one or more biomarker(s) in step (b), (d) and/or (f) is performed using one or more binding agent, each individually capable of binding selectively to a nucleic acid molecule encoding one of the biomarkers identified in Table A.
57. The method according to any one of the preceding items wherein the sample provided in step (a), (c) and/or (e) is selected from the group consisting of unfractionated blood, plasma, serum, tissue fluid, pancreatic tissue, milk, bile and urine.
58. The method according to item 57, wherein the sample provided in step (a), (c) and/or (e) is selected from the group consisting of unfractionated blood, plasma and serum.
59. The method according to item 57 or 58 wherein the sample provided in step (a), (c) and/or (e) is serum.
60. The method according to any one of the preceding items wherein the predictive accuracy of the method, as determined by an ROC AUC value, is at least 0.50, for example at least 0.55, 0.60, 0.65, 0.70, 0.75, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98 or at least 0.99.
61. The method according to item 60 wherein the predictive accuracy of the method, as determined by an ROC AUC value, is at least 0.83.
62. The method according to any one of the preceding items further comprising one or more further clinical investigations (such as testing a biopsy sample and/or in vivo imaging of the patient) in order to confirm or establish the diagnosis.
63. The method according to any one of the preceding items wherein, in the event that the individual is diagnosed with pancreatic cancer, the method comprises step (g) of providing the individual with a pancreatic cancer therapy.
64. The method according to item 63 wherein the pancreatic cancer therapy is selected from the group consisting of surgery, chemotherapy, radiotherapy, immunotherapy, chemoimmunotherapy, thermochemotherapy and combinations thereof.
65. The method according to item 63 or 64 wherein the pancreatic cancer therapy comprises or consists of surgical removal of the pancreas in whole or in part (for example, using the Whipple procedure to remove the pancreas head or a total pancreatectomy) combined with chemotherapy (for example, gemcitabine and/or 5-fluorouracil).
66. The method according to any previous item wherein measuring the presence and/or amount in the test sample of one or more biomarkers selected from the group defined in Table A in step (b) is replaced with measuring the presence and/or amount in the test sample of one or more protein bound by one or more of the antibody sequences described in Table 5.
67. An array for determining the presence of, or risk of having, pancreatic cancer in an individual comprising an agent or agents for detecting the presence in a protein and/or nucleic acid sample from the individual of one or more of the biomarkers defined in Table A.
68. The array according to item 67 wherein the agent or agents for detecting the presence in a sample of one or more of the biomarkers defined in Table A is/are one or more binding agents as defined in any one of items 34 to 44 or 56.
69. The array according to item 67 or 68 wherein the array comprises agents capable of binding to all of the biomarkers defined in Table A(i)-(vi); optionally wherein the array comprises agents capable of binding to all of the biomarkers defined in Table A.
70. The array according to item 67 or 68 wherein the array comprises agents capable of binding to the following biomarkers:
    (i) OPG and/or VWF; (ii) GSN and/or HADH2; (iii) IGFBP3; (iv) Complement Factor B; (v) MUC16, FCN2 and/or MASP2; (vi) Complement C4; (vii) Complement C5; and (viii) Cystatin C; optionally including one or more additional biomarkers from Table 1.
71. The array according to any one of items 67 to 70 wherein the array comprises antibodies, or antigen-binding fragments thereof, capable of binding to all of the biomarkers at the protein level.
72. The array according to any one of items 67 to 71 wherein the array comprises one or more of the antibodies identified in Table 5.
73. The array according any one of items 67 to 72 wherein the array comprises one or more of the antibodies in Table 6.
74. Use of two or more biomarkers selected from the group defined in Table A as biomarkers for determining the presence of, or risk of having, pancreatic cancer in an individual.
75. The use according to item 74 wherein the two or more biomarkers comprise the following biomarkers:
    (i) OPG and/or VWF; (ii) GSN and/or HADH2; (iii) IGFBP3; (iv) Complement Factor B; (v) MUC16, FCN2 and/or MASP2; (vi) Complement C4; (vii) Complement C5; and (viii) Cystatin C; optionally the use additionally including use of CA 19-9 and/or one or more additional biomarkers from Table 1.
76. The use according to item 74 or 75 wherein all of the biomarkers defined in Table A are used together as a diagnostic signature for determining the presence of pancreatic cancer in an individual.
77. A kit for determining the presence of, or risk of having, pancreatic cancer comprising:
    (a) an array according to any one of items 67 to 73, or components for making the same; and
    (b) instructions for performing the method as defined in any one of items 1 to 66.
78. A method of treating pancreatic cancer in an individual comprising the steps of:
    (a) diagnosing pancreatic cancer according to the method defined in any one of items 1 to 66; and
    (b) providing the individual with pancreatic cancer therapy.
79. The method according to item 78 wherein step (a) further comprises comprise one or more further clinical investigations (such as testing a biopsy sample and/or in vivo imaging of the patient) in order to confirm or establish the diagnosis.
80. The method according to item 78 or 79 wherein the pancreatic cancer therapy is selected from the group consisting of surgery (e.g., resection), chemotherapy, immunotherapy, chemoimmunotherapy and thermochemotherapy.
81. The method of any one of items 78 to 80 wherein the pancreatic cancer therapy comprises surgical removal of the pancreas in whole or in part (e.g. using the Whipple procedure to remove the pancreas head or a total pancreatectomy) combined with chemotherapy (e.g. gemcitabine and/or 5-fluorouracil).

82. A method or use for determining the presence of pancreatic cancer in an individual substantially as described herein.
83. An array or kit for determining the presence of pancreatic cancer in an individual substantially as described herein.

Example 1

Background

Pancreatic ductal adenocarcinoma (PDAC) is one of the most aggressive malignancies with a 5-year survival rate of less than 10%. Diffuse symptoms and lack of biomarkers for early detection often results in late-stage diagnosis and explains the high mortality rate. Biomarker panels that enable earlier PDAC detection would have great value in improving patient management and survival rate.

Methods

A recombinant antibody microarray platform was utilized to decipher a biomarker signature associated with PDAC. Initially, 396 single-chain variable fragments (scFvs) directed against 183 unique targets were assessed for their ability to discriminate PDAC from non-PDAC controls. Following data mining, 38 scFvs were selected to be included in a subsequent multicenter study. The 38-plex microarray was used to probe a serum sample set (n=1113) consisting of 315 PDAC (stage I-IV), 310 healthy controls and 488 symptomatic controls. Samples had been collected from patients and healthy volunteers at seven reference sites in USA and Europe.

Results

Biostatistical analysis of microarray data was used to derive a novel 8-plex biomarker signature for detection of early stage PDAC. When combined with a CA19-9 assay, the signature panel was able to detect early PDAC (stage I and II) versus all controls (healthy and symptomatic) with a ROC-AUC of 0.95.

Conclusion

A novel 8-plex biomarker signature adds significant orthogonal information to the established CA19-9 biomarker to allow detection of early stage PDAC with high predictive performance. This clearly points to the possibility of earlier diagnosis of pancreatic cancer and thereby an increased rate of surgically resectable tumors.

Abbreviations

AUC, Area under the curve; CV, Coefficient of variance; ELISA, enzyme linked immunosorbent assay; IP-MS, Immunoprecipitation mass spectrometry; LASSO, Least absolute shrinkage and selection operator; MWCO, Molecular weight cut-off; MT-PBS, PBS with 1% milk and 1% Tween®-20; PBS, Phosphate buffered saline; PDAC, Pancreatic ductal adenocarcinoma; RF, Random forest; ROC, Receiver operating characteristic; RT, Room temperature; scFv, Single-chain fragment variable; SVM, Support vector machine; T-PBS, PBS with 0.05% Tween®-20.

Introduction

In this multicenter case-control study, serum from PDAC stage I-IV patients were analyzed using Immunovia's IMMray™ recombinant antibody microarray platform, in combination with a CA19-9 assay, to identify a biomarker signature able to discriminate stage I/II pancreatic cancer from clinically relevant controls that are presenting at the secondary care with alarming symptoms overlapping early PDAC.

Patients may be symptomatic for at least 12 months before a diagnosis of pancreatic cancer is made (Haeno et al, 2012, Hippisley-Cox and Coupland, 2012 Stapley et al, 2012). A recent study from University College London (UCL) interrogated a large UK primary care database, The Health Improvement Network (THIN). This study showed that PDAC patients in average visited the general practitioner three times more often the year prior to diagnosis, with symptoms such as abdominal pain (39%), jaundice (36%), change in bowel habit (30%) or dyspepsia (21%) (Keane et al, 2014i, Keane et al, 2014ii). Currently, patients with suspected pancreatic cancer are investigated by numerous referral pathways with generally poor efficacy and outcomes.

By collecting and subsequently using symptomatic control samples that properly reflect the clinical population of concern, we aimed to maximize the clinical translatability of the results. Studies based solely on comparisons with healthy controls may lead to biomarker signatures that are non-specific to the disease of concern, and to sensitivity and specificity estimates that are unlikely to represent the performance of the test in the intended clinical setting.

Methods

Sample Collection

All serum samples were collected between 2016 and 2019 at seven pancreatic disease reference sites in USA and Europe. The sites contributing with samples in this study were: UCL Institute for Liver and Digestive Health, London UK; University of Pittsburgh, Division of Gastroenterology, Hepatology & Nutrition, Pittsburgh, USA; New York University Langone Health, Perlmutter Cancer Center, New York, USA; Beth Israel Deaconess Medical Center (BIDMC), Pancreas and Liver Institute, Boston, USA; Ramon y Cajal Institute for Health Research (IRYCIS), Madrid, Spain; Växjö Central Hospital, Department of Transfusion Medicine, Sweden and Hallands Hospital Varberg, Department of Transfusion Medicine, Sweden.

Demographics of Study Cohorts

The samples from UCL comprised 30 PDAC, 79 diabetic controls and 409 non-diabetic symptomatic controls. The samples from University of Pittsburgh comprised 169 PDAC and 15 healthy controls. The samples from IRYCIS comprised 44 PDAC and 50 healthy controls. 60 PDAC samples were from the Perlmutter Cancer Center and 12 PDAC samples were from BIDMC. Finally, 141 healthy controls were from the hospital in Växjö, 48 were from the hospital in Varberg and 56 from a commercial source (Folio Conversant).

The symptomatic control samples were collected from individuals having concerning symptoms suggestive of PDAC (e.g. abdominal pain and jaundice), but that were subsequently diagnosed with various benign pancreatic and biliary diseases, e.g. acute and chronic pancreatitis, liver disease, pancreatic cyst, gallstone disease and IgG4 disease.

CA19-9 Assay

Serum CA19-9 levels were determined using an enzyme linked immunosorbent assay (ELISA) kit (CanAg CA19-9 EIA, Fujirebio Diagnostics, Göteborg, Sweden). The level of CA19-9 were calculated by interpolation from a reference curve generated in the same assay with reference standards of known concentrations. All CA19-9 assays were performed in duplicate according to the manufacturer's instructions.

Sample Biotinylation

The serum samples were labeled with biotin. Briefly, the serum was diluted 1:9 in PBS to a total protein concentration of approximately 8 g/l and labeled with 1.1 mM EZ-Link NHS-PEG4-Biotin (Thermo Fisher Scientific). The solution was allowed to react for two hours at 4° C. and then quenched with the addition of 0.5M Tris-HCl, pH 8.0. The biotinylated serum samples were aliquoted and stored at −20° C. until further analysis.

Antibody Microarray Production

The antibody microarrays consisted of 38 human recombinant scFvs directed against 33 different antigens (Table 1).

The scFv antibodies have been selected from large phage display libraries using stringent screening and selection protocols, and are all based on a scaffold that has been shown to provide favourable antigen-binding properties and high on-chip functionality (Steinhauer et al., 2002, Säll et al., 2016). In addition, the specificity of selected antibodies has been validated using pure proteins, mixtures of pure proteins, as well as serum samples with i) known levels of the targeted analyte(s), ii) spiked with known level of specific protein(s), and/or iii) depleted of the targeted protein(s). Orthogonal methods such as mass spectrometry (affinity pull-down experiments), ELISA, Meso Scale Discovery (MSD) cytokine assay, cytometric bead assay, as well as spiking and blocking experiments, have also been utilized for assessing antibody specificities (Söderlind et al., 2000; Ingvarsson et al., 2007, Wingren and Borrebaeck, 2008, Borrebaeck and Wingren, 2011; Carlsson et al., 2011).

His-tagged scFvs were produced in the periplasm of *E. coli* and purified by immobilized metal ion affinity chromatography (IMAC) using His MultiTrap HP 96-well filter plates (GE Healthcare Life Science). The elution buffer was exchanged for PBS, using Zeba™ Spin desalting 96-well spin plates with 7K MWCO resins (Thermo Fisher Scientific). Protein concentration was estimated using a Pierce Coomassie (Bradford) protein assay kit (Thermo Fisher Scientific). Protein purity was assessed by SDS-PAGE using 8-16% Criterion TGX Stain-Free gels (Bio-Rad). Antibody microarrays were produced on black MaxiSorp slides (Nunc, Thermo Fisher Scientific), using a non-contact printer (sciFLEXARRAYER SX; Scienion). The array layout was printed using spot-on-the-fly option and with one PDC (glass piezo dispense capillary). 14 identical arrays were printed on each slide in two columns of seven arrays.

Each array consisted of 14×18 spots with 300 µm spot-to-spot center distance and a spot diameter of 140 µm. Each array consisted of six identical segments. All scFvs were printed in six spot replicates with one replicate in each segment. The on-chip scFv concentrations ranged from 40 to 193 µg/mL depending on binding properties of the individual clone. In addition, several spot positions were left empty as "negative reference spot control", and one reference marker (biotinylated BSA) were used to guide the automatic grid alignment process, but not for any quantitative purposes. Printed microarray slides were stored in dark in a climate-controlled room, at 22° C. and 40% relative humidity, for at least 5 days before being used in microarray assays.

Immunoprecipitation Mass Spectrometry (IP-MS)

In order to verify target binding of the scFv antibodies and to identify potential interacting proteins in serum, affinity pull-down assays were conducted. Briefly, purified histidine-tagged scFvs were immobilized onto magnetic nickel beads (MagneHis Ni-particles, Promega). Four technical replicates per antibody were used and non-coated beads were included as negative controls to subtract non-specific binding to the beads. The scFv coated and control beads were incubated for 20 min with pooled normal human serum (diluted 14-fold in PBS). The beads were washed three times to attenuate non-specific binding.

Captured proteins were eluted from the beads and digested with trypsin over night at 37° C. Trypsin activity was quenched by addition of formic acid and digested samples were dried down in a speed-vac. Dried peptides were cleaned using UltraMicroSpin C18 columns (Nest Group) and re-suspended in 0.1% formic acid for LC-MS/MS analysis.

The peptide pool was analyzed using a Q-Exactive HF-X mass spectrometer coupled to a nanoLC system (Thermo Fisher Scientific). The Xcalibur software v. 3.0 was used to control and acquire the data from Q-Exactive HF-X. Peptide identification of obtained data was carried out using Mascot Server (v. 2.4.1) for searches against the THISP2 database (peptideatlas.org/thisp/), and quantification of peptides at the MS1 level using Dinosaur, through the Proteios Software Environment (proteios.org).

Focusing on the resulting biomarker signature, the affinity pull-down assays identified potential secondary targets for three scFvs (Table 3). Interacting proteins can either be the result of off-target binding by the antibody (direct co-enrichment) or due to interaction of the intended target with another protein (indirect co-enrichment) (Fredolini et al., 2019). Hence, the von Willebrand factor (VWF) was captured by the scFv directed against osteoprotegerin (OPG). It has been reported that OPG is able to form a complex with VWF (Shahbazi et al., 2007), which points to the indirect route of co-enrichment. Moreover, the scFv antibody initially directed against HADH2 was shown to bind gelsolin (GSN) and the scFv antibody directed against MUC16 (CA125) to tentatively bind the complement lectin pathway components, ficolin-2 (L-ficolin; FCN2) and mannan-binding lectin serine protease 2 (MASP2).

Microarray Assay

In general, 12 patient samples were analyzed on each microarray slide. The positioning of the samples was randomized but the distribution of PDAC and control samples was approximately the same across slides and runs. Apart from disease status, samples were also stratified based on sub-group (e.g. stage or w/wo diabetes), gender, age group, cohort and collection year. Two arrays on each slide were used for a control sample (pool of serum from healthy individuals) for slide normalization purposes. On each assay run, two microarray slides were dedicated for quality control (QC) purposes.

Each microarray slide was mounted in a hybridization gasket (Schott) and blocked with 1% w/v milk, 1% v/v Tween-20 in sterile PBS (MT-PBS) at RT for 2 hours with constant agitation. Meanwhile, aliquots of labelled serum samples were thawed on ice and subsequently diluted 1:50 in MT-PBS. The slides were washed four times with 0.05% Tween-20 in sterile PBS (T-PBS) followed by addition of diluted serum samples to the wells of the gasket.

Samples were incubated on the slides at RT for 2 hours with constant agitation. Next, the slides were washed four times with T-PBS, incubated with 1 µg/ml Streptavidin Alexa-647 (Life Technologies) in MT-PBS at RT for 1 hour with constant agitation, and again washed four times with T-PBS. Finally, the slides were dismounted from the hybridization gaskets, immersed in dH$_2$O and dried under a stream of N$_2$. The slides were immediately scanned with a microarray fluorescence scanner, InnoScan 710 AL (Innopsys), at a laser excitation wavelength of 635 nm using a resolution of 10 µm/pixel.

Data Acquisition, Quality Control, and Pre-Processing

Grid alignment and spot signal quantitation were performed using our in-house, proprietary software platform, Immunovia Evaluation System (IES). Spot signal intensities were quantified using the fixed circle method.

Each data point represented the median, background-subtracted, signal of six replicate spots unless any replicate(s) did not pass the applied z-filtering acceptance criteria and were flagged as position failures. In this case, the worst performing replicate(s) was eliminated and the median value of the remaining replicates was used instead. Log 2 values of signal intensities were used, and no imputation was applied on the data.

In the next step, data was normalized. Using our normalization approach, slide-to-slide variation was handled by calculating normalization factors for each microarray slide, per each antibody. This factor was based on the signals for the technical replicate (serum pool from healthy individuals) applied to the same positions on each slide across the study.

All computations were done with R environment (R Core Team (2019). R: A language and environment for statistical computing. R Foundation for Statistical Computing, Vienna, Austria). Following data normalization, outlier detection/removal was performed through the arrayQualityMetrics R package (Kauffmann et al., 2009; Kauffmann and Huber, 2010), which computes the Kolmogorov-Smirnov statistic between each array's intensity distribution and the distribution of the pooled data. Finally, we added ELISA data for CA19-9 (also log 2 transformed) into the dataset prior to data analysis.

All-in-all, samples from 36 donors were removed during quality control and pre-processing, and the final data set contained data from 1113 individuals.

Data Analysis

Of note, the 38 scFv-based microarray used in this study was derived from preceding discovery runs comprising 396 scFv antibodies (Table 2). To this end, data was partitioned into a training (50%) and a test set (50%). A feature selection step was then conducted on the training set and the predictive performance of the selected biomarkers was evaluated using only the test set (data not shown).

By this means, we identified 38 scFv antibodies (directed against 33 unique proteins) as candidate probes for detection of PDAC. In the current study the aim was to verify the usefulness of these scFvs by using several novel independent sample cohorts, and to attempt to condense the list of protein biomarkers further. To this end, we focused on three main criteria for assessing the candidate scFvs for the intended use. These three main categories were (i) difference of relative expression (fold change) between cases and controls (ii) prediction performance and (iii) analytical performance and robustness. This has been done on a pre-defined fraction of data.

Hence, we firstly assessed each scFv antibody with respect to strength and direction of fold change (FC). FC for a given antibody is the difference between the average, log 2-transformed, values of two groups (i.e. PDAC and controls). Secondly, the prediction performance of the scFv antibodies was evaluated using the variable importance returned by the Random Forest (RF) and Least Absolute Shrinkage and Selection Operator (LASSO) algorithms, applying multivariate and dependent feature selection. In the third step, we assessed each scFv antibody in terms of variability (expressed as microarray inter- and intra-assay CV values) in order to select probes displaying robust analytical performance. In addition, to decipher an optimally condensed biomarker signature, scFvs showing high level of correlation to other antibodies were removed to minimize redundancy.

Subsequently, the classification performance of the resulting biomarker signature was assessed using support vector machine algorithm (SVM) and results was evaluated by generating receiver operating characteristic (ROC) curves for various group comparisons (e.g. PDAC vs. healthy controls), and the corresponding area under the curve (AUC) values were calculated. When building the classification model, data was divided into a training set including 70% of the samples and a test set including 30% of the samples. A large number of cross validations were performed and ROC AUC, sensitivity and specificity values were calculated for each potential model. The predictive performance of the model was evaluated for different subsets of the biomarkers and both with and without CA19-9 added to the signature (Table 4).

Results

Recombinant antibody microarrays are based on immobilized antibody derivatives for parallel analysis of multiple analytes in a minute amount of liquid biopsy (usually serum or plasma). The current study was based on antibody microarrays comprising 38 single-chain variable fragments (scFvs) directed against 33 different antigens (Table 1). These 38 scFvs had been selected from a repertoire of 396 scFvs (Table 2) by preceding discovery studies as described in the Method section (data not shown). As mentioned previously, all scFv antibodies included in this study are built on a scaffold that has been shown to display appropriate adsorption properties and high functional stability when kept in a dried-out state on the microarray slide (Steinhauer et al., 2002, Säll et al., 2016).

Using 1113 serum samples from several different sites in USA and Europe, this study represents to the best of our knowledge one of the largest multicenter analysis of biomarker panels for predicting pancreatic cancer that has been conducted so far. In addition, this study differs from previous affinity proteomic studies on pancreatic cancer (e.g. Wingren et al., 2012, Gerdtsson et al., 2015, Mellby et al., 2018) in two important aspects. Firstly, the study is based on a reduced, 38-plex, microarray consisting entirely of informative probes rather than a high-density microarray, and secondly, the sample set used in this study included a large number (n=488) of symptomatic controls carefully selected to represent the intended clinical use population of the test.

Figure 1:
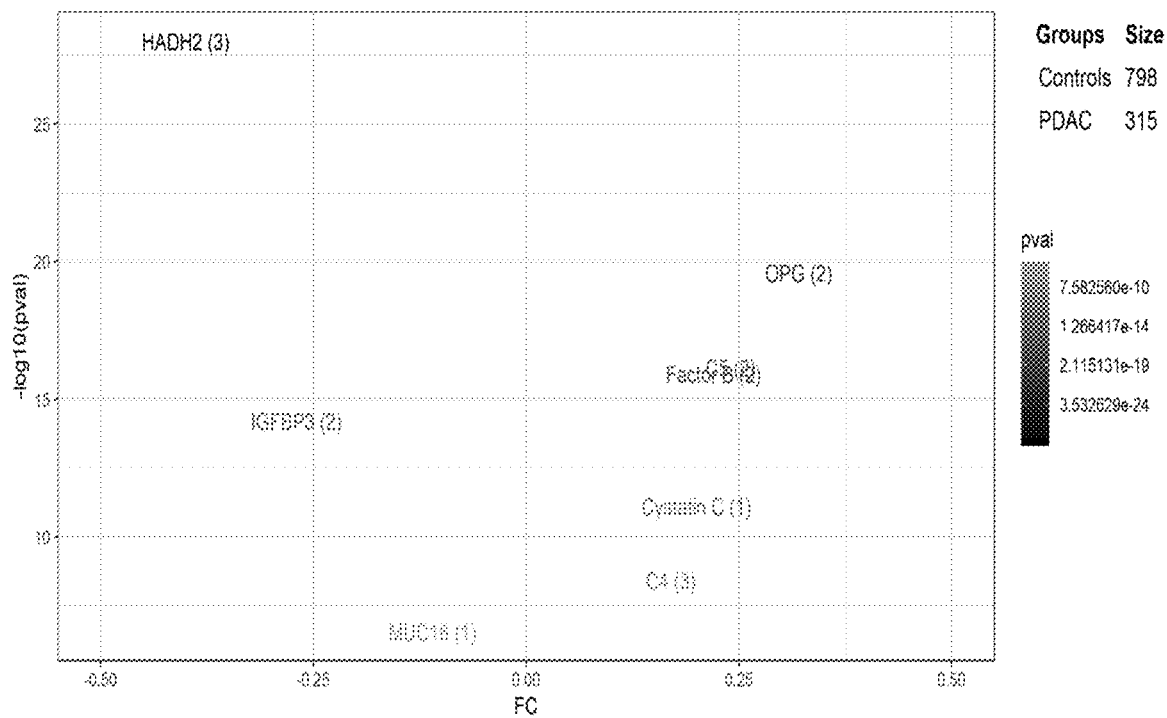
FIG. 1: Volcano Plot for the 8-Plex Biomarker Signature

The generated microarray data allowed us to condense the biomarker signature down to eight unique proteins (Table 3). As described in detail in the Method section, this was done by assessing FC values, prediction performance and analytical variability of individual scFv antibodies. FIG. 1 shows a volcano plot of the entire data set (PDAC vs all controls) for the corresponding scFv antibody clones.

The classification performance of the derived 8-plex signature was evaluated by generating ROC curves for various group comparisons and the corresponding AUC values were calculated. FIG. 2-4 shows ROC curves for classifications of PDAC vs. healthy controls, PDAC vs. symptomatic controls and PDAC vs all controls, respectively. When combining the 8-plex microarray signature with data from the CA19-9 assay, AUC values of 0.96, 0.93 and 0.94 were achieved.

Most importantly, an ROC-AUC value of 0.95 was calculated for the discrimination of samples from patients with early PDAC (stage I/II) versus all controls (healthy and symptomatic) when using the combination of the 8-plex signature with data from the CA19-9 assay (FIG. 5).

Since differential diagnosis of early PDAC vs. pancreatitis can be particularly challenging (Klöppel and Adsay, 2009), we proceeded to test the classification ability of our biomarker signature with regard to this subgroup analysis. Even though the number of chronic pancreatitis samples was limited in the current study (n=56), our data suggest that chronic pancreatitis can be discriminated from early stage I/II PDAC with a ROC-AUC of 0.92 (FIG. 6).

Discussion

In this study, we have shown that a recombinant antibody microarray-based biomarker signature of eight proteins can significantly improve upon the predictive performance of serum CA19-9 analysis as well as enhance the discrimination between PDAC and various benign diseases overlapping in symptoms with early PDAC. Importantly, we could demonstrate that by combining proteomic multiplex analysis with a CA19-9 ELISA, early stage I/II PDAC patient samples could be separated from all controls with a ROC-AUC of 0.95. It should be stressed that these results have been achieved using collected serum samples (n=1113) from seven different pancreatic disease reference sites in USA and Europe to avoid a number of potential biases from sample collection, processing, and storage that can occur when using archival specimens (Zhang and Chan, 2005).

The sialyl Lewis A tetrasaccharide epitope (carbohydrate antigen 19-9; CA19-9) is the most widely clinically used tumor marker for pancreatic cancer, but alone it lacks the necessary sensitivity and specificity for diagnosis and is not recommended for screening purposes. When using an assay cut-off value of 37 U/mL, CA19-9 has been reported to have a median sensitivity of 81% and specificity of 90% for pancreatic cancer, whereas increasing the threshold to 100 U/mL improves specificity to 98% but reduces sensitivity to 68% (Steinberg, 1990). However, later it has been pointed out that the cited analysis mainly involved healthy subjects as controls and therefore does not reflect the clinical population of concern (Poruk et al., 2013). When the accuracy of CA19-9 was re-evaluated in a clinically more relevant context, the apparent functional sensitivity and specificity for CA19-9 was approximately 80% each at the conventional clinical cut-off of 37 U/ml.

By combining CA19-9 measurements with multiparametric microarray analysis, we could generate a SVM model algorithm that yields a specificity of 95% and a sensitivity of 83% discriminating PDAC samples from clinically relevant controls. Since CA19-9 is increased in a number of benign diseases (including pancreatitis, cirrhosis, cholangitis and obstructive jaundice), the use of relevant controls is instrumental for evaluating the clinical usefulness of potential PDAC biomarkers. In this context, we could demonstrate that stage I and II PDAC samples could be discriminated from chronic pancreatitis with a ROC-AUC of 0.92 (FIG. 6). Moreover, we observed that the composite signature increased the ROC-AUC value by approximately 5% when separating PDAC from symptomatic controls, as compared to using CA19-9 alone.

We see a great applicability of the SVM model algorithm as an aid for early detection of developing pancreatic cancers in patient groups with higher prevalence of the disease. These high-risk groups could include (i) individuals with a family history of pancreatic cancer or certain hereditary predispositions (Singhi et al., 2019); (ii) late onset diabetic patients over the age of 50 years, who have up to eight times increased risk for acquiring PDAC within the first three years of diabetes (Chari et al., 2005, Batabyal et al., 2014), and (iii) patients with vague but alarming symptoms potentially suggestive of pancreatic cancer, such as back and abdominal pain, jaundice and weight loss (Keane et al., 2014i).

Taken together, a diagnostic test for PDAC in high-risk patient groups holds the potential for earlier detection of malignancy, which significantly could contribute to increased tumor resectability and thereby an overall reduction in cancer-specific mortality (Pelaez-Luna et al., 2007).

As previously mentioned, the microarray-based biomarker signature yielding the highest specificity/sensitivity combination is directed against eight different proteins (Table 3). Three of these proteins, i.e. GSN, IGFBP3 and OPG, have previously been reported to be implicated in pancreatic cancer (Ni et al., 2008, Yoneyama et al., 2016, Shi et al., 2014). We observed an increased expression level of OPG, but reduced levels of GSN and IGFBP3, in PDAC serum samples (FIG. 1). This appears to be in accordance with the general literature on the topic. However, different antibodies might recognize distinct forms of circulating analytes (i.e. free, complex and fragmented), so conflicting results would not necessarily be unexpected.

The serum levels of MUC16 (CA125) is a classical tumor marker used in ovarian cancer for diagnosis, detection of early recurrence, and for monitoring of the therapeutic effects of treatments (Felder et al., 2014). Reports about the involvement of MUC16 in pancreatic cancer are much scarcer. However, MUC16 seems to have a diagnostic value in cases of pancreatic cancer where CA19-9 is not elevated, particularly in those patients who are negative for the Lewis antigen (Liu et al., 2016).

The presence of several complement proteins (e.g. C4, C5 and Factor B) in the signature points to an important role of the complement system in pancreatic cancer. Cancer related information in the literature of complement is relatively sparse, but the involvement of complement in pancreatic diseases has been recognized (Bettac et al., 2017). Although inherently complex, complement activation is generally considered protective against cancer. The possible involvement FCN2 and MASP2 in the signature suggest a novel role for the lectin induced pathway in PDAC. FCN2 has previously been shown to directly associate with MASP2 to trigger the lectin complement pathway (Lacroix et al., 2009).

Finally, we observed increased serum levels of VWF and Cystatin C in PDAC samples (FIG. 1). VWF plays a major role in blood coagulation, and it seems plausible that it could be involved in the issue of venous thromboembolism (VTE) that affects a large percentage of PDAC patients (Faille et al., 2018). Cystatin C is an inhibitor of the cysteine proteinase, cathepsin B, and is an established clinical marker for estimating glomerular filtration rate (Ferguson et al., 2015). However, Cystatin C has previously also been implicated in cancer and was identified as a candidate marker of PDAC in a global proteome analysis of pancreatic juice samples (Kos et al., 2000, Grønborg et al., 2004). However, there has not previously been any suggestion to use the measurement of such biomarkers in combination to produce a signature for diagnosis of pancreatic cancer.

In summary, our results demonstrate that combining data from an 8-plex recombinant antibody microarray test with that of a CA19-9 assay can detect samples derived from patients with stage I and II PDAC with high predictive performance. Hence, this clearly points to the possibility of diagnosing pancreatic cancer at an earlier stage, using a serum biomarker signature.

We envision that this test regimen can be made readily available for clinicians in primary and secondary care for surveillance of high-risk populations and for diagnosis of patients with symptoms suggestive of early pancreatic cancer.

References

Ballehaninna U K and Chamberlain R S (2011) Serum CA 19-9 as a biomarker for pancreatic cancer—A comprehensive review. Indian J Surg Oncol. 2(2):88-100.

Bettac L, Denk S, Seufferlein T and Huber-Lang M (2017) Complement in pancreatic disease—perpetrator or savior? *Front Immunol.* 8:15.

Batabyal P, Vander Hoorn S, Christophi C and Nikfarjam M (2014) Association of diabetes mellitus and pancreatic adenocarcinoma: a meta-analysis of 88 studies. *Ann Surg Oncol.* 21(7):2453-2462.

Borrebaeck C A and Wingren C (2011) Recombinant antibodies for the generation of antibody arrays. *Methods Mol Biol.* 785:247-262.

Carlsson A, Wuttge D M, Ingvarsson J, Bengtsson A A, Sturfelt G, Borrebaeck C A and Wingren C (2011) Serum protein profiling of systemic lupus erythematosus and systemic sclerosis using recombinant antibody microarrays. 2011 10(5):M110.005033.

Chari S T, Leibson C L, Rabe K G, Ransom J, de Andrade M and Petersen G M (2005) Probability of pancreatic cancer following diabetes: A population-based study. *Gastroenterology* 129(2):504-511.

Conlon K C, Klimstra D S and Brennan M F (1996) Long-term survival after curative resection for pancreatic ductal adenocarcinoma. Clinicopathologic analysis of 5-year survivors. *Ann Surg.* 223(3):273-279.

Faille D, Bourrienne M C, de Raucourt E, de Chaisemartin L, Granger V, Lacroix R, Panicot-Dubois L, Hammel P, Lévy P, Ruszniewski P, Ajzenberg N and Rebours V (2018) Biomarkers for the risk of thrombosis in pancreatic adenocarcinoma are related to cancer process. *Oncotarget* 9(41):26453-26465.

Felder M, Kapur A, Gonzalez-Bosquet J, Horibata S, Heintz J, Albrecht R, Fass L, Kaur J, Hu K, Shojaei H, Whelan R J and Patankar M S (2014) MUC16 (CA125): Tumor biomarker to cancer therapy, a work in progress. *Mol Cancer* 13:129.

Ferguson T W, Komenda P and Tangri N (2015) Cystatin C as a biomarker for estimating glomerular filtration rate. *Curr Opin Nephrol Hypertens.* 24(3):295-300.

Fredolini C, Byström S, Sanchez-Rivera L, Ioannou M, Tamburro D, Pontén F, Branca R M, Nilsson P, Lehtiö J and Schwenk J M (2019) Systematic assessment of antibody selectivity in plasma based on a resource of enrichment profiles. *Sci Rep.* 9(1):8324.

Gerdtsson A S, Malats N, Säll A, Real F X, Porta M, Skoog P, Persson H, Wingren C and Borrebaeck C A (2015) A multicenter trial defining a serum protein signature associated with pancreatic ductal adenocarcinoma. *Int J Proteomics* 2015:587250.

Grønborg M, Bunkenborg J, Kristiansen T Z, Jensen O N, Yeo C J, Hruban R H, Maitra A, Goggins M G and Pandey A (2004) Comprehensive proteomic analysis of human pancreatic juice. *J Proteome Res.* 3(5):1042-1055.

Haeno H, Gonen M, Davis M B, Herman J M, Iacobuzio-Donahue C A and Michor F (2012) Computational modeling of pancreatic cancer reveals kinetics of metastasis suggesting optimum treatment strategies. *Cell* 148(1-2): 362-375.

Hippisley-Cox J and Coupland C (2012) Identifying patients with suspected pancreatic cancer in primary care: derivation and validation of an algorithm. *Br J Gen Pract.* 62(594):e38-e45.

Ilic M and Ilic I (2016) Epidemiology of Pancreatic Cancer. *World J Gastroenterol.* 22(44):9694-9705.

Ingvarsson J, Larsson A, Sjöholm A G, Truedsson L, Jansson B, Borrebaeck C A and Wingren C (2007) Design of recombinant antibody microarrays for serum protein profiling: Targeting of complement proteins. *J Proteome Res.* 6(9):3527-3536.

Kauffmann A, Gentleman R and Huber W (2009) arrayQualityMetrics—a bioconductor package for quality assessment of microarray data. *Bioinformatics* 25(3):415-416.

Kauffmann A and Huber W (2010) Microarray data quality control improves the detection of differentially expressed genes. *Genomics* 295:138-142.

Kenner B J, Chari S T, Maitra A, Srivastava S, Cleeter D F, Go V L, Rothschild L J and Goldberg A E (2016) Early detection of pancreatic cancer—a defined future using lessons from other cancers. *Pancreas* 45(8):1073-1079.

Kos J, Werle B, Lah T and Brünner N (2000) Cysteine proteinases and their inhibitors in extracellular fluids: Markers for diagnosis and prognosis in cancer. *Int J Biol Markers* 15:84-89.

Keane M G, Horsfall L, Rait G and Pereira S P (2014i) A case-control study comparing the incidence of early symptoms in pancreatic and biliary tract cancer. *BMJ Open* 4(11):e005720.

Keane M G, Horsfall L, Rait G and Pereira S P (2014ii) Sociodemographic trends in the incidence of pancreatic and biliary tract cancer in UK primary care. *PLoS One* 9(9):e108498.

Klöppel G and Adsay N V (2009) Chronic pancreatitis and the differential diagnosis versus pancreatic cancer. *Arch Pathol Lab Med.* 133(3):382-387.

Lacroix M, Dumestre-Pérard C, Schoehn G, Houen G, Cesbron J Y, Arlaud G J, and Thielens N M (2009) Residue Lys57 in the collagen-like region of human L-ficolin and its counterpart Lys47 in H-ficolin play a key role in the interaction with the mannan-binding lectin-associated serine proteases and the collectin receptor calreticulin. *J Immunol.* 182(1):456-465

Liu L, Xiang J, Chen R, Fu D, Hong D, Hao J, Li Y, Li J, Li S, Mou Y, Mai G, Ni Q, Peng L, Qin R, Qian H, Shao C, Sun B, Sun Y, Tao M, Tian B, Wang H, Wang J, Wang L, Wang W, Wang W, Zhang J, Zhao G, Zhou J and Yu X (2016) The clinical utility of CA125/MUC16 in pancreatic cancer: A consensus of diagnostic, prognostic and predictive updates by the Chinese study group for pancreatic cancer (CSPAC). *Int J Oncol.* 48(3):900-907.

McGuigan A, Kelly P, Turkington R C, Jones C, Coleman H G and McCain R S (2018) Pancreatic Cancer: A Review of Clinical Diagnosis, Epidemiology, Treatment and Outcomes. *World J Gastroenterol.* 24(43):4846-4861.

Mellby L D, Nyberg A P, Johansen J S, Wingren C, Nordestgaard B G, Bojesen S E, Mitchell B L, Sheppard B C, Sears R C and Borrebaeck C A K (2018) Serum biomarker signature-based liquid biopsy for diagnosis of early-stage pancreatic cancer. *J Clin Oncol.* 36(28):2887-2894.

Ni, X-G, Zhou L, Wang, G-Q, Liu, S-M, Bai X-F, Liu F, Peppelenbosch M, Zhao P (2008) The ubiquitin-proteasome pathway mediates gelsolin protein downregulation in pancreatic cancer. *Mol Med.* 14(9-10):582-589.

Orth M, Metzger P, Gerum S, Mayerle J, Schneider G, Belka C, Schnurr M and Lauber K (2019) Pancreatic ductal adenocarcinoma: Biological hallmarks, current status, and future perspectives of combined modality treatment approaches. *Radiat Oncol.* 14(1):141.

Pelaez-Luna M, Takahashi N, Fletcher J G and Chari S T (2007) Resectability of presymptomatic pancreatic cancer and its relationship to onset of diabetes: a retrospective review of CT scans and fasting glucose values prior to diagnosis. *Am J Gastroenterol.* 102(10):2157-2163.

Poruk K E, Gay D Z, Brown K, Mulvihill J D, Boucher K M, Scaife C L, Firpo M A and Mulvihill S J (2013) The clinical utility of CA 19-9 in pancreatic adenocarcinoma: Diagnostic and prognostic updates. *Curr Mol Med.* 13(3): 340-351.

Rawla P, Sunkara T and Gaduputi V (2019) Epidemiology of pancreatic cancer: Global trends, etiology and risk factors. *World J Oncol.* 10(1):10-27

Shahbazi S, Lenting P J, Fribourg C, Terraube V, Denis C V and Christophe O D (2007) Characterization of the interaction between von Willebrand factor and osteoprotegerin. *J Thromb Haemost.* 5(9):1956-1962.

Shi W, Qiu W, Wang W, Zhou X, Zhong X, Tian G and Deng A (2014) Osteoprotegerin is upregulated in pancreatic cancers and correlates with cancer-associated new-onset diabetes. *BioScience Trends* 8(6):322-326.

Shimizu Y, Yasui K, Matsueda K, Yanagisawa A and Yamao K (2005) Small carcinoma of the pancreas is curable: new computed tomography finding, pathological study and postoperative results from a single institute. *J Gastroenterol Hepatol.* 20(10):1591-1594.

Singhi A D, Koay E J, Chari S T and Maitra A (2019) Early detection of pancreatic cancer: Opportunities and challenges. *Gastroenterology* 156(7):2024-2040.

Sohn T A, Yeo C J, Cameron J L, Koniaris L, Kaushal S, Abrams R A, Sauter P K, Coleman J, Hruban R H and Lillemoe K D (2000) Resected adenocarcinoma of the pancreas-616 patients: results, outcomes, and prognostic indicators. *J Gastrointest Surg.* 4(6):567-579.

Stapley S, Peters T J, Neal R D, Rose P W, Walter F M and Hamilton W (2012) The risk of pancreatic cancer in symptomatic patients in primary care: a large case-control study using electronic records. *Br J Cancer* 106(12): 1940-1944.

Steinberg W (1990) The clinical utility of the CA 19-9 tumor-associated antigen. *Am J Gastroenterol.* 85(4):350-355.

Steinhauer C, Wingren C, Malmborg Hager A-C and Borrebaeck C A (2002) Single framework recombinant antibody fragments designed for protein chip applications. *BioTechniques* Suppl:38-45.

Säll A, Walle M, Wingren C, Müller S, Nyman T, Vala A, Ohlin M, Borrebaeck C A K and Persson H (2016) Generation and analyses of human synthetic antibody libraries and their application for protein microarrays. *Protein Eng Des Sel.* 29(10):427-437.

Söderlind E, Strandberg L, Jirholt P, Kobayashi N, Alexeiva V, Åberg A-M, Nilsson A, Jansson B, Ohlin M, Wingren C, Danielsson L, Carlsson R and Borrebaeck C A (2000) Recombining germline-derived CDR sequences for creating diverse single-framework antibody libraries. *Nat Biotechnol.* 18:852-856.

Wingren C and Borrebaeck C A (2008) Antibody microarray analysis of directly labelled complex proteomes. *Curr Opin Biotechnol.* 19(1):55-61.

Wingren C, Sandström A, Segersvärd R, Carlsson A, Andersson R, Löhr M and Borrebaeck C A. (2012) Identification of serum biomarker signatures associated with pancreatic cancer. *Cancer Res.* 72(10):2481-2490.

Yoneyama T, Ohtsuki S, Honda K, Kobayashi M, Iwasaki M, Uchida Y, Okusaka T, Nakamori S, Shimahara M, Ueno T, Tsuchida A, Sata N, Ioka T, Yasunami Y, Kosuge T, Kaneda T, Kato T, Yagihara K, Fujita S, Huang W, Yamada T, Tachikawa M and Terasaki T (2016) Identification of IGFBP2 and IGFBP3 as compensatory biomarkers for CA19-9 in early-stage pancreatic cancer using a combination of antibody-based and LC-MS/MS-based proteomics. *PLoS One* 11(8):e0161009.

Zhang Z and Chan D W (2005) Cancer Proteomics: In pursuit of "true" biomarker discovery. *Cancer Epidemiol Biomarkers Prev.* 14(10): 2283-2286.

TABLE 1

38-plex microarray scFvs

| scFv clone | Antigen/Biomarker | Exemplary SEQ ID NO. |
|---|---|---|
| TGF-β1 (1) | TGF-β1 | 1 |
| IFN-γ (2) | IFN-γ | 2 |
| PSA | PSA | 3 |
| C3 (1) | C3 | 4 |
| C3 (2) | C3 | 5 |
| C5 (2) | C5 | 6 |
| C1 inh. (1) | C1 esterase inhibitor | 7 |
| Properdin | Properdin | 8 |
| VEGF (3) | VEGF | 9 |
| CD40 (1) | CD40 | 10 |
| Cystatin C (1) | Cystatin C | 11 |
| Apo-A1 (3) | Apolipoprotein A1 | 12 |
| Factor B (2) | Factor B | 13 |
| Factor B (4) | Factor B | 14 |
| C4 (3) | C4 | 15 |
| C3 (3) | C3 | 16 |
| MYOM2 (1) | MYOM2 | 17 |
| CHX10 (3) | CHX10 | 18 |
| BTK (3) | BTK | 19 |
| HADH2 (3) | HADH2/GSN | 20 |
| MATK (1) | MATK | 21 |
| TNFRSF3 (2) | TNFRSF3 | 22 |
| UBC9 (3) | UBC9 | 23 |
| UBP7 (1) | UBP7 | 24 |
| UBP7 (2) | UBP7 | 25 |
| APLF (2) | APLF | 26 |
| MARK1-1 (1) | MARK1-1 | 27 |
| PTPPRN2 (1) | PTPRN2 | 28 |
| CEACAM5 (1) | CEACAM-5 | 29 |
| MUC16 (1) | MUC16 | 30 |
| MMP9 (2) | MMP9 | 31 |
| IGFBP3 (2) | IGFBP3 | 32 |
| IL-2ra (3) | IL-2Ra | 33 |
| AGR2 (1) | AGR2 | 34 |
| IGFBP2 (1) | IGFBP2 | 35 |
| OPG (2) | OPG | 36 |
| GDF-15 (1) | GDF-15 | 37 |
| CEACAM5 (3) | CEACAM-5 | 38 |

TABLE 2

Discovery phase scFv specificities; n = 396

| Antigen/Biomarker | Full name | No. of scFvs |
|---|---|---|
| AGAP-2 | Arf-GAP with GTPase, ANK repeat and PH domain-containing protein 2 | 3 |
| AGR2 | Anterior gradient protein 2 homolog | 1 |
| AGR3 | Anterior gradient protein 3 | 1 |
| AKT3 | RAC-gamma serine/threonine-protein kinase | 2 |
| Angiomotin | Angiomotin | 2 |
| ANM5 | Protein arginine N-methyltransferase 5 | 2 |
| APLF | Apataxin and PNK-like factor | 2 |
| APOA1 | Apolipoprotein A1 | 3 |
| APOA4 | Apolipoprotein A4 | 3 |
| ARHGC | Rho guanine nucleotide exchange factor 12 | 1 |
| ATP5B | ATP synthase subunit beta, mitochondrial | 2 |
| β-galactosidase | Beta-galactosidase | 1 |
| BIRC2 | Baculoviral IAP repeat-containing protein 2 | 2 |
| BTK | Tyrosine-protein kinase BTK | 4 |
| C1 esterase inhibitor | Plasma protease C1 inhibitor | 3 |
| C1q | Complement C1q | 1 |
| C1s | Complement C1s | 1 |
| C3 | Complement C3 | 4 |
| C4 | Complement C4 | 4 |
| C5 | Complement C5 | 3 |

TABLE 2-continued

Discovery phase scFv specificities; n = 396

| Antigen/Biomarker | Full name | No. of scFvs |
|---|---|---|
| CD40 | CD40 protein | 4 |
| CD40L | CD40 ligand | 1 |
| CDK2 | Cyclin-dependent kinase 2 | 2 |
| CEACAM-1 | Carcinoembryonic antigen-related cell adhesion molecule 1 | 2 |
| CEACAM-5 | Carcinoembryonic antigen-related cell adhesion molecule 5 | 3 |
| CHEK2 | Serine/threonine-protein kinase Chk2 | 2 |
| CHP1 | Calcineurin B homologous protein 1 | 2 |
| CHX10 | Visual system homeobox 2 | 3 |
| CSNK1E | Casein kinase I isoform epsilon | 2 |
| CTLA-4 | Cytotoxic T-lymphocyte protein 4 | 2 |
| Cystatin B | Cystatin B | 1 |
| Cystatin C | Cystatin-C | 4 |
| DCNL1 | DCN1-like protein 1 | 2 |
| DKK-1 | Dickkopf-related protein 1 | 2 |
| DLG1 | Disks large homolog 1 | 2 |
| DLG2 | Disks large homolog 2 | 2 |
| DLG4 | Disks large homolog 4 | 2 |
| DPOLM | DNA-directed DNA/RNA polymerase mu | 2 |
| DUSP7 | Dual specificity protein phosphatase 7 | 2 |
| DUSP9 | Dual specificity protein phosphatase 9 | 1 |
| EGFR | Epidermal growth factor receptor | 2 |
| Eotaxin | Eotaxin | 3 |
| Factor B | Complement factor B | 3 |
| FASN | Fatty acid synthase | 4 |
| FER | Tyrosine-protein kinase Fer | 2 |
| FGF2 | Fibroblast growth factor 2 | 2 |
| GAK | GAK protein | 3 |
| GDF-15 | Growth/differentiation factor 15 | 1 |
| GEM | GTP-binding protein GEM | 2 |
| GLP-1 | Glucagon-like peptide-1 | 1 |
| GLP-1R | Glucagon-like peptide 1 receptor | 1 |
| GM-CSF | Granulocyte-macrophage colony-stimulating factor | 4 |
| GNAI3 | Guanine nucleotide-binding protein G(k) subunit alpha | 2 |
| GORS2 | Golgi reassembly-stacking protein 2 | 2 |
| GPRK5 | G protein-coupled receptor kinase 5 | 1 |
| GRIP2 | Glutamate receptor-interacting protein 2 | 2 |
| HADH2 | HADH2 protein | 4 |
| Her2/ErbB2 | Receptor tyrosine-protein kinase erbB-2 | 4 |
| HLA-DR/DP | HLA-DR/DP | 1 |
| ICAM-1 | Intercellular adhesion molecule 1 | 1 |
| IFN-γ | Interferon gamma | 3 |
| IGFBP2 | Insulin-like growth factor-binding protein 2 | 1 |
| IGFBP3 | Insulin-like growth factor-binding protein 3 | 1 |
| IgM | IgM | 4 |
| IL-10 | Interleukin-10 | 2 |
| IL-11 | Interleukin-11 | 3 |
| IL-12 | Interleukin-12 | 4 |
| IL-13 | Interleukin-13 | 1 |
| IL-16 | Interleukin-16 | 2 |
| IL-18 | Interleukin-18 | 3 |
| IL-1-ra | Interleukin-1 receptor antagonist protein | 3 |
| IL-1α | Interleukin-1 alpha | 3 |
| IL-1β | Interleukin-1 beta | 2 |
| IL-2 | Interleukin-2 | 1 |
| IL-2-ra | Interleukin-2 receptor subunit alpha | 1 |
| IL-3 | Interleukin-3 | 3 |
| IL-4 | Interleukin-4 | 3 |
| IL-5 | Interleukin-5 | 1 |
| IL-6 | Interleukin-6 | 4 |
| IL-7 | Interleukin-7 | 1 |
| IL-8 | Interleukin-8 | 3 |
| IL-9 | Interleukin-9 | 2 |
| INADL | InaD-like protein | 2 |
| Integrin α-11 | Integrin alpha-11 | 1 |
| ITCH | E3 ubiquitin-protein ligase Itchy homolog | 2 |
| JAK3 | Tyrosine-protein kinase JAK3 | 1 |
| KCC2B | Calcium/calmodulin-dependent protein kinase type II subunit beta | 2 |
| KCC4 | Calcium/calmodulin-dependent protein kinase type IV | 2 |
| Keratin 19 | Keratin, type I cytoskeletal 19 | 3 |
| KKCC1 | Calcium/calmodulin-dependent protein kinase 1 | 2 |
| KRASB | GTPase KRas | 1 |
| KSYK | Tyrosine-protein kinase SYK | 1 |
| LDL | Apolipoprotein B-100 | 2 |
| Leptin | Leptin | 1 |
| Lewis x | Lewis x | 2 |
| Lewis y | Lewis y | 1 |
| LIF | Leukemia inhibitory factor | 2 |
| LIN7A | Protein lin-7 homolog A | 2 |
| LUM | Lumican | 1 |
| MAGI1 | Membrane-associated guanylate kinase, WW and PDZ domain-containing protein 1 | 2 |
| MAP2K2 | Dual specificity mitogen-activated protein kinase 2 | 2 |
| MAP2K6 | Dual specificity mitogen-activated protein kinase 6 | 4 |
| MAPK9 | Mitogen-activated protein kinase 9 | 2 |
| MARK1 | Serine/threonine-protein kinase MARK1 | 2 |
| MARK2 | Serine/threonine-protein kinase MARK2 | 2 |
| MATK | Megakaryocyte-associated tyrosine-protein kinase | 2 |
| MCP-1 | C-C motif chemokine 2 | 3 |
| MCP-3 | C-C motif chemokine 7 | 2 |
| MCP-4 | C-C motif chemokine 13 | 1 |
| MD2L1 | Mitotic spindle assembly checkpoint protein MAD2A | 2 |
| MK01 | Mitogen-activated protein kinase 1 | 4 |
| MK08 | Mitogen-activated protein kinase 8 | 3 |
| MMP3 | Matrix metalloproteinase-3 | 2 |
| MMP9 | Matrix metalloproteinase-9 | 2 |
| MSLN | Mesothelin | 2 |
| MUC1 | Mucin-1 | 4 |
| MUC16 | Mucin-16 | 2 |
| MYOM2 | Myomesin-2 | 2 |
| NDC80 | Kinetochore protein NDC80 homolog | 2 |
| NOS1 | Nitric oxide synthase, brain | 2 |
| OPG | Osteoprotegerin | 1 |
| OSBPL3 | Oxysterol-binding protein-related protein 3 | 2 |
| OSTP | Osteopontin | 3 |
| OTU6B | OTU domain-containing protein 6B | 2 |
| OTUB1 | Ubiquitin thioesterase OTUB1 | 2 |
| OTUB2 | Ubiquitin thioesterase OTUB2 | 2 |
| OX40 | Tumor necrosis factor ligand superfamily member 4 | 2 |
| P85A | Phosphatidylinositol 3-kinase regulatory subunit alpha | 3 |
| PAK4 | Serine/threonine-protein kinase PAK 4 | 2 |
| PAK5 | Serine/threonine-protein kinase PAK 5 | 2 |
| PARP1 | Poly [ADP-ribose] polymerase 1 | 1 |
| PARP6B | Partitioning defective 6 homolog beta | 1 |
| PD-1 | Programmed cell death protein 1 | 3 |
| PD-L1 | Programmed cell death 1 ligand 1 | 2 |
| PD-L2 | Programmed cell death 1 ligand 2 | 2 |
| PGAM5 | Serine/threonine-protein phosphatase PGAM5, mitochondrial | 2 |
| PRD14 | PR domain zinc finger protein 14 | 3 |
| PRDM8 | PR domain zinc finger protein 8 | 2 |
| PRKCZ | Protein kinase C zeta type | 2 |
| PRKG2 | cGMP-dependent protein kinase 2 | 2 |
| Procathepsin W | Cathepsin W | 1 |
| Prolactin | Prolactin | 2 |
| Properdin | Properdin | 1 |
| PSA | Prostate-specific antigen | 1 |
| PTK6 | Protein-tyrosine kinase 6 | 1 |
| PTN13 | Tyrosine-protein phosphatase non-receptor type 13 | 2 |
| PTPN1 | Tyrosine-protein phosphatase non-receptor type 1 | 3 |
| PTPRD | Receptor-type tyrosine-protein phosphatase delta | 2 |
| PTPRJ | Receptor-type tyrosine-protein phosphatase eta | 4 |
| PTPRK | Receptor-type tyrosine-protein phosphatase kappa | 4 |

TABLE 2-continued

Discovery phase scFv specificities; n = 396

| Antigen/Biomarker | Full name | No. of scFvs |
|---|---|---|
| PTPRN2 | Receptor-type tyrosine-protein phosphatase N2 | 2 |
| PTPRO | Receptor-type tyrosine-protein phosphatase O | 3 |
| PTPRT | Receptor-type tyrosine-protein phosphatase T | 2 |
| RANTES | C-C motif chemokine 5 | 2 |
| RPS6KA2 | Ribosomal protein S6 kinase alpha-2 | 3 |
| SHC1 | SHC-transforming protein 1 | 2 |
| Sialyl Lewis a | Sialyl Lewis a | 1 |
| Sialyl Lewis x | Sialyl Lewis x | 1 |
| SNTA1 | Alpha-1-syntrophin | 2 |
| Sox11a | Transcription factor SOX-11 | 1 |
| SPDLY | Protein Spindly | 2 |
| STAP1 | Signal-transducing adaptor protein 1 | 2 |
| STAP2 | Signal-transducing adaptor protein 2 | 4 |
| STAT1 | Signal transducer and activator of transcription 1-alpha/beta | 2 |
| TBC1D9 | TBC1 domain family member 9 | 2 |
| TENS4 | Tensin-4 | 1 |
| TFPI | Tissue factor pathway inhibitor | 2 |
| TGF-β1 | Transforming growth factor beta-1 | 3 |
| TNFRSF14 | Tumor necrosis factor receptor superfamily member 14 | 2 |
| TNFRSF3 | Tumor necrosis factor receptor superfamily member 3 | 3 |
| TNF-α | Tumor necrosis factor | 3 |
| TNF-β | Lymphotoxin-alpha | 4 |
| TOPB1 | DNA topoisomerase 2-binding protein 1 | 2 |
| TTR | Transthyretin | 2 |
| TXLNA | Alpha-taxilin | 2 |
| UBC9 | SUMO-conjugating enzyme UBC9 | 3 |
| UBE2C | Ubiquitin-conjugating enzyme E2 C | 2 |
| UBP7 | Ubiquitin carboxyl-terminal hydrolase 7 | 3 |
| UCHL5 | Ubiquitin carboxyl-terminal hydrolase isozyme L5 | 1 |
| UPAR | Urokinase plasminogen activator surface receptor | 2 |
| UPF3B | Regulator of nonsense transcripts 3B | 2 |
| VEGF | Vascular endothelial growth factor | 3 |
| WFDC2 | WAP four-disulfide core domain protein 2 | 2 |

TABLE 3

8-plex biomarker signature

| scFv clone | Primary target | Uniprot ID | Secondary target(s) | Uniprot ID |
|---|---|---|---|---|
| C4 (3) | Complement C4 | P0C0L4/5 | N/A | N/A |
| C5 (2) | Complement C5 | P01031 | N/A | N/A |
| Cystatin C (1) | Cystatin C | P01034 | N/A | N/A |
| Factor B (2) | Complement Factor B | P00751 | N/A | N/A |
| HADH2 (3) | GSN | P06396 | HADH2 | Q99714 |
| IGFBP3 (2) | IGFBP-3 | P17936 | N/A | N/A |
| MUC16 (1) | Mucin-16 | Q8WXI7 | FCN2, MASP2 | Q15485, O00187 |
| OPG (2) | OPG | O00300 | VWF | P04275 |

TABLE 4

Exemplary discriminating power of biomarkers and biomarker combinations (PDAC vs All controls).

| ROC-AUC | Biomarker signature |
|---|---|
| 0.929 | CA19-9 + GSN[1] + OPG[2] |
| 0.931 | CA19-9 + GSN[1] + OPG[2] + Factor B |
| 0.933 | CA19-9 + GSN[1] + OPG[2] + IGFBP3 |
| 0.927 | CA19-9 + OPG[2] + Factor B + IGFBP3 |
| 0.923 | CA19-9 + OPG[2] + IGFBP3 + MUC16[3] |
| 0.938 | CA19-9 + GSN[1] + OPG[2] + Factor B + IGFBP3 |
| 0.939 | CA19-9 + GSN[1] + OPG[2] + Factor B + IGFBP3 + C5 |
| 0.941 | CA19-9 + GSN[1] + OPG[2] + Factor B + IGFBP3 + C5 + MUC16[3] |
| 0.941 | CA19-9 + GSN[1] + OPG[2] + Factor B + IGFBP3 + C5 + MUC16[3] + Cystatin C |
| 0.940 | CA19-9 + GSN[1] + OPG[2] + Factor B + IGFBP3 + C5 + MUC16[3] + Cystatin C + C4 |
| 0.932 | CA19-9 + GSN[1] + Factor B + C5 + Cystatin C + C4 |
| 0.924 | CA19-9 + IGFBP3 + Factor B + C5 + Cystatin C + C4 |
| 0.919 | CA19-9 + MUC16[3] + Factor B + C5 + Cystatin C + C4 |
| 0.896 | CA19-9 + Factor B + C5 + Cystatin C + C4 |
| 0.838 | GSN[1] + OPG[2] |
| 0.850 | GSN[1] + OPG[2] + Factor B |
| 0.861 | GSN[1] + OPG[2] + IGFBP3 |
| 0.848 | OPG[2] + Factor B + IGFBP3 |
| 0.845 | OPG[2] + IGFBP3 + MUC16[3] |
| 0.873 | GSN[1] + OPG[2] + Factor B + IGFBP3 |
| 0.878 | GSN[1] + OPG[2] + Factor B + IGFBP3 + C5 |
| 0.885 | GSN[1] + OPG[2] + Factor B + IGFBP3 + C5 + MUC16[3] |
| 0.884 | GSN[1] + OPG[2] + Factor B + IGFBP3 + C5 + MUC16[3] + Cystatin C |
| 0.884 | GSN[1] + OPG[2] + Factor B + IGFBP3 + C5 + MUC16[3] + Cystatin C + C4 |
| 0.854 | GSN[1] + Factor B + C5 + Cystatin C + C4 |
| 0.833 | IGFBP3 + Factor B + C5 + Cystatin C + C4 |
| 0.809 | MUC16[3] + Factor B + C5 + Cystatin C + C4 |
| 0.645 | Factor B + C5 + Cystatin C + C4 |

[1]And/or HADH2, [2]And/or VWF, [3]And/or MASP2 and/or FCN2

TABLE 5

Amino acid sequences of the scFv antibodies directed against the biomarkers in Table 3
*The molecular architecture of the scFv constructs is described in Söderlind et al., 2000, and Säll et al., 2016.

| scFv clone | Antigen(s) | Amino acid sequence |
|---|---|---|
| C4 (3) | Complement C4 | EVQLLESGGGLVQPGGSLRLSCAASGFTFSSYAMSWVRQAPGKGLEWVSAISGSGGSTYYADSVKGRFTISRDNSKN TLYLQMNSLRAEDTAVYYCARGWSTSSFDYWGQGTLVTVSSGGGGSGGGGSGGGGSQSVLTQPPSASGTPGQRVTI SCSGSSSNIGNHYVSWYQQLPGTATKLLIYYDDLLPSGVPDRFSGSKSGTSASLAISGLRSEDEADYYCAAWDDRSGQ VLFGGGTKLTVLGDYKDHDGDYKDHDIDYKDDDDKAAAHHHHHH* [SEQ ID NO: 15] |
| C5 (2) | Complement C5 | EVQLLESGGGLVQPGGSLRLSCAASGFTFSAYSMNWVRQAPGKGLEWVSGVSWNGSRTHYADSVKGRFTISRDNSK NTLYLQMNSLRAEDTAVYYCARENSGFFDYWGQGTLVTVSSGGGGSGGGGSGGGGSQSVLTQPPSASGTPGQRVTIS CTGSSSNIGSNTVNWYQQLPGTAPKLLIYGNSNRPSGVPDRFSGSKSGTSASLTISGLRSEDEADYYCAAWDDSLSG WVFGGGTKLTVLGEQKLISEEDLSGSAAAHHHHHH* [SEQ ID NO: 6] |

TABLE 5-continued

Amino acid sequences of the scFv antibodies directed against the biomarkers in Table 3
*The molecular architecture of the scFv constructs is described in Söderlind et al., 2000,
and Säll et al., 2016.

| scFv clone | Antigen(s) | Amino acid sequence |
|---|---|---|
| Cystatin C (1) | Cystatin C | EVQLLESGGGLVQPGGSLRLSCAASGFTFSSYAMNWVRQAPGKGLEWVGLISYDGRTTYYADSVKGRSTISRDNSKNT LYLQMNSLRAEDTAVYYCATTTGTTLDYWGQGTLVTVSSGGGGSGGGGSGGGGSQSVLTQPPSASGTPGQRVTISCT GSSSNIGAGYDVHWYQQLPGTAPKLLIYGNTNRPSGVPDRFSGSKSGTSASLAISGLRSEDEADYYCAAWDDSLYGW VFGGGTKLTVLGDYKDHDGDYKDHDIDYKDDDDKAAAHHHHHH* [SEQ ID NO: 11] |
| Factor B (2) | Complement Factor B | EVQLLESGGGLVQPGGSLRLSCAASGFTFSSYSMNWVRQAPGKGLEWVAVISYDGRFIYYSDSVKGRFTISRDNSKNT LYLQMNSLRAEDTAVYYCARSYGGNLAMDVWGQGTLVTVSSGGGGSGGGGSGGGGSQSVLTQPPSASGTPGQRVTI SCTGSSSNIGAGYDVHWYQQLPGTAPKLLIYDNNKRPSGVPDRFSGSNSGTSASLAISGLRSEDEADYYCAAWDDRLN GRVVFGGGTKLTVLGDYKDHDGDYKDHDIDYKDDDDKAAAHHHHHH* [SEQ ID NO: 13] |
| HADH2 (3) | HADH2 and/or GSN | EVQLLESGGGLVQPGGSLRLSCAASGFTFGSSYMSWVRQAPGKGLEWVSSISSYGYYTGYADSVKGRFTISRDNSKNT LYLQMNSLRAEDTAVYYCARSYGSWYFDYWGQGTLVTVSSGGGGSGGGGSGGGGSDIQMTQSPSSLSASVGDRVTI TCRASQSISSYLNWYQQKPGKAPKLLIYAASSLQSGVPSRFSGSGSGTDFTLTISSLQPEDFATYYCQQGFVGPSTFGQ GTKLEIKRLGDYKDHDGDYKDHDIDYKDDDDKAAAHHHHHH* [SEQ ID NO: 20] |
| IGFBP3 (2) | IGFBP3 | EVQLLESGGGLVQPGGSLRLSCAASGFTFSSYAMSWVRQAPGKGLEWVSAISGSGGSTYYADSVKGRFTISRDNSKN TLYLQMNSLRAEDTAVYYCARGGGIVFDYWGQGTLVTVSSGGGGSGGGGSGGGGSDIQMTQSPSSLSASVGDRVTIT CRASQSISSYLNWYQQKPGKAPKLLIYAASSLQSGVPSRFSGSGSGTDFTLTISSLQPEXFATYYCQQSYSTPYTFGQGT KLEIKRLGDYKDHDGDYKDHDIDYKDDDDKAAAHHHHHH* [SEQ ID NO: 32] |
| MUC16 (1) | MUC16 and/or FCN2 and/or MASP2 | EVQLLESGGGLVQPGGSLRLSCAASGFTFNNYAMNWVRQAPGKGLEWVSGIGYYGSYTSYADSVKGRFTISRDNSKN TLYLQMNSLRAEDTAVYYCARDYSFDYWGQGTLVTVSSGGGGSGGGGSGGGGSDIQMTQSPSSLSASVGDRVTITC RASQSISSYLNWYQQKPGKAPKLLIYAASSLQSGVPSRFSGSGSGTDFTLTISSLQPEDFATYYCQQGFYPYTFGQGTKL EIKRLGDYKDHDGDYKDHDIDYKDDDDKAAAHHHHHH* [SEQ ID NO: 30] |
| OPG (2) | OPG and/or VWF | EVQLLESGGGLVQPGGSLRLSCAASGFTFSSYAMSWVRQAPGKGLEWVSAISGSGGSTYYADSVKGRFTISRDNSKN TLYLQMNSLRAEDTAVYYCARDFYSYSGFDYWGQGTLVTVSSGGGGSGGGGSGGGGSDIQMTQSPSSLSASVGDRV TITCRASQSISSYLNWYQQKPGKAPKLLIYAASSLQSGVPSRFSGSGSGTDFTLTISSLQPEDFATYYCQQYGYYPLTFG QGTKLEIKRLGDYKDHDGDYKDHDIDYKDDDDKAAAHHHHHH* [SEQ ID NO: 36] |

TABLE 6

Amino acid sequences of the scFv antibodies listed in Table 1
*The molecular architecture of the scFv constructs is described in Söderlind et al., 2000,
and Säll et al., 2016.

| scFv clone | Amino acid sequence |
|---|---|
| TGF-β1 (1) | EVQLLESGGGLVQPGGSLRLSCAASGFTFSTYAMSWVRQAPGKGLEWVAVVSIDGGTTYYGDPVKGRFTISRDNSKNTLYLQMNSLRAEDTAVYY CTRGPTLTYYFDYWGQGTLVTVSSGGGGSGGGGSGGGGSQSVLTQPPSASGTPGQRVTISCSGSSSNIGSNTVNWYQQLPGTAPKLLIYSNNQR PSGVPDRFSGSKSGTSASLAISGLRSEDEADYYCQSYDSSLSGWVFGGGTKLTVLGEQKLISEEDLSGSAAAHHHHHH* [SEQ ID NO: 1] |
| IFN-γ (2) | EVQLLESGGGLVQPGGSLRLSCAASGFTFSRHGFHWVRQGPGKGLEWVSGVSWNGSRTHYADSVKGRFTISRDNSKNTLYLQMNSLRAEDTAV YYCARGNWYRAFDIWGQGTLVTVSSGGGGSGGGGSGGGGSQSVLTQPPSASGTPGQRVTISCSGSSSHIGRNFISWYQQLPGTAPKLLIYAGN SRPSGVPDRFSGSKSGTSASLAISGLRSEDEADYYCAAWDDSLSGVVFGGGTKLTVLGEQKLISEEDLSGSAAAHHHHHH* [SEQ ID NO: 2] |
| PSA | EVQLLESGGGLVQPGGSLRLSCAASGFTFRSYEMNWVRQAPGKGLEWVAVIGGNGVDTDYADSVKGRFTISRDNSKNTLYLQMNSLRAEDTAVY YCVREEVDFWSGYYSYGMDVWGQGTLVTVSSGGGGSGGGGSGGGGSQSVLTQPPSASGTPGQRVTISCSGSSSNIGDNFVSWYQQLPGTAPK LLIYRTNGRPSGVPDRFSGSKSGTSASLAISGLRSEDEADYYCATWDDNLNGRVVFGGGTKLTVLGDYKDDDDKAAAHHHHHH* [SEQ ID NO: 3] |
| C3 (1) | EVQLLESGGGLVQPGGSLRLSCAASGFTFSSYAMSWVRQAPGKGLEWVSSVTGSGGGTYYADSVEGRFTISRDNSKNTLYLQMNSLRAEDTAVY YCARYRWFGNDAFDIWGQGTLVTVSSGGGGSGGGGSGGGGSQSVLTQPPSASGTPGQRVTISCSGSASNLGMHFVSWYQQLPGTAPKLLIYGN SNRPSGVPDRFSGSKSGTSASLAISGLRSEDEADYYCAAWDDTLNIWVFGGGTKLTVLGEQKLISEEDLSGSAAAHHHHHH* [SEQ ID NO: 4] |
| C3 (2) | EVQLLESGGGLVQPGGSLRLSCAASGFTFSTYRMIWVRQAPGKGLEWVSSISGSNTYIHYADSVRGRFTISRDNSKNTLYLQMNSLRAEDTAVYY CARDRHPLLPSGMDVWGQGTLVTVSSGGGGSGGGGSGGGGSQSVLTQPPSASGTPGQRVTISCSGSSSNIGKHPVNWYQQLPGTAPKLLIYRN DQRPSGVPDRFSGSKSGTSASLAISGLRSEDEADYYCQSYDSSLSGSWVFGGGTKLTVLGEQKLISEEDLSGSAAAHHHHHH* [SEQ ID NO: 5] |
| C5 (2) | EVQLLESGGGLVQPGGSLRLSCAASGFTFSAYSMNWVRQAPGKGLEWVSGVSWNGSRTHYADSVKGRFTISRDNSKNTLYLQMNSLRAEDTAV YYCARENSGFFDYWGQGTLVTVSSGGGGSGGGGSGGGGSQSVLTQPPSASGTPGQRVTISCTGSSSNIGSNTVNWYQQLPGTAPKLLIYGNSN RPSGVPDRFSGSKSGTSASLTISGLRSEDEADYYCAAWDDSLSGWVFGGGTKLTVLGEQKLISEEDLSGSAAAHHHHHH* [SEQ ID NO: 6] |

TABLE 6-continued

Amino acid sequences of the scFv antibodies listed in Table 1
*The molecular architecture of the scFv constructs is described in Söderlind et al., 2000, and Säll et al., 2016.

| scFv clone | Amino acid sequence |
|---|---|
| C1 inh. (1) | EVQLLESGGGLVQPGGSLRLSCAASGFTFSDYYMSWIRQAPGKGLEWVSGISRGGEYTFYVDSVKGRFTISRDNSKNTLYLQMNSLRAEDTAVYY CARDPGGLDAFDIWGQGTLVTVSSGGGGSGGGGSGGGGSQSVLTQPPSASGTPGQRVTISCTGSSSNIGARYDVQWYQQLPGTAPKLLIYGNS NRPSGVPDRFSGSKSGTSASLAISGLRSEDEADYYCASWDDSLSGPVFGGGTKLTVLGEQKLISEEDLSGSAAAHHHHHH* [SEQ ID NO: 7] |
| Properdin | EVQLLESGGGLVQPGGSLRLSCAASGFTFSSNYMSWVRQAPGKGLEWVSAISGSGGSTYYADSVKGRFTISRDNSKNTLYLQMNSLRAEDTAVY YCAKGGSGWYDYFDYWGQGTLVTVSSGGGGSGGGGSGGGGSQSVLTQPPSASGTPGQRVTISCTGSSSNIGAGYDVHWYQQLPGTAPKLLIY RNNQRPSGVPDRFSGSKSGTSASLAISGLRSEDEADYYCAAWDDGLNSPVFGGGTKLTVLGEQKLISEEDLSGSAAAHHHHHH* [SEQ ID NO: 8] |
| VEGF (3) | EVQLLESGGGLVQPGGSLRLSCAASGFTFSSYEMNWVRQAPGKGLEWVSGISGSGGFTYYADSVKGRFTISRDNSKNTLYLQMNSLRAEDTAMY YCAREGYQDAFDIWGQGTLVTVSSGGGGSGGGGSGGGGSQSVLTQPPSASGTPGQRVTISCTGSSSNIGAGYDVHWYQQLPGTAPKLLIYSNN QRPSGVPDRFSGSKSGTSASLAISGLRSEDEADYYCAAWDDSLSGPPWVFGGGTKLTVLGEQKLISEEDLSGSAAAHHHHHH* [SEQ ID NO: 9] |
| CD40 (1) | EVQLLESGGGLVQPGGSLRLSCAASGFTFSDYYMSWVRQAPGKGLEWVSGISGNGGYTYFADSVKDRFTISRDNSKNTLYLQMNSLRAEDTAVY YCARAPVDYSNPSGMDVWGQGTLVTVSSGGGGSGGGGSGGGGSQSVLTQPPSASGTPGQRVTISCSGSRSNIGLNTVNWYQQLPGTAPKLLIY GNSNRPSGVPDRFSGSKSGTSASLAISGLRSEDEADYYCAGWDDSLSGWVFGGGTKLTVLGDYKDDDDKAAAHHHHHH* [SEQ ID NO: 10] |
| Cystatin C (1) | EVQLLESGGGLVQPGGSLRLSCAASGFTFSSYAMNWVRQAPGKGLEWVGLISYDGRTTYYADSVKGRSTISRDNSKNTLYLQMNSLRAEDTAVYY CATTTGTTLDYWGQGTLVTVSSGGGGSGGGGSGGGGSQSVLTQPPSASGTPGQRVTISCTGSSSNIGAGYDVHWYQQLPGTAPKLLIYGNTNR PSGVPDRFSGSKSGTSASLAISGLRSEDEADYYCAAWDDSLYGWVFGGGTKLTVLGDYKDHDGDYKDHDIDYKDDDDKAAAHHHHHH* [SEQ ID NO: 11] |
| Apo-A1 (3) | EVQLLESGGGLVQPGGSLRLSCAASGFTFRDYYMSWIRQAPGKGLEWVAVTSYDGSKKYYADSVKGRFTISRDNSKNTLYLQMNSLRAEDTAVYY CAKDYADDSIAAPAFDIWGQGTLVTVSSGGGGSGGGGSGGGGSQSVLTQPPSASGTPGQRVTISCTGSSSNIGAGYDVHWYQQLPGTAPKLLIY GNSNRPSGVPDRFSGSKSGTSASLAISGLRSEDEADYYCQSYDSSLSVVFGGGTKLTVLGDYKDHDGDYKDHDIDYKDDDDKAAAHHHHHH* [SEQ ID NO: 12] |
| Factor B (2) | EVQLLESGGGLVQPGGSLRLSCAASGFTFSSYSMNWVRQAPGKGLEWVAVISYDGRFIYYSDSVKGRFTISRDNSKNTLYLQMNSLRAEDTAVYY CARSYGGNLAMDVWGQGTLVTVSSGGGGSGGGGSGGGGSQSVLTQPPSASGTPGQRVTISCTGSSSNIGAGYDVHWYQQLPGTAPKLLIYDN NKRPSGVPDRFSGSNSGTSASLAISGLRSEDEADYYCAAWDDRLNGRVVFGGGTKLTVLGDYKDHDGDYKDHDIDYKDDDDKAAAHHHHHH* [SEQ ID NO: 13] |
| Factor B (4) | EVQLLESGGGLVQPGGSLRLSCAASGFTFSKHSMNWVRQAPGKGLEWVATVSYDGNYKYYADSVKGRFTISRDNSKNTLYLQMNSLRAEDTAVY YCAREGYYYYGMDVWGQGTLVTVSSGGGGSGGGGSGGGGSQSVLTQPPSASGTPGQRVTISCTGSSSNIGNNAVNWYQQLPGTAPKLLIYNNN QRPSGVPDRFSGSKSGTSASLAISGLRSEDEADYYCQPYDDSLSSVVFGGGTKLTVLGDYKDHDGDYKDHDIDYKDDDDKAAAHHHHHH* [SEQ ID NO: 14] |
| C4 (3) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARGWSTSSFDYWGQGTLVTVSSGGGGSGGGGSGGGGSQSVLTQPPSASGTPGQRVTISCSGSSSNIGNHYVSWYQQLPGTATKLLIYYDDL LPSGVPDRFSGSKSGTSASLAISGLRSEDEADYYCAAWDDRSGQVLFGGGTKLTVLGDYKDHDGDYKDHDIDYKDDDDKAAAHHHHHH* [SEQ ID NO: 15] |
| C3 (3) | EVQLLESGGGLVQPGGSLRLSCAASGFTFSSYAMNWVRQAPGKGLEWVANINQDGSTKFYVDSVKGRFTISRDNSKNTLYLQMNSLRAEDTAVY YCARDTGGNYLGGYYYYGMDVWGQGTLVTVSSGGGGSGGGGSGGGGSQSVLTQPPSASGTPGQRVTISCSGSSSNIGSNYVYWYQQLPGTAP KLLIYRNDQRPSGVPDRFSGSKSGTSASLAISGLRSEDEADYYCSSYAGNNNLVFGGGTKLTVLGDYKDHDGDYKDHDIDYKDDDDKAAAHHHH HH* [SEQ ID NO: 16] |
| MYOM2 (1) | EVQLLESGGGLVQPGGSLRLSCAASGFTFSSYAMSWVRQAPGKGLEWVSGISGSGGSTYYADSVKGRFTISRDNSKNTLYLQMNSLRAEDTAVY YCARGVVAGSWGQGTLVTVSSGGGGSGGGGSGGGGSQSVLTQPPSASGTPGQRVTISCSGSSSNIGNNAVNWYQQLPGTAPKLLIYDNNKRP SGVPDRFSGSKSGTSASLAISGLRSEDEADYYCAAWGXQPEWLGVRRRNQADSPRXLQRPXRXLXRSXHRLQDDDDKAAAHHHHHH [SEQ ID NO: 17] |
| CHX10 (3) | EVQLLESGGGLVQPGGSLRLSCAASGFTFSSYAMSWVRQAPGKGLEWVAVISYDGSNKYYADSVKGRFTISRDNSKNTLYLQMNSLRAEDTAVY YCARNYGDSINWFDPWGQGTLVTVSSGGGGSGGGGSGGGGSQSVLTQPPSASGTPGQRVTISCSGSSSNIRSNTVNWYQQLPGTAPKLLIYGN SNRPSGVPDRFSGSKSGTSASLAISGLRSEDEADYYCAAWDDSLNGWVFGGGTKLTVLGDYKDHDGDYKDHDIDYKDDDDKAAAHHHHHH* [SEQ ID NO: 18] |
| BTK (3) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARGYYGMDYWGQGTLVTVSSGGGGSGGGGSGGGGSDIQMTQSPSSLSASVGDRVTITCRASQSISSYLNWYQQKPGKAPKLLIYAASSLQS GVPSRFSGSGSGTDFTLTISSLQPEDFATYYCQQTWYLPTFGQGTKLEIKRLGDYKDHDGDYKDHDIDYKDDDDKAAAHHHHHH* [SEQ ID NO: 19] |
| HADH2 (3) | EVQLLESGGGLVQPGGSLRLSCAASGFTFSSYMSWVRQAPGKGLEWVSSISSYGYYTGYADSVKGRFTISRDNSKNTLYLQMNSLRAEDTAVYY CARSYGSWYFDYWGQGTLVTVSSGGGGSGGGGSGGGGSDIQMTQSPSSLSASVGDRVTITCRASQSISSYLNWYQQKPGKAPKLLIYAASSLQ SGVPSRFSGSGSGTDFTLTISSLQPEDFATYYCQQGFVGPSTFGQGTKLEIKRLGDYKDHDGDYKDHDIDYKDDDDKAAAHHHHHH* [SEQ ID NO: 20] |

TABLE 6-continued

Amino acid sequences of the scFv antibodies listed in Table 1
*The molecular architecture of the scFv constructs is described in Söderlind et al., 2000,
and Säll et al., 2016.

| scFv clone | Amino acid sequence |
|---|---|
| MATK (1) | EVQLLESGGGLVQPGGSLRLSCAASGFTFGSSYMGWVRQAPGKGLEWVSGIGGYGYYTGYADSVKGRFTISRDNSKNTLYLQMNSLRAEDTAVY YCARYDWGHSPGSWYYGSFDYWGQGTLVTVSSGGGGSGGGGSGGGGSQSVLTQPPSASGTPGQRVTISCSGSSSNIGSSYVYWYQQLPGTAP KLLIYSNNQRPSGVPDRFSGSKSGTSASLAISGLRSEDEADYYCAAWAGAYHSHVVFGGGTKLTVLGDYKDHDGDYKDHDIDYKDDDDKAAAHH HHHH* [SEQ ID NO: 21] |
| TNFRSF3 (2) | EVQLLESGGGLVQPGGSLRLSCAASGFTFGSSYMYWVRQAPGKGLEWVSSIYGSSSSTSYADSVKGRFTISRDNSKNTLYLQMNSLRAEDTAVYY CARGYYWDYMDYWGQGTLVTVSSGGGGSGGGGSGGGGSDIQMTQSPSSLSASVGDRVTITCRASQSISSYLNWYQQKPGKAPKLLIYAASSLQ SGVPSRFSGSGSGTDFTLTISSLQPEDFATYYCQQAWDLPTFGQGTKLEIKRLGDYKDHDGDYKDHDIDYKDDDDKAAAHHHHHH* [SEQ ID NO: 22] |
| UBC9 (3) | EVQLLESGGGLVQPGGSLRLSCAASGFTFSSYAMSWVRQAPGKGLEWVSSIYGSSSYTYYADSVKGRFTISRDNSKNTLYLQMNSLRAEDTAVYY CARSASWGGYFDYWGQGTLVTVSSGGGGSGGGGSGGGGSDIQMTQSPSSLSASVGDRVTITCRASQSISSYLNWYQQKPGKAPKLLIYAASSL QSGVPSRFSGSGSGTDFTLTISSLQPEDFATYYCQQSGVSPYTFGQGTKLEIKRLGDYKDHDGDYKDHDIDYKDDDDKAAAHHHHHH* [SEQ ID NO: 23] |
| UBP7 (1) | EVQLLESGGGLVQPGGSLRLSCAASGFTFGSSSMYWVRQAPGKGLEWVSSISYYGYSTYYADSVKGRFTISRDNSKNTLYLQMNSLRAEDTAVYY CARGSGIDYWGQGTLVTVSSGGGGSGGGGSGGGGSDIQMTQSPSSLSASVGDRVTITCRASQSISSYLNWYQQKPGKAPKLLIYAASSLQSGV PSRFSGSGSGTDFTLTISSLQPEDFATYYCQQWSVYGLYTFGQGTKLEIKRLGDYKDHDGDYKDHDIDYKDDDDKAAAHHHHHH* [SEQ ID NO: 24] |
| UBP7 (2) | EVQLLESGGGLVQPGGSLRLSCAASGFTFGSSSMYWVRQAPGKGLEWVSGISYYGYSTYYADSVKGRFTISRDNSKNTLYLQMNSLRAEDTAVYY CARGHSLDYWGQGTLVTVSSGGGGSGGGGSGGGGSDIQMTQSPSSLSASVGDRVTITCRASQSISSYLNWYQQKPGKAPKLLIYAASSLQSGV PSRFSGSGSGTDFTLTISSLQPEDFATYYCQQFSGYPHTFGQGTKLEIKRLGDYKDHDGDYKDHDIDYKDDDDKAAAHHHHHH* [SEQ ID NO: 25] |
| APLF (2) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARGYYDMDYWGQGTLVTVSSGGGGSGGGGSGGGGSDIQMTQSPSSLSASVGDRVTITCRASQSISSYLNWYQQKPGKAPKLLIYAASSLQS GVPSRFSGSGSGTDFTLTISSLQPEDFATYYCQQSYSTPYTFGQGTKLEIKRLGDYKDHDGDYKDHDIDYKDDDDKAAAHHHHHH* [SEQ ID NO: 26] |
| MARK1-1 (1) | EVQLLESGGGLVQPGGSLRLSCAASGFTFSGYGMWVRQAPGKGLEWVSSISYYGGGTGYADSVKGRFTISRDNSKNTLYLQMNSLRAEDTAVY YCARFDDFYASHYGIYIDYWGQGTLVTVSSGGGGSGGGGSGGGGSDIQMTQSPSSLSASVGDRVTITCRASQSISSYLNWYQQKPGKAPKLLIY AASSLQSGVPSRFSGSGSGTDFTLTISSLQPEDFATYYCQQASSLFTFGQGTKLEIKRLGDYKDHDGDYKDHDIDYKDDDDKAAAHHHHHH* [SEQ ID NO: 27] |
| PTPPRN2 (1) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARGPASSAYFDYWGQGTLVTVSSGGGGSGGGGSGGGGSDIQMTQSPSSLSASVGDRVTITCRASQSISSYLNWYQQKPGKAPKLLIYAASSL QSGVPSRFSGSGSGTDFTLTISSLQPEDFATYYCQQSYSTPYTFGQGTKLEIKRLGDYKDHDGDYKDHDIDYKDDDDKAAAHHHHHH* [SEQ ID NO: 28] |
| CEACAM5 (1) | EVQLLESGGGLVQPGGSLRLSCAASGFTFGSYYMNWVRQAPGKGLEWVSGISGNGGGTNYADSVKGRFTISRDNSKNTLYLQMNSLRAEDTAVY YCARAYYPAYFDYWGQGTLVTVSSGGGGSGGGGSGGGGSDIQMTQSPSSLSASVGDRVTITCRASQSISSYLNWYQQKPGKAPKLLIYAASSLQ SGVPSRFSGSGSGTDFTLTISSLQPEDFATYYCQQGYYPHTFGQGTKLEIKRLGDYKDHDGDYKDHDIDYKDDDDKAAAHHHHHH* [SEQ ID NO: 29] |
| MUC16 (1) | EVQLLESGGGLVQPGGSLRLSCAASGFTFNNYAMNWVRQAPGKGLEWVSGIGYYGSYTSYADSVKGRFTISRDNSKNTLYLQMNSLRAEDTAVY YCARDYSFDYWGQGTLVTVSSGGGGSGGGGSGGGGSDIQMTQSPSSLSASVGDRVTITCRASQSISSYLNWYQQKPGKAPKLLIYAASSLQSG VPSRFSGSGSGTDFTLTISSLQPEDFATYYCQQGFYPYTFGQGTKLEIKRLGDYKDHDGDYKDHDIDYKDDDDKAAAHHHHHH* [SEQ ID NO: 30] |
| MMP9 (2) | EVQLLESGGGLVQPGGSLRLSCAASGFTFSSSYMSWVRQAPGKGLEWVSSINSSGNGTYYADSVKGRFTISRDNSKNTLYLQMNSLRAEDTAVY YCARSVYLDYWGQGTLVTVSSGGGGSGGGGSGGGGSDIQMTQSPSSLSASVGDRVTITCRASQSISSYLNWYQQKPGKAPKLLIYAASSLQSG VPSRFSGSGSGTDFTLTISSLQPEDFATYYCQQFSGYPYTFGQGTKLEIKRLGDYKDHDGDYKDHDIDYKDDDDKAAAHHHHHH* [SEQ ID NO: 31] |
| IGFBP3 (2) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARGGGIVFDYWGQGTLVTVSSGGGGSGGGGSGGGGSDIQMTQSPSSLSASVGDRVTITCRASQSISSYLNWYQQKPGKAPKLLIYAASSLQ SGVPSRFSGSGSGTDFTLTISSLQPEXFATYYCQQSYSTPYTFGQGTKLEIKRLGDYKDHDGDYKDHDIDYKDDDDKAAAHHHHHH* [SEQ ID NO: 32] |
| IL-2ra (3) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARDAGWYGFDYWGQGTLVTVSSGGGGSGGGGSGGGGSDIQMTQSPSSLSASVGDRVTITCRASQSISSYLNWYQQKPGKAPKLLIYAASSL QSGVPSRFSGSGSGTDFTLTISSLQPEDFATYYCQQSYSTPYTFGQGTKLEIKRLGDYKDHDGDYKDHDIDYKDDDDKAAAHHHHHH* [SEQ ID NO: 33] |
| AGR2 (1) | EVQLLESGGGLVQPGGSLRLSCAASGFTFGYSYMSWVRQAPGKGLEWVSGISGYYYYTYYADSVKGRFTISRDNSKNTLYLQMNSLRAEDTAVYY CARVSSYHYSYIDYWGQGTLVTVSSGGGGSGGGGSGGGGSDIQMTQSPSSLSASVGDRVTITCRASQSISSYLNWYQQKPGKAPKLLIYAASSL QSGVPSRFSGSGSGTDFTLTISSLQPEXFATYYCQQSYYWGLFTFGQGTKLEIKRLGDYKDHDGDYKDHDIDYKDDDDKAAAHHHHHH* [SEQ ID NO: 34] |

TABLE 6-continued

Amino acid sequences of the scFv antibodies listed in Table 1
*The molecular architecture of the scFv constructs is described in Söderlind et al., 2000, and Säll et al., 2016.

| scFv clone | Amino acid sequence |
| --- | --- |
| IGFBP2 (1) | EVQLLESGGGLVQPGGSLRLSCAASGFTFSYYSMYWVRQAPGKGLEWVSSIGSYGYYTYYADSVKGRFTISRDNSKNTLYLQMNSLRAEDTAVYY CARSWSGFHYIDYWGQGTLVTVSSGGGGSGGGGSGGGGSDIQMTQSPSSLSASVGDRVTITCRASQSISSYLNWYQQKPGKAPKLLIYAASSL QSXVPSRFSGSGXGTDFTLTISSLQPEXFATYYCQQGYVHLLTFGQGTKLEIKRLGDYKDHDGDYKDHDIDYKDDDDKAAAHHHHHH* [SEQ ID NO: 35] |
| OPG (2) | EVQLLESGGGLVQPGGSLRLSCAASGFTFSSYAMSWVRQAPGKGLEWVSAISGSGGSTYYADSVKGRFTISRDNSKNTLYLQMNSLRAEDTAVY YCARDFYSYSGFDYWGQGTLVTVSSGGGGSGGGGSGGGGSDIQMTQSPSSLSASVGDRVTITCRASQSISSYLNWYQQKPGKAPKLLIYAASSL QSGVPSRFSGSGSGTDFTLTISSLQPEDFATYYCQQYGYYPLTFGQGTKLEIKRLGDYKDHDGDYKDHDIDYKDDDDKAAAHHHHHH* [SEQ ID NO: 36] |
| GDF-15 (1) | EVQLLESGGGLVQPGGSLRLSCAASGFTFSGYYMSWVRQAPGKGLEWVSSIYGYGYYTYYADSVKGRFTISRDNSKNTLYLQMNSLRAEDTAVYY CARGGYFHGVSDMDYWGQGTLVTVSSGGGGSGGGGSGGGGSDIQMTQSPSSLSASVGDRVTITCRASQSISSYLNWYQQKPGKAPKLLIYAAS SLQSGVPSRFSGSGSGTDFTLXISSLQPEDFATYYCXQYYNYLHTFGQGTKLEIKRLGDYKDHDGDYKDHDIDYKDDDDKAAAHHHHHH* [SEQ ID NO: 37] |
| CEACAM5 (3) | EVQLLESGGGLVQPGGSLRLSCAASGFTFSGSYMYWVRQAPGKGLEWVSGISSSGYSTSYADSVKGRFTISRDNSKNTLYLQMNSLRAEDTAVYY CARYGYYFDYWGQGTLVTVSSGGGGSGGGGSGGGGSDIQMTQSPSSLSASVGDRVTITCRASQSISSYLNWYQQKPGKAPKLLIYAASSLQSG VPSRFSGSGSGTDFTLTISSLQPEDFATYYCXQFGYPPTFGQGTKLEIKRLGDYKDHDGDYKDHDIDYKDDDDKAAAHHHHHH* [SEQ ID NO: 38] |

TABLE 7

SVM script

A) Early PDAC vs ChrP classification

```
Conduct a classification task when comparing "Early PDACs" and "Chronic Pancreatitis" using a "Frozen" SVM
approach. Here, we create a single svm model on the training set (60% of the data) and then predict using the test set (40%).
x = Subset_Early_CP
y = Subset_Early_CP$stage_grp
set.seed(2020)
train_idx = createDataPartition(Subset_Early_CP$stage_grp, p = .6)$Resample1
#table(y[-train_idx])
#Create the model and then perform prediction
mod = svm(x = as.data.frame(x)[train_idx,FinalSig], y = factor(y[train_idx]), kernel="linear",probability = TRUE)
prediction = as.data.frame(attr(predict(mod, as.data.frame(x)[-train_idx,FinalSig], decision.values =
TRUE,probability = TRUE), "probabilities"))$Early
# Call the pdf command to start the plot
pdf(file = "ROC_Early_CP_Plot_FrozenSVM.pdf")
my_roc = roc(controls = prediction[y[-train_idx] != "Early"], cases = prediction[y[-train_idx] == "Early"], plot =
TRUE, print.auc = TRUE, main = paste0("Strat 2b, 8-signature",":","Array + CA19-9, Early PDAC vs. PC"))
    points(.95,.8, pch = 20, col = "red")
    lines(x = c(1,.95,.95), y = c(.8,.8,1), col = "red",lty = "dotted")
dev.off( )
```

(B) ROC curve analysis

```
Details of the SVM script regarding the ROC AUC plots presented in patent application
thresh_to_sen <- function(my_roc, threshold){
    return(sensitivity = sum(my_roc$cases<threshold)/length(my_roc$cases))
}
thresh_to_spe <- function(my_roc, threshold){
    return(sum(my_roc$controls>threshold)/length(my_roc$controls))
}
subROCs = function(dataset, sig, my_main, threshold_sig,threshold_sig_CA19,threshold_CA19){
    dataset$ca19_9 = -dataset$ca19_9
        dataset$primary_diagnosis = gsub(" ","_", dataset$primary_diagnosis)
    sig_roc_res_list = list( )
for(i in 1:1000){
    # Random train and test
    dataset_train_idx = createDataPartition(times = 1,y = paste(dataset$site,dataset$primmy_diagnosis,sep = "_"),p = .70,list = FALSE)
    dataset_train_data = dataset[dataset_train_idx,] %>% arrange(dx)
    dataset_test_data = dataset[-dataset_train_idx,] %>% arrange(dx)
        dataset_mod_short = e1071::svm(dataset_train_data[,c(sig)], y = as.factor(dataset_train_data$dx), kernel = "linear",probability =
TRUE)
        dataset_mod_short_ca19_9 = e1071::svm(dataset_train_data[,c(sig, "ca19_9")], y = as.factor(dataset_train_data$dx), kernel =
"linear",probability = TRUE)
    arr_t_pred = attr(predict(dataset_mod_short, newdata = dataset_train_data[,sig], decision.values = TRUE), "decision.values")[,1]
    ca_arr_pred = attr(predict(dataset_mod_short_ca19_9, newdata = dataset_train_data[,c(sig, "ca19_9")], decision.values = TRUE),
"decision.values")[,1]
```

TABLE 7-continued

SVM script

```
   arr_pred = attr(predict(dataset_mod_short, newdata = dataset_test_data[,sig], decision.values = TRUE), "decision.values")[,1]
   ca_arr_pred = attr(predict(dataset_mod_short_ca19_9, newdata = dataset_test_data[,c(sig, "ca19_9")], decision.values = TRUE),
"decision.values")[,1]
# tr_pred = arr_t_pred
# te_pred = arr_pred
# try = as.factor(dataset_train_data$dx)
# te_y = asfactor(dataset_test_data$dx)
   dv = arr_pred
   ca19_9_dv = ca_arr_pred
   y = dataset_test_data$dx
   sig_roc_res_list[[i]] = tibble(
      sample_name = dataset_test_data$sample_name,
      dv,
      ca19_9_dv,
      ca19_9 = dataset_test_data$ca19_9,
      dv_rank = rank(dv),
      ca19_9_dv_rank = rank(ca19_9_dv),
      y,
      primary_diagnosis = dataset_test_data$primary_diagnosis)
}
   sigs_roc_res = do.call(rbind,sig_roc_res_list)
   sig_rank_res = sigs_roc_res %>% group_by(sample_name,y,primary_diagnosis) %>%
      nest( ) %>%
      mutate(ca19_9_dv_mean = map_dbl(data,function(x) mean(x$ca19_9_dv))) %>%
      mutate(dv_mean = map_dbl(data,function(x) mean(x$dv)))
# subgroup analysis
   sub_roc_data = left_join(sig_rank_res, dataset %>% select(sample_name, Original_Kit_ID, primary_diagnosis,
sub_group,symp_diabetes, gender, age, site, collection_date, ca19_9))
   sub_roc_data$stage_grp = "None"
   sub_roc_data$stage_grp[sub_roc_data$sub_group %in% c("Stage IA","Stage IB","Stage IIA","Stage IIB") ] = "Early"
   sub_roc_data$stage_grp[sub_roc_data$sub_group %in% c("Stage III","Stage IV") ] = "Late"
# All
   par(mfrow=c(1,3))
   all_sig_roc = pROC::roc(sig_rank_res$y,sig_rank_res$dv_mean, plot = TRUE, print.auc = TRUE, main = paste0(my_main,": 
","Array data, All"))
   points(.95,.8, pch = 20, col = "red")
   lines(x = c(1,.95,.95), y = c(.8,.8,1), col = "red",lty = "dotted")
   all_sig_roc_ca = pROC::roc(sig_rank_res$y,sig_rank_res$ca19_9_dv_mean, plot = TRUE, print.auc = TRUE, main =
paste0(my_main,": ","Array + CA19-9, All"))
   points(.95,.8, pch = 20, col = "red")
   lines(x = c(1,.95,.95), y = c(.8,.8,1), col = "red",lty = "dotted")
   all_sig_roc_caonly = pROC::roc(dataset$dx,dataset$ca19_9, plot = TRUE, print.auc = TRUE, main =
paste0(my_main,": ","CA19-9,
All"))
   points(.95,.8, pch = 20, col = "red")
   lines(x = c(1,.95,.95), y = c(.8,.8,1), col = "red",lty = "dotted")
# PDAC v Healthy
   PDAC_v_healthy = subset(sub_roc_data, y == "PDAC" | primary_diagnosis =="Healthy_Control")
   dataset$stage_grp) = "None"
   dataset$stage_grp[dataset$sub_group %in% c("Stage IA","Stage IB","Stage IIA","Stage IIB") ] = "Early"
   dataset$stage_grp[dataset$sub_group %in% c("Stage III","Stage IV") ] = "Late"
   PDAC_v_healthy_ca = subset(dataset, dx == "PDAC" | primary_diagnosis =="Healthy_Control") %>% select(ca19_9,dx)
   if(length(unique(PDAC_v_healthy$y ))>1){
      pvh_sig_roc = pROC::roc(PDAC_v_healthy$y,PDAC_v_healthy$dv_mean, plot = TRUE, print.auc = TRUE, main =
paste0(my_main,": ","Array data, PDAC vs. Healthy"))
         points(.95,.8, pch = 20, col = "red")
         lines(x = c(1,.95,.95), y = c(.8,.8,1), col = "red",lty = "dotted")
      pvh_sig_roc_ca = pROC::roc(PDAC_v_healthy$y,PDAC_v_healthy$ca19_9_dv_mean, plot = TRUE, print.auc = TRUE, main =
paste0(my_main,": ","Array + CA19-9, PDAC vs. Healthy"))
         points(.95,.8, pch = 20, col = "red")
         lines(x = c(1,.95,.95), y = c(.8,.8,1), col = "red",lty = "dotted")
      pvh_sig_roc_caonly = pROC::roc(PDAC_v_healthy_ca$dx,PDAC_v_healthy_ca$ca19_9, plot = TRUE, print.auc = TRUE,
main = paste0(my_main,": ","CA19-9, PDAC vs. Healthy"))
         points(.95,.8, pch = 20, col = "red")
         lines(x = c(1,.95,.95), y = c(.8,.8,1), col = "red",lty = "dotted")
}
# PDAC v Symptomatic
   PDAC_v_symptomatic = subset(sub_roc_data, y == "PDAC" | primary_diagnosis =="No_PDAC_Control")
   PDAC_v_symptomatic_ca = subset(dataset, dx == "PDAC" | primary_diagnosis =="No_PDAC_Control") %>% select(ca19_9,dx)
   if(length(unique(PDAC_v_symptomatic$y ))>1){
      pvs_sig_roc = pROC::roc(PDAC_v_symptomatic$y,PDAC_v_symptomatic$dv_mean, plot = TRUE, print.auc = TRUE, main =
paste0(my_main,": ","Array data, PDAC vs. Symptomatic"))
         points(.95,.8, pch = 20, col = "red")
         lines(x = c(1,.95,.95), y = c(.8,.8,1), col = "red",lty = "dotted")
      pvs_sig_roc_ca = pROC::roc(PDAC_v_symptomatic$y,PDAC_v_symptomatic$ca19_9_dv_mean, plot = TRUE, print.auc =
TRUE,
main = paste0(my_main,": ","Array + CA19-9, PDAC vs. Symptomatic"))
         points(.95,.8, pch = 20, col = "red")
```

TABLE 7-continued

SVM script

```
        lines(x = c(1,.95,.95), y = c(.8,.8,1), col = "red",lty = "dotted")
        pvs_sig_roc_caonly = pROC::roc(PDAC_v_symptomatic_ca$dx,PDAC_v_symptomatic_ca$ca19_9, plot = TRUE, print.auc =
TRUE, main = paste0(my_main,": ","CA19-9, PDAC vs. Symptomatic"))
        points(.95,.8, pch = 20, col = "red")
        lines(x = c(1,.95,.95), y = c(.8,.8,1), col = "red",lty = "dotted")
    }
    # PDAC v Early stage
    Early_PDAC_v_Ctrl = subset(sub_roc_data, y == "Control" | stage_grp == "Early")
    Early_PDAC_v_Ctrl_ca = subset(dataset, dx == "Control" | stage_grp == "Early") %>% select(ca19_9,dx)
    if(length(unique(Early_PDAC_v_Ctrl$y ))>1){
        pve_sig_roc = pROC::roc(Early_PDAC_v_Ctrl$y, Early_PDAC_v_Ctrl$dv_mean, plot = TRUE, print.auc = TRUE, main =
paste0(my_main,": ","Array data, Early PDAC vs. Ctrls"))
        points(.95,.8, pch = 20, col = "red")
        lines(x = c(1,.95,.95), y = c(.8,.8,1), col = "red",lty = "dotted")
        pve_sig_roc_ca = pROC::roc(Early_PDAC_v_Ctrl$y,Early_PDAC_v_Ctrl$ca19_9_dv_mean, plot = TRUE, print.auc = TRUE,
main = paste0(my_main,": ","Array + CA19-9, Early PDAC vs. Ctrls"))
        points(.95,.8, pch = 20, col = "red")
        lines(x = c(1,.95,.95), y = c(.8,.8,1), col = "red",lty = "dotted")
        pve_sig_roc_caonly = pROC::roc(Early_PDAC_v_Ctrl_ca$dx,Early_PDAC_v_Ctrl_ca$ca19_9, plot = TRUE, print.auc = TRUE,
main = paste0(my_main,": ","CA19-9, Early PDAC vs. Ctrls"))
        points(.95,.8, pch = 20, col = "red")
        lines(x = c(1,.95,.95), y = c(.8,.8,1), col = "red",lty = "dotted")
    }
    AUC_RES = tibble(
        Type = "ROC_AUC",
        all = all_sig_roc$auc[1],
        all_ca = all_sig_roc_ca$auc[1],
        all_ca_only = all_sig_roc_caonly$auc[1],
        pvh = pvh_sig_roc$auc[1],
        pvh_ca = pvh_sig_roc_ca$auc[1],
        pvh_ca_only = pvh_sig_roc_caonly$auc[1],
        pvs = pvs_sig_roc$auc[1],
        pvs_ca = pvs_sig_roc_ca$auc[1],
        pvs_ca_only = pvs_sig_roc_caonly$auc[1],
        pve = pve_sig_roc$auc[1],
        pve_ca = pve_sig_roc_ca$auc[1],
        pve_ca_only = pve_sig_roc_caonly$auc[1]
    )
    SEN_RES = tibble(
        Type = "Sensitivity",
        all = thresh_to_sen(all_sig_roc,threshold_sig),
        all_ca = thresh_to_sen(all_sig_roc_ca,threshold_sig_CA19),
        all_ca_only = thresh_to_sen(all_sig_roc_caonly,threshold_CA19),
        pvh = thresh_to_sen(pvh_sig_roc,threshold_sig),
        pvh_ca = thresh_to_sen(pvh_sig_roc_ca,threshold_sig_CA19),
        pvh_ca_only = thresh_to_sen(pvh_sig_roc_caonly,threshold_CA19),
        pvs = thresh_to_sen(pvs_sig_roc,threshold_sig),
        pvs_ca = thresh_to_sen(pvs_sig_roc_ca,threshold_sig_CA19),
        pvs_ca_only = thresh_to_sen(pvs_sig_roc_caonly,threshold_CA19),
            pve = thresh_to_sen(pve_sig_roc,threshold_sig),
        pve_ca = thresh_to_sen(pve_sig_roc_ca,threshold_sig_CA19),
        pve_ca_only = thresh_to_sen(pve_sig_roc_caonly,threshold_CA19)
    )
    SPE_RES = tibble(
        Type = "Specificity",
        all = thresh_to_spe(all_sig_roc,threshold_sig),
        all_ca = thresh to spe(all_sig_roc_ca,threshold_sig_CA19),
        all_ca_only = thresh_to_spe(all_sig_roc_caonly,threshold_CA19),
        pvh = thresh_to_spe(pvh_sig_roc,threshold_sig),
        pvh_ca = thresh_to_spe(pvh_sig_roc_ca,threshold_sig_CA19),
        pvh_ca_only = thresh_to_spe(pvh_sig_roc_caonly,threshold_CA19),
        pvs = thresh_to_spe(pvs_sig_roc,threshold_sig),
        pvs_ca = thresh_to_spe(pvs_sig_roc_ca,threshold_sig_CA19),
        pvs_ca_only = thresh_to_spe(pvs_sig_roc_caonly,threshold_CA19),
        pve = thresh_to_spe(pve_sig_roc,threshold_sig),
        pve_ca = thresh_to_spe(pve_sig_roc_ca,threshold_sig_CA19),
        pve_ca_only = thresh_to_spe(pve_sig_roc_caonly,threshold_CA19)
    )
    SEN_SEP_RES = rbind(AUC_RES,SPE_RES,SEN_RES)
    return(SEN_SEP_RES)
}
```

Example 2

Objective: To validate the clinical predictive performance of the 8-plex antibody microarray-based biomarker panel in combination with CA19-9 intended for early detection of pancreatic ductal adenocarcinoma (PDAC).

Study design: The validation was performed as a blinded case-control study comprising 591 serum samples prospectively collected at 11 sites in USA and Europe. Samples were derived from 167 PDAC patients, 203 individuals at risk of hereditary or familial pancreatic cancer (FPC) and 221 healthy individuals, respectively.

Main outcome measures: Sensitivity, specificity, and positive and negative predictive values of the locked test model for detection of PDAC.

Results: The panel of eight serum biomarkers, in combination with CA19-9 assessment, effectively separated early-stage PDAC (stage I/II) patients from individuals belonging to the hereditary/FPC risk group with a specificity of 98% and a sensitivity of 85%. A specificity of 98% and a sensitivity of 87% were achieved when samples of all PDAC stages (stage I-IV) were included in the classification.

Conclusions: Using a blinded experimental protocol on a prospective multicenter collection of serum samples, we show that the validated clinical performance of our newly proposed biomarker panel is consistent with the results seen along the development pathway. The established classifier meets the requirements of a clinically useful test for identifying an individual at risk of having pancreatic cancer already in the early stage of disease.

Introduction

Pancreatic ductal adenocarcinoma (PDAC) is an aggressive malignancy with a high rate of mortality. PDAC is the fourth most common cause of cancer death in the US with an estimate of 60,000 incident cases and 48,000 deaths in 2021 (Siegel et al, 2021). Less than 10% of patients survive 5 years after diagnosis (Ilic and Ilic, 2016). The main reason for this poor outcome is that only 10-20% of patients present with resectable disease at diagnosis, while the majority (50-60%) of patients have metastatic disease (Scheufele et al, 2019).

It is crucial to identify individuals at high risk of developing PDAC so preventive and early detection measures can be employed. The 5-year survival has been reported to be as great as 40% if the disease can be detected when it is still localized to the pancreas, mainly due to a higher number of surgically resectable tumors (Matsuno et al, 2004).

While most pancreatic cancers arise sporadically, a subset of neoplasms develop in patients with hereditary and familial predisposition. The familial or hereditary form of the disease accounts for 10 to 15% of cases (Copur et al, 2020). Several germline mutations have been shown to be associated with an increased risk of PDAC. For example, germline mutations involving BRCA1, BRCA2, CDKN2A and mismatch repair genes predispose patients to PDAC (Petersen, 2016). Familial pancreatic cancer (FPC) is defined as having ≥2 first-degree relatives that had the disease, without an association to a known causative germline mutation or hereditary genetic syndrome. FPC accounts for 4 to 10% of PDAC cases (Copur et al, 2020).

This Example describes a completely independent blinded validation of the aggregate 9-biomarker signature (including CA19-9) from the first Example using a prospectively collected set of PDAC and control samples. To demonstrate clinical usefulness of the test, a large proportion of the control samples have been derived from subjects that belong to the hereditary and FPC risk group. This study relates to the ongoing clinical trial designated PanFAM-1 (clinicaltrials.gov).

Methods

Sample Collection

All serum samples were prospectively collected through our study collaborators between 2019 and 2021 at eleven pancreatic disease reference sites in USA and Europe. The US sites contributing with samples in this study were Mount Sinai School of Medicine, Beth Israel Deaconess Medical Center, University of Pittsburgh Medical Center, BioIVT LLC., Discovery Life Sciences Inc., Massachusetts General Hospital and University of Pennsylvania. The sites in Europe contributing with samples were Sahlgrenska University Hospital and Växjö Central Hospital in Sweden, Helsinki University Hospital in Finland, and Ramón y Cajal University Hospital in Spain.

Demographic Information

The samples comprised 167 PDAC (whereof 56 stage I and II), 203 hereditary/FPC risk group controls and 221 healthy controls, respectively. The median age of donors was 70 for PDAC samples, 59 for hereditary/FPC risk group controls and 49 for healthy controls. The gender distribution for donors of PDAC samples were 58% male/42% female, 36% male/64% female for donors from the hereditary/FPC risk group, and 52% male/48% female for healthy controls.

Sample Randomization and Blinding

Serum samples were blinded to laboratory technicians, the laboratory director and the medical director until results were finalized. In addition, the order of samples was randomized within batches for biotinylation and microarray analysis to minimize analytical bias.

CA19-9 Assay

Serum CA19-9 levels were measured by a cobas e411 analyzer (Roche Diagnostics, Mannheim, Germany) using the electrochemiluminescence immunoassay technology. All CA19-9 assays were performed according to the manufacturer's instructions using a validated instrument and a defined SOP.

Sample Biotinylation

The serum samples were labeled with biotin in duplicate. Briefly, the serum was diluted 1:9 in PBS to a total protein concentration of approximately 8 g/l and labeled with 1.1 mM EZ-Link NHS-PEG4-Biotin (Thermo Fisher Scientific). The biotinylation was allowed to proceed for two hours at 4° C. and then quenched with the addition of 0.5M Tris-HCl, pH 8.0. The labeled serum samples were aliquoted and stored at −20° C. until further analysis.

Antibody Microarray Production

The antibody microarrays consisted of eight recombinant scFvs directed against various tumour antigens and complement system components. His-tagged scFvs were produced in the periplasm of *E. coli* and purified by immobilized metal ion affinity chromatography (IMAC) using His MultiTrap HP 96-well filter plates (GE Healthcare Life Science). The elution buffer was exchanged for PBS, using Zeba™ Spin desalting 96-well spin plates with 7K MWCO resins (Thermo Fisher Scientific). Protein concentration was estimated using a Pierce Coomassie (Bradford) protein assay kit (Thermo Fisher Scientific). Protein purity was assessed by SDS-PAGE using 8-16% Criterion TGX Stain-Free gels (Bio-Rad). Antibody microarrays were produced on black MaxiSorp slides (Nunc, Thermo Fisher Scientific), using a non-contact printer (sciFLEXARRAYER SX; Scienion). The array layout was printed using spot-on-the-fly option and with one PDC (glass piezo dispense capillary). Twelve identical arrays were printed on each slide in two columns of seven arrays.

Each array consisted of 6×10 spots with 350 μm spot-to-spot center distance and a spot diameter of 140 μm. Each array consisted of three identical segments. All scFvs were printed in six spot replicates with two replicates in each segment. The on-chip scFv concentrations ranged from 52 to 217 μg/mL depending on binding properties of the individual clones. In addition, on each array, six replicates of a negative control (PBS) and six replicates of a reference marker (biotinylated BSA) were spotted. Printed microarray slides were stored in dark in a climate-controlled room, at 22° C. and 40% relative humidity, for at least 5 days before being used in microarray assays.

Microarray Assay

In general, six patient samples were analysed in duplicate on each microarray slide. On each assay run, two microarray slides were dedicated for quality control (QC) and normalization purposes.

Each microarray slide was mounted in a hybridization gasket (Schott) and blocked with 1% w/v milk, 1% v/v Tween-20 in sterile PBS (MT-PBS) at room temperature (RT) for 2 hours with constant agitation. Meanwhile, aliquots of labelled serum samples were thawed on ice and subsequently diluted 1:50 in MT-PBS. The slides were washed four times with 0.05% Tween-20 in sterile PBS (T-PBS) followed by addition of diluted serum samples to the wells of the gasket.

Samples were incubated on the slides at RT for 2 hours with constant agitation. Next, the slides were washed four times with T-PBS, incubated with 1 µg/ml Streptavidin Alexa-647 (Life Technologies) in MT-PBS at RT for 1 hour with constant agitation, and again washed four times with T-PBS. Finally, the slides were dismounted from the gaskets, immersed in water and dried under a stream of $N_2$. The slides were immediately scanned with a microarray fluorescence scanner, InnoScan 710 AL (Innopsys), at a laser excitation wavelength of 635 nm using a resolution of 10 µm/pixel.

Data Acquisition, Normalization and Quality Control

Data acquisition, normalization and quality control was generated automatically by our in-house, proprietary software platform, Immunovia Evaluation System LDT (IES LDT). In more detail, grid alignment and spot signal quantitation were performed using the fixed circle method.

Each data point represented the median, background-subtracted, signal of six replicate spots unless any replicate(s) did not pass the applied z-filtering acceptance criteria and was flagged as a position failure. In this case, the worst performing replicate(s) was eliminated and the median value of the remaining replicates was used instead. Log 2 values of signal intensities were used, and no imputation was applied on the data.

Batch to batch variation was handled by automated calculation of normalization factors for each microarray assay batch, per each scFv antibody. These factors were based on the signals for six serum pools (three from healthy individuals and three from PDAC patients, respectively) placed on the dedicated QC slides.

Several quality control (QC) steps were automatically applied both before and after normalization and only samples passing the QC steps were further evaluated. In total, a single sample was removed and the final data set contained data from 591 individuals.

CA19-9 assay data was added into the dataset, and sample results in terms of a decision value (DV) for each patient sample were automatically calculated based on the 8-plex biomarker signature and the CA19-9 value. The results were automatically uploaded to Orchard Harvest Laboratory Information System (Orchard Software Corporation) for un-blinding and final result verification.

Data Analysis

Sensitivity, specificity, and positive and negative predictive values (PPV and NPV respectively) were calculated using predefined and locked model algorithm and a DV cut-off for sample classification. Receiver operating characteristic (ROC) curves, and the corresponding area under the curve (AUC) values, were calculated for the different diagnostic groups using the previously established and locked model algorithm.

Results

A total of 58 samples fell in the defined DV borderline range of the model algorithm and could not be assigned a classification. All other samples were successfully assayed and classified. This left 144 PDAC (whereof 46 stage I and II), 183 familial/hereditary controls and 206 healthy controls for analysis after completion of the study and unblinding of the sample information.

The results of the validation study were assessed by generating ROC curves for various group comparisons and the corresponding AUC values were calculated when combining data from the 8-plex microarray analysis with that from the CA19-9 assay. FIGS. 7-8 show an AUC value of 0.94 for classification of PDAC all stages (I-IV), and an AUC value of 0.92 for PDAC early stages (I/II), vs. controls belonging to the hereditary/FPC risk group, respectively. Applying the pre-defined model cut-off, a sensitivity of 87% and specificity of 98% are achieved for the comparison including all stages of PDAC, and most importantly, data yields a sensitivity of 85% and specificity of 98% for differentiating early PDAC patients from the individuals at risk of hereditary or FPC (but currently free of malignant disease) (Table 8).

TABLE 8

Results of the blind validation study

| PDAC vs familial/<br>hereditary controls | Stage I & II PDAC | All stages PDAC |
| --- | --- | --- |
| Sensitivity | 84.8% | 86.8% |
| Specificity | 98.4% | 98.4% |
| NPV (3% prevalence) | 99.5% | 99.6% |
| PPV (3% prevalence) | 62.1% | 62.7% |
| NPV (1% prevalence) | 99.8% | 99.9% |
| PPV (1% prevalence) | 34.9% | 35.4% |

FIGS. 9-10 show the corresponding ROC curves and AUC values for differentiating the PDAC samples from healthy controls (HC). The AUC values of 0.95 (PDAC stage I-IV vs. HC) and 0.93 (PDAC stage I/II vs. HC) are in good concordance with what has been observed during the development of the test (Mellby et al, 2018).

Moreover, we have assessed the positive and negative predictive values (PPV and NPV) of the test (Table 8). The PPV and NPV are related to the sensitivity and specificity through the prevalence of the disease (Trevethan, 2017). Depending on the particular genetic syndrome or the number of first-degree relatives diagnosed with PDAC, the prevalence can vary from 1-3% for the population at risk for hereditary/FPC. In Table 8, we show the result of calculations of PPV and NPV for the test at a prevalence of 1% and 3%, respectively. At 3% prevalence, the PPV is 62% for detection of early stage (I/II) PDAC. Since PPV is directly proportional to the prevalence, the value is significantly lower at 1%. The NPV for the detection of early stage (I/II) PDAC is high (99.5 and 99.8%) at both levels of prevalence.

FIG. 11 shows the distribution of decision values for the samples from the PDAC patients, the individuals at risk of hereditary or familial pancreatic cancer and the healthy donors, respectively. The DV is the output score of the test model that in conjunction with the cut-off value will inform whether a patient sample is positive or negative for PDAC. Interestingly, there is a clear distinction between PDAC and the other two groups, but a significant overlap between the individuals at risk of hereditary or familial pancreatic cancer and the healthy donors, although the aggregate health status is worse for the individuals in the risk group. There is a wide distribution of decision values for the patients with PDAC that could reflect the presence of different stages and the genetically heterogeneous nature of the disease (Juiz et al, 2019).

Discussion

In recent years, there has been an increased awareness of the benefits of germline genetic testing and family history analysis of PDAC patients to help to identify high-risk individuals (broadly defined as those with a lifetime risk greater than 5%). The general average lifetime risk of developing pancreatic cancer is too low (approximately 1.6% in the USA) for population-based screening. As a comparison, the estimated lifetime risk of developing pancreatic cancer for an individual with two first-degree relatives affected by the disease is around 8% (Klein et al, 2004). Identification of high-risk individuals provides an opportunity to detect PDAC at a potentially curative stage.

However, there is currently no general agreement on which groups of patients and individuals that should be eligible for pancreatic surveillance and screening. In 2020, the Cancer of the Pancreas Screening (CAPS) consortium released an update of their consensus guidelines for pancreatic cancer screening based on the clinical experiences of 49 multidisciplinary experts (Goggins et al, 2020). The consortium recommends screening in the following high-risk groups: Individuals who have at least one first-degree relative with pancreatic cancer who in turn also has a first-degree relative with pancreatic cancer, all patients with Peutz-Jeghers syndrome, all carriers of a germline CDKN2A mutation, and carriers of a germline BRCA1, BRCA2, PALB2, ATM, MLH1, MSH2, or MSH6 gene mutation with at least one affected first-degree blood relative.

Surveillance of individuals at high-risk of PDAC would typically include endoscopic ultrasound, computerised tomography and/or magnetic resonance imaging. Our validated test may serve in conjunction with these imaging methods to confirm or establish diagnosis. A test that can both increase the number of cancer cases referred to a specialist and increase the prevalence of cancers within that referred population, by minimizing the number of benign referrals, ought to be very useful.

To sum up, data from this blinded validation study demonstrates that our 8-plex antibody microarray assay, in combination with CA19-9 measurement, detects PDAC at an early stage (stage I&II) with a specificity of 98% and sensitivity of 85%. These results hold the potential of significantly expanding therapeutic possibilities and improving outcomes for patients affected by this devastating disease.

Additional References for Example 2

Copur M S, Talmon G A, Wedel W, Hart J D, Merani S, Vargasi L M (2020) Hereditary vs Familial Pancreatic Cancer: Associated Genetic Syndromes and Clinical Perspective. *Oncology* (Williston Park) 34(6): 196-201.

Goggins M, Overbeek K A, Brand R, Syngal S, Del Chiaro M, Bartsch D K, Bassi C, Carrato A, Farrell J, Fishman E K, Fockens P, Gress T M, van Hooft J E, Hruban R H, Kastrinos F, Klein A, Lennon A M, Lucas A, Park W, Rustgi A, Simeone D, Stoffel E, Vasen H F A, Cahen D L, Canto M I and Bruno M (2020) International Cancer of the Pancreas Screening (CAPS) consortium. Management of patients with increased risk for familial pancreatic cancer: updated recommendations from the International Cancer of the Pancreas Screening (CAPS) Consortium. *Gut* 69(1): 7-17.

Juiz N A, Iovanna J and Dusetti N (2019) Pancreatic Cancer Heterogeneity Can Be Explained Beyond the Genome. *Front Oncol.* 2019 9: 246.

Klein A P, Brune K A, Petersen G M, Goggins M, Tersmette A C, Offerhaus G J, Griffin C, Cameron J L, Yeo C J, Kern S, Hruban R H (2004) Prospective risk of pancreatic cancer in familial pancreatic cancer kindreds. *Cancer Res.* 64(7): 2634-8.

Matsuno S, Egawa S, Fukuyama S, Motoi F, Sunamura M, Isaji S, Imaizumi T, Okada S, Kato H, Suda K, Nakao A, Hiraoka T, Hosotani R and Takeda K (2004) Pancreatic Cancer Registry in Japan: 20 years of experience. *Pancreas* 28(3): 219-30.

Scheufele F, Hartmann D and Helmut Friess (2019) Treatment of pancreatic cancer-neoadjuvant treatment in borderline resectable/locally advanced pancreatic cancer. *Transl Gastroenterol Hepatol.* 4(32).

Petersen G M (2016) Familial pancreatic cancer. *Semin Oncol.* 43(5): 548-553.

Siegel R L, Miller K D, Fuchs H E and Jemal A (2021) Cancer Statistics, 2021. *CA Cancer J Clin.* 71(1): 7-33.

Trevethan R. (2017) Sensitivity, Specificity, and Predictive Values: Foundations, Pliabilities, and Pitfalls in Research and Practice. *Front Public Health* 5:307.

The invention claimed is:

1. A method for diagnosing pancreatic cancer comprising the steps of:
   (a) providing a serum or plasma sample from a human individual to be tested;
   (b) measuring the amount in the test sample of the biomarkers: (i) osteoprotegerin (OPG) and/or von Willebrand factor (VWF); (ii) gelsolin (GSN) and/or 3-hydroxyacyl-CoA dehydrogenase type-2 (HADH2); (iii) insulin-like growth factor-binding protein 3 (IG-FBP3); (iv) Complement Factor B; (v) mucin 16 (MUC16), ficolin-2 (FCN2) and/or mannan-binding lectin serine protease 2 (MASP2); (vi) Complement C4; (vii) Complement C5; (viii) Cystatin C; and (ix) CA 19-9; and
   (c) treating the individual diagnosed with pancreatic cancer with pancreatic cancer chemotherapy, pancreatic cancer immunotherapy, and/or surgical removal of the pancreas in whole or in part,
   where the amount in the test sample of the biomarkers recited in step (b) is indicative of pancreatic cancer in the individual by applying a supervised learning algorithm to the measured amount of the biomarkers measured in step b), wherein the supervised learning algorithm has been trained using biomarker profiles from:
   (i) individuals known to have pancreatic cancer; and
   (ii) individuals known to be healthy and/or symptomatic individuals without pancreatic cancer.

2. The method according to claim 1, wherein the pancreatic cancer is early pancreatic cancer or pancreatic ductal adenocarcinoma.

3. The method according to claim 1, wherein the pancreatic cancer is stage I or stage II pancreatic cancer.

4. The method according to claim 1, wherein the sample in step (a) is from an individual in one or more of the following risk groups:
   (i) individuals with a family history of pancreatic cancer or Peutz-Jeghers syndrome, familial atypical multiple mole melanoma syndrome, Lynch syndrome, BRCA1 mutations and/or BRCA2 mutations;
   (ii) individuals diagnosed with diabetes;
   (iii) individuals with symptoms suggestive or consistent with pancreatic cancer; and/or
   (iv) individuals with a benign pancreatic or biliary disease.

5. The method according to claim 1, wherein step (b) comprises measuring the amount of OPG, GSN, IGFBP3, Complement Factor B, MUC16, Complement C4, Complement C5, Cystatin C, CA 19-9 and/or the presence or amount of one or more secondary targets thereof.

6. The method according to claim 1, wherein step (b) comprises measuring the amount of OPG, GSN, IGFBP3, Complement Factor B, MUC16, Complement C4, Complement C5, Cystatin C, CA 19-9.

7. The method according to claim 1, wherein step (b) further comprises measuring the presence and/or amount of one or more biomarker selected from the group consisting of TGF-β1, IFN-γ, PSA, C3, C1 esterase inhibitor, Properdin, VEGF, CD40, Apolipoprotein A1, MYOM2, CHX10, BTK, MATK, TNFRSF3, UBC9, UBP7, APLF, MARK1-1, PTPRN2, CEACAM-5, MMP9, IL-2Ra, AGR2, IGFBP2, GDF-15, and CEACAM-5.

8. The method according to claim 1, further comprising the steps of:
   (d) providing one or more control samples from:
      (i) an individual not afflicted with pancreatic cancer; and/or
      (ii) an individual afflicted with a benign pancreatic and/or biliary disease; and
   (e) determining a biomarker signature of the one or more control samples by measuring the amount in the control sample of the biomarkers measured in step (b);
   wherein the pancreatic cancer is identified in the event that the amount in the test sample of the biomarkers measured in step (b) is different from the amount in the control sample of the biomarkers measured in step (e).

9. The method according to claim 1, further comprising the steps of:
   (d) providing one or more control samples from an individual afflicted with pancreatic cancer; and
   (e) determining a biomarker signature of the control sample by measuring the amount in the control sample of the biomarkers measured in step (b);
   wherein the pancreatic cancer is identified in the event that the amount in the test sample of the biomarkers measured in step (b) corresponds to the amount in the control sample of biomarkers measured in step (e).

10. The method according to claim 1, wherein step (b) comprises measuring the expression of the protein or polypeptide of the biomarkers (i) OPG and/or VWF; (ii) GSN and/or HADH2; (iii) IGFBP3; (iv) Complement Factor B; (v) MUC16, FCN2 and/or MASP2; (vi) Complement C4; (vii) Complement C5; and (viii) Cystatin C.

11. The method according to claim 1, wherein step (b) comprises using an antibody or an antigen-binding fragment thereof comprising SEQ ID NO: 15, SEQ ID NO: 6, SEQ ID NO: 11, SEQ ID NO: 13, SEQ ID NO: 20, SEQ ID NO: 32, SEQ ID NO: 30, or SEQ ID NO: 36,
   optionally wherein said antibody or an antigen-binding fragment thereof is immobilised on a surface and/or labelled with a detectable moiety.

12. The method according to claim 1, wherein step (b) comprises using an antibody or an antigen-binding fragment thereof comprising SEQ ID NO: 30, 32, or 36.

13. The method according to claim 1, wherein step (b) comprises:
   (i) labelling biomarkers present in the sample with biotin;
   (ii) contacting the biotin-labelled proteins with an array comprising a plurality of scFv immobilised at discrete locations on its surface, the scFv having specificity for the biomarkers recited in step (b);
   (iii) contacting the biotin-labelled proteins immobilised on the scFv with a streptavidin conjugate comprising a fluorescent dye; and
   (iv) detecting the presence of the dye at discrete locations on the array surface,
   wherein the expression of the dye on the array surface is indicative of the expression of a biomarker in the sample.

14. The method according to claim 1, wherein step (c) comprises surgical removal of the pancreas in whole or in part combined with chemotherapy.

15. The method according to claim 1, wherein the pancreatic cancer chemotherapy is selected from the group consisting of: AC chemotherapy; Capecitabine and docetaxel chemotherapy; CMF chemotherapy; Cyclophosphamide; EC chemotherapy; ECF chemotherapy; E-CMF chemotherapy (Epi-CMF); Eribulin; FEC chemotherapy; FEC-T chemotherapy; Fluorouracil (5FU); GemCarbo chemotherapy; Gemcitabine; Gemcitabine and cisplatin chemotherapy (GemCis or GemCisplat); GemTaxol chemotherapy; Idarubicin; Liposomal doxorubicin; Mitomycin; Mitoxantrone; MM chemotherapy; MMM chemotherapy; Paclitaxel; TAC chemotherapy; Taxotere and cyclophosphamide (TC) chemotherapy; Vinblastine; Vincristine; Vindesine; Vinorelbine; and a combination of folinic acid, fluorouracil, irinotecan, and oxaliplatin.

16. The method according to claim 1, wherein the pancreatic cancer chemotherapy is selected from the group consisting of: Fluorouracil (5FU); Gemcitabine; Gemcitabine and cisplatin chemotherapy (GemCis or GemCisplat); Paclitaxel; TAC chemotherapy; Taxotere and cyclophosphamide (TC) chemotherapy; and a combination of folinic acid, fluorouracil, irinotecan, and oxaliplatin.

17. The method according to claim 1, wherein step (c) comprises treating the individual with a pancreatic cancer chemotherapy.

18. A method for diagnosing pancreatic cancer comprising the steps of:
   (a) providing a serum or plasma sample from a human individual to be tested;
   (b) measuring the amount in the test sample of the biomarkers: (i) osteoprotegerin (OPG) and/or von Willebrand factor (VWF); (ii) gelsolin (GSN) and/or 3-hydroxyacyl-CoA dehydrogenase type-2 (HADH2) ; (iii) insulin-like growth factor-binding protein 3 (IGFBP3); (iv) Complement Factor B; (v) mucin 16 (MUC16) , ficolin-2 (FCN2) and/or mannan-binding lectin serine protease 2 (MASP2); (vi) Complement C4; (vii) Complement C5; (viii) Cystatin C; and (ix) CA 19-9; and
   (c) treating the individual diagnosed with pancreatic cancer with pancreatic cancer chemotherapy, pancreatic cancer immunotherapy, and/or surgical removal of the pancreas in whole or in part,
   wherein an increase in the amount in the test sample of (i) osteoprotegerin (OPG) and/or von Willebrand factor (VWF); (iv) Complement Factor B; (vi) Complement C4; (vii) Complement C5; (viii) Cystatin C; and (ix) CA 19-9 compared to a negative control; and a decrease in the amount in the test sample of (ii) gelsolin (GSN) and/or 3-hydroxyacyl-CoA dehydrogenase type-2 (HADH2); (iii) insulin-like growth factor-binding protein 3 (IGFBP3); and (v) mucin 16 (MUC16) , ficolin-2 (FCN2) and/or mannan-binding lectin serine protease 2 (MASP2) compared to a negative control is indicative of pancreatic cancer in the individual,
   wherein the negative control is a serum or plasma sample from: (i) an individual not afflicted with pancreatic cancer; and/or (ii) an individual afflicted with a benign pancreatic and/or biliary disease.

* * * * *

SEQUENCE LISTING

```
<160> NUMBER OF SEQ ID NOS: 38

<210> SEQ ID NO 1
<211> LENGTH: 267
<212> TYPE: PRT
<213> ORGANISM: Artificial Sequence
<220> FEATURE:
<223> OTHER INFORMATION: TGF-beta1 (1)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45
```

```
Ala Val Val Ser Ile Asp Gly Gly Thr Thr Tyr Tyr Gly Asp Pro Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Arg Gly Pro Thr Leu Thr Tyr Tyr Phe Asp Tyr Trp Gly Gln Gly
                100                 105                 110

Thr Leu Val Thr Val Ser Ser Gly Gly Gly Gly Ser Gly Gly Gly Gly
            115                 120                 125

Ser Gly Gly Gly Gly Ser Gln Ser Val Leu Thr Gln Pro Pro Ser Ala
130                 135                 140

Ser Gly Thr Pro Gly Gln Arg Val Thr Ile Ser Cys Ser Gly Ser Ser
145                 150                 155                 160

Ser Asn Ile Gly Ser Asn Thr Val Asn Trp Tyr Gln Gln Leu Pro Gly
                165                 170                 175

Thr Ala Pro Lys Leu Leu Ile Tyr Ser Asn Asn Gln Arg Pro Ser Gly
                180                 185                 190

Val Pro Asp Arg Phe Ser Gly Ser Lys Ser Gly Thr Ser Ala Ser Leu
            195                 200                 205

Ala Ile Ser Gly Leu Arg Ser Glu Asp Glu Ala Asp Tyr Tyr Cys Gln
210                 215                 220

Ser Tyr Asp Ser Ser Leu Ser Gly Trp Val Phe Gly Gly Gly Thr Lys
225                 230                 235                 240

Leu Thr Val Leu Gly Glu Gln Lys Leu Ile Ser Glu Glu Asp Leu Ser
                245                 250                 255

Gly Ser Ala Ala Ala His His His His His His
                260                 265

<210> SEQ ID NO 2
<211> LENGTH: 266
<212> TYPE: PRT
<213> ORGANISM: Artificial Sequence
<220> FEATURE:
<223> OTHER INFORMATION: IFN-gamma (2)

<400> SEQUENCE: 2

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Arg His
                 20                  25                  30

Gly Phe His Trp Val Arg Gln Gly Pro Gly Lys Gly Leu Glu Trp Val
             35                  40                  45

Ser Gly Val Ser Trp Asn Gly Ser Arg Thr His Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Asn Trp Tyr Arg Ala Phe Asp Ile Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gln Ser Val Leu Thr Gln Pro Pro Ser Ala Ser
                130                 135                 140
```

```
Gly Thr Pro Gly Gln Arg Val Thr Ile Ser Cys Ser Gly Gly Ser Ser
145                 150                 155                 160

His Ile Gly Arg Asn Phe Ile Ser Trp Tyr Gln Gln Leu Pro Gly Thr
                165                 170                 175

Ala Pro Lys Leu Leu Ile Tyr Ala Gly Asn Ser Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Arg Ser Glu Asp Glu Ala Asp Tyr Tyr Cys Ala Ala
210                 215                 220

Trp Asp Asp Ser Leu Ser Gly Val Val Phe Gly Gly Gly Thr Lys Leu
225                 230                 235                 240

Thr Val Leu Gly Glu Gln Lys Leu Ile Ser Glu Glu Asp Leu Ser Gly
            245                 250                 255

Ser Ala Ala Ala His His His His His His
            260                 265

<210> SEQ ID NO 3
<211> LENGTH: 269
<212> TYPE: PRT
<213> ORGANISM: Artificial Sequence
<220> FEATURE:
<223> OTHER INFORMATION: PSA

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Glu Met Asn Trp Val Arg Gln Ala Pro Gly Lys Gly Leu Glu Trp Val
        35                  40                  45

Ala Val Ile Gly Gly Asn Gly Val Asp Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Val Arg Glu Glu Val Asp Phe Trp Ser Gly Tyr Tyr Ser Tyr Gly Met
            100                 105                 110

Asp Val Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Ser Val Leu
130                 135                 140

Thr Gln Pro Pro Ser Ala Ser Gly Thr Pro Gly Gln Arg Val Thr Ile
145                 150                 155                 160

Ser Cys Ser Gly Ser Ser Ser Asn Ile Gly Asp Asn Phe Val Ser Trp
                165                 170                 175

Tyr Gln Gln Leu Pro Gly Thr Ala Pro Lys Leu Leu Ile Tyr Arg Thr
            180                 185                 190

Asn Gly Arg Pro Ser Gly Val Pro Asp Arg Phe Ser Gly Ser Lys Ser
        195                 200                 205

Gly Thr Ser Ala Ser Leu Ala Ile Ser Gly Leu Arg Ser Glu Asp Glu
210                 215                 220

Ala Asp Tyr Tyr Cys Ala Thr Trp Asp Asp Asn Leu Asn Gly Arg Val
225                 230                 235                 240
```

```
Val Phe Gly Gly Gly Thr Lys Leu Thr Val Leu Gly Asp Tyr Lys Asp
                245                 250                 255

Asp Asp Asp Lys Ala Ala His His His His His His
        260                 265

<210> SEQ ID NO 4
<211> LENGTH: 268
<212> TYPE: PRT
<213> ORGANISM: Artificial Sequence
<220> FEATURE:
<223> OTHER INFORMATION: C3 (1)

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Val Thr Gly Ser Gly Gly Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Arg Trp Phe Gly Asn Asp Ala Phe Asp Ile Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gln Ser Val Leu Thr Gln Pro Pro Ser
    130                 135                 140

Ala Ser Gly Thr Pro Gly Gln Arg Val Thr Ile Ser Cys Ser Gly Ser
145                 150                 155                 160

Ala Ser Asn Leu Gly Met His Phe Val Ser Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Thr Leu Asn Ile Trp Val Phe Gly Gly Gly Thr
225                 230                 235                 240

Lys Leu Thr Val Leu Gly Glu Gln Lys Leu Ile Ser Glu Glu Asp Leu
                245                 250                 255

Ser Gly Ser Ala Ala Ala His His His His His
            260                 265

<210> SEQ ID NO 5
<211> LENGTH: 270
<212> TYPE: PRT
<213> ORGANISM: Artificial Sequence
<220> FEATURE:
<223> OTHER INFORMATION: C3 (2)
```

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Arg Met Ile Trp Val Arg Gln Ala Pro Gly Lys Gly Leu Glu Trp Val
        35                  40                  45

Ser Ser Ile Ser Gly Ser Asn Thr Tyr Ile His Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg His Pro Leu Leu Pro Ser Gly Met Asp Val Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Ala Ser Gly Thr Pro Gly Gln Arg Val Thr Ile Ser Cys Ser Gly
145                 150                 155                 160

Ser Ser Ser Asn Ile Gly Lys His Pro Val Asn Trp Tyr Gln Gln Leu
                165                 170                 175

Pro Gly Thr Ala Pro Lys Leu Leu Ile Tyr Arg Asn Asp Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
    210                 215                 220

Cys Gln Ser Tyr Asp Ser Ser Leu Ser Gly Ser Trp Val Phe Gly Gly
225                 230                 235                 240

Gly Thr Lys Leu Thr Val Leu Gly Glu Gln Lys Leu Ile Ser Glu Glu
                245                 250                 255

Asp Leu Ser Gly Ser Ala Ala Ala His His His His His
            260                 265                 270
```

<210> SEQ ID NO 6
<211> LENGTH: 265
<212> TYPE: PRT
<213> ORGANISM: Artificial Sequence
<220> FEATURE:
<223> OTHER INFORMATION: C5 (2)

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ser Met Asn Trp Val Arg Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                    85                  90                  95

Ala Arg Glu Asn Ser Gly Phe Phe Asp Tyr Trp Gly Gln Gly Thr Leu
                100                 105                 110

Val Thr Val Ser Ser Gly Gly Gly Ser Gly Gly Gly Ser Gly
            115                 120                 125

Gly Gly Gly Ser Gln Ser Val Leu Thr Gln Pro Pro Ser Ala Ser Gly
        130                 135                 140

Thr Pro Gly Gln Arg Val Thr Ile Ser Cys Thr Gly Ser Ser Ser Asn
145                 150                 155                 160

Ile Gly Ser Asn Thr Val Asn Trp Tyr Gln Gln Leu Pro Gly Thr Ala
                165                 170                 175

Pro Lys Leu Leu Ile Tyr Gly Asn Ser Asn Arg Pro Ser Gly Val Pro
            180                 185                 190

Asp Arg Phe Ser Gly Ser Lys Ser Gly Thr Ser Ala Ser Leu Thr Ile
            195                 200                 205

Ser Gly Leu Arg Ser Glu Asp Glu Ala Asp Tyr Tyr Cys Ala Ala Trp
        210                 215                 220

Asp Asp Ser Leu Ser Gly Trp Val Phe Gly Gly Gly Thr Lys Leu Thr
225                 230                 235                 240

Val Leu Gly Glu Gln Lys Leu Ile Ser Glu Glu Asp Leu Ser Gly Ser
                245                 250                 255

Ala Ala Ala His His His His His
            260                 265

<210> SEQ ID NO 7
<211> LENGTH: 268
<212> TYPE: PRT
<213> ORGANISM: Artificial Sequence
<220> FEATURE:
<223> OTHER INFORMATION: C1 inh. (1)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Gly Ile Ser Arg Gly Gly Glu Tyr Thr Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Gly Gly Leu Asp Ala Phe Asp Ile Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Arg Tyr Asp Val Gln Trp Tyr Gln Gln Leu Pro
                165                 170                 175

```
Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ser Trp Asp Asp Ser Leu Ser Gly Pro Val Phe Gly Gly Gly Thr
225                 230                 235                 240

Lys Leu Thr Val Leu Gly Glu Gln Lys Leu Ile Ser Glu Glu Asp Leu
                245                 250                 255

Ser Gly Ser Ala Ala Ala His His His His His His
            260                 265

<210> SEQ ID NO 8
<211> LENGTH: 269
<212> TYPE: PRT
<213> ORGANISM: Artificial Sequence
<220> FEATURE:
<223> OTHER INFORMATION: Properdin

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Tyr Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ser Gly Trp Tyr Asp Tyr Phe Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gln Ser Val Leu Thr Gln Pro Pro Ser
130                 135                 140

Ala Ser Gly Thr Pro Gly Gln Arg Val Thr Ile Ser Cys Thr Gly Ser
145                 150                 155                 160

Ser Ser Asn Ile Gly Ala Gly Tyr Asp Val His Trp Tyr Gln Gln Leu
                165                 170                 175

Pro Gly Thr Ala Pro Lys Leu Leu Ile Tyr Arg Asn Asn Gln Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
    210                 215                 220

Cys Ala Ala Trp Asp Asp Gly Leu Asn Ser Pro Val Phe Gly Gly Gly
225                 230                 235                 240

Thr Lys Leu Thr Val Leu Gly Glu Gln Lys Leu Ile Ser Glu Glu Asp
                245                 250                 255

Leu Ser Gly Ser Ala Ala Ala His His His His His His
            260                 265
```

-continued

```
<210> SEQ ID NO 9
<211> LENGTH: 269
<212> TYPE: PRT
<213> ORGANISM: Artificial Sequence
<220> FEATURE:
<223> OTHER INFORMATION: VEGF (3)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Gly Ile Ser Gly Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Glu Gly Tyr Gln Asp Ala Phe Asp Ile Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ser Val Leu Thr Gln Pro Pro Ser Ala Ser
    130                 135                 140

Gly Thr Pro Gly Gln Arg Val Thr Ile Ser Cys Thr Gly Ser Ser Ser
145                 150                 155                 160

Asn Ile Gly Ala Gly Tyr Asp Val His Trp Tyr Gln Gln Leu Pro Gly
                165                 170                 175

Thr Ala Pro Lys Leu Leu Ile Tyr Ser Asn Asn Gln Arg Pro Ser Gly
            180                 185                 190

Val Pro Asp Arg Phe Ser Gly Ser Lys Ser Gly Thr Ser Ala Ser Leu
        195                 200                 205

Ala Ile Ser Gly Leu Arg Ser Glu Asp Glu Ala Asp Tyr Tyr Cys Ala
    210                 215                 220

Ala Trp Asp Asp Ser Leu Ser Gly Pro Pro Trp Val Phe Gly Gly Gly
225                 230                 235                 240

Thr Lys Leu Thr Val Leu Gly Glu Gln Lys Leu Ile Ser Glu Glu Asp
                245                 250                 255

Leu Ser Gly Ser Ala Ala Ala His His His His His His
            260                 265

<210> SEQ ID NO 10
<211> LENGTH: 265
<212> TYPE: PRT
<213> ORGANISM: Artificial Sequence
<220> FEATURE:
<223> OTHER INFORMATION: CD40 (1)

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45
```

Ser Gly Ile Ser Gly Asn Gly Gly Tyr Thr Tyr Phe Ala Asp Ser Val
        50                  55                  60

Lys Asp Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Pro Val Asp Tyr Ser Asn Pro Ser Gly Met Asp Val Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Ser Gln Ser Val Leu Thr Gln Pro
        130                 135                 140

Pro Ser Ala Ser Gly Thr Pro Gly Gln Arg Val Thr Ile Ser Cys Ser
145                 150                 155                 160

Gly Ser Arg Ser Asn Ile Gly Leu Asn Thr Val Asn Trp Tyr Gln Gln
                165                 170                 175

Leu Pro Gly Thr Ala Pro Lys Leu Leu Ile Tyr Gly Asn Ser Asn Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Arg Ser Glu Asp Glu Ala Asp Tyr
    210                 215                 220

Tyr Cys Ala Gly Trp Asp Asp Ser Leu Ser Gly Trp Val Phe Gly Gly
225                 230                 235                 240

Gly Thr Lys Leu Thr Val Leu Gly Asp Tyr Lys Asp Asp Asp Asp Lys
                245                 250                 255

Ala Ala Ala His His His His His His
            260                 265

<210> SEQ ID NO 11
<211> LENGTH: 275
<212> TYPE: PRT
<213> ORGANISM: Artificial Sequence
<220> FEATURE:
<223> OTHER INFORMATION: Cystatin C (1)

<400> SEQUENCE: 11

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Gly Leu Ile Ser Tyr Asp Gly Arg Thr Thr Tyr Tyr Ala Asp Ser Val
        50                  55                  60

Lys Gly Arg Ser Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Thr Thr Thr Gly Thr Thr Leu Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Pro Ser Ala Ser Gly
    130                 135                 140

Thr Pro Gly Gln Arg Val Thr Ile Ser Cys Thr Gly Ser Ser Ser Asn
145                 150                 155                 160

Ile Gly Ala Gly Tyr Asp Val His Trp Tyr Gln Gln Leu Pro Gly Thr
            165                 170                 175

Ala Pro Lys Leu Leu Ile Tyr Gly Asn Thr Asn Arg Pro Ser Gly Val
            180                 185                 190

Pro Asp Arg Phe Ser Gly Ser Lys Ser Gly Thr Ser Ala Ser Leu Ala
            195                 200                 205

Ile Ser Gly Leu Arg Ser Glu Asp Glu Ala Asp Tyr Tyr Cys Ala Ala
            210                 215                 220

Trp Asp Asp Ser Leu Tyr Gly Trp Val Phe Gly Gly Gly Thr Lys Leu
225                 230                 235                 240

Thr Val Leu Gly Asp Tyr Lys Asp His Asp Gly Asp Tyr Lys Asp His
            245                 250                 255

Asp Ile Asp Tyr Lys Asp Asp Asp Asp Lys Ala Ala Ala His His His
            260                 265                 270

His His His
        275

<210> SEQ ID NO 12
<211> LENGTH: 280
<212> TYPE: PRT
<213> ORGANISM: Artificial Sequence
<220> FEATURE:
<223> OTHER INFORMATION: Apo-A1 (3)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Tyr
            20                  25                  30

Tyr Met Ser Trp Ile Arg Gln Ala Pro Gly Lys Gly Leu Glu Trp Val
            35                  40                  45

Ala Val Thr Ser Tyr Asp Gly Ser Lys Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Tyr Ala Asp Ser Ile Ala Ala Pro Ala Phe Asp Ile
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Gln Ser Val Leu Thr Gln
        130                 135                 140

Pro Pro Ser Ala Ser Gly Thr Pro Gly Gln Arg Val Thr Ile Ser Cys
145                 150                 155                 160

Thr Gly Ser Ser Ser Asn Ile Gly Ala Gly Tyr Asp Val His Trp Tyr
                165                 170                 175

Gln Gln Leu Pro Gly Thr Ala Pro Lys Leu Leu Ile Tyr Gly Asn Ser
            180                 185                 190

Asn Arg Pro Ser Gly Val Pro Asp Arg Phe Ser Gly Ser Lys Ser Gly
        195                 200                 205

Thr Ser Ala Ser Leu Ala Ile Ser Gly Leu Arg Ser Glu Asp Glu Ala
210                 215                 220

Asp Tyr Tyr Cys Gln Ser Tyr Asp Ser Ser Leu Ser Val Val Phe Gly
225                 230                 235                 240

Gly Gly Thr Lys Leu Thr Val Leu Gly Asp Tyr Lys Asp His Asp Gly
            245                 250                 255

Asp Tyr Lys Asp His Asp Ile Asp Tyr Lys Asp Asp Asp Asp Lys Ala
            260                 265                 270

Ala Ala His His His His His His
            275                 280

<210> SEQ ID NO 13
<211> LENGTH: 278
<212> TYPE: PRT
<213> ORGANISM: Artificial Sequence
<220> FEATURE:
<223> OTHER INFORMATION: Factor B (2)

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ala Val Ile Ser Tyr Asp Gly Arg Phe Ile Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Gly Gly Asn Leu Ala Met Asp Val Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Ala Gly Tyr Asp Val His Trp Tyr Gln Gln Leu Pro
                165                 170                 175

Gly Thr Ala Pro Lys Leu Leu Ile Tyr Asp Asn Asn Lys Arg Pro Ser
            180                 185                 190

Gly Val Pro Asp Arg Phe Ser Gly Ser Asn Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Arg Leu Asn Gly Arg Val Val Phe Gly Gly Gly
225                 230                 235                 240

Thr Lys Leu Thr Val Leu Gly Asp Tyr Lys Asp His Asp Gly Asp Tyr
                245                 250                 255

Lys Asp His Asp Ile Asp Tyr Lys Asp Asp Asp Asp Lys Ala Ala Ala
            260                 265                 270

His His His His His His
        275

-continued

```
<210> SEQ ID NO 14
<211> LENGTH: 276
<212> TYPE: PRT
<213> ORGANISM: Artificial Sequence
<220> FEATURE:
<223> OTHER INFORMATION: Factor B (4)

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys His
            20                  25                  30

Ser Met Asn Trp Val Arg Gln Ala Pro Gly Lys Gly Leu Glu Trp Val
        35                  40                  45

Ala Thr Val Ser Tyr Asp Gly Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Tyr Tyr Tyr Gly Met Asp Val Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Val Leu Thr Gln Pro Pro Ser Ala
    130                 135                 140

Ser Gly Thr Pro Gly Gln Arg Val Thr Ile Ser Cys Thr Gly Ser Ser
145                 150                 155                 160

Ser Asn Ile Gly Asn Asn Ala Val Asn Trp Tyr Gln Gln Leu Pro Gly
                165                 170                 175

Thr Ala Pro Lys Leu Leu Ile Tyr Asn Asn Asn Gln Arg Pro Ser Gly
            180                 185                 190

Val Pro Asp Arg Phe Ser Gly Ser Lys Ser Gly Thr Ser Ala Ser Leu
        195                 200                 205

Ala Ile Ser Gly Leu Arg Ser Glu Asp Glu Ala Asp Tyr Tyr Cys Gln
    210                 215                 220

Pro Tyr Asp Asp Ser Leu Ser Ser Val Val Phe Gly Gly Gly Thr Lys
225                 230                 235                 240

Leu Thr Val Leu Gly Asp Tyr Lys Asp His Asp Gly Asp Tyr Lys Asp
                245                 250                 255

His Asp Ile Asp Tyr Lys Asp Asp Asp Lys Ala Ala Ala His His
            260                 265                 270

His His His His
        275

<210> SEQ ID NO 15
<211> LENGTH: 275
<212> TYPE: PRT
<213> ORGANISM: Artificial Sequence
<220> FEATURE:
<223> OTHER INFORMATION: C4 (3)

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Trp Ser Thr Ser Ser Phe Asp Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Gln Ser Val Leu Thr Gln Pro Pro Ser Ala Ser
            130                 135                 140

Gly Thr Pro Gly Gln Arg Val Thr Ile Ser Cys Ser Gly Ser Ser Ser
145                 150                 155                 160

Asn Ile Gly Asn His Tyr Val Ser Trp Tyr Gln Gln Leu Pro Gly Thr
                165                 170                 175

Ala Thr Lys Leu Leu Ile Tyr Tyr Asp Asp Leu Leu Pro Ser Gly Val
            180                 185                 190

Pro Asp Arg Phe Ser Gly Ser Lys Ser Gly Thr Ser Ala Ser Leu Ala
            195                 200                 205

Ile Ser Gly Leu Arg Ser Glu Asp Glu Ala Asp Tyr Tyr Cys Ala Ala
            210                 215                 220

Trp Asp Asp Arg Ser Gly Gln Val Leu Phe Gly Gly Gly Thr Lys Leu
225                 230                 235                 240

Thr Val Leu Gly Asp Tyr Lys Asp His Asp Gly Asp Tyr Lys Asp His
                245                 250                 255

Asp Ile Asp Tyr Lys Asp Asp Asp Asp Lys Ala Ala Ala His His His
                260                 265                 270

His His His
        275

<210> SEQ ID NO 16
<211> LENGTH: 282
<212> TYPE: PRT
<213> ORGANISM: Artificial Sequence
<220> FEATURE:
<223> OTHER INFORMATION: C3 (3)

<400> SEQUENCE: 16

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Asn Trp Val Arg Gln Ala Pro Gly Lys Gly Leu Glu Trp Val
            35                  40                  45

Ala Asn Ile Asn Gln Asp Gly Ser Thr Lys Phe Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Thr Gly Gly Asn Tyr Leu Gly Gly Tyr Tyr Tyr Tyr Gly
            100                 105                 110
```

```
Met Asp Val Trp Gly Gln Gly Thr Leu Val Thr Val Ser Gly Gly
            115                 120                 125

Gly Gly Ser Gly Gly Gly Ser Gly Gly Gly Ser Gln Ser Val
        130                 135                 140

Leu Thr Gln Pro Pro Ser Ala Ser Gly Thr Pro Gly Gln Arg Val Thr
145                 150                 155                 160

Ile Ser Cys Ser Gly Ser Ser Asn Ile Gly Ser Asn Tyr Val Tyr
                165                 170                 175

Trp Tyr Gln Gln Leu Pro Gly Thr Ala Pro Lys Leu Leu Ile Tyr Arg
                180                 185                 190

Asn Asp Gln Arg Pro Ser Gly Val Pro Asp Arg Phe Ser Gly Ser Lys
                195                 200                 205

Ser Gly Thr Ser Ala Ser Leu Ala Ile Ser Gly Leu Arg Ser Glu Asp
        210                 215                 220

Glu Ala Asp Tyr Tyr Cys Ser Ser Tyr Ala Gly Asn Asn Asn Leu Val
225                 230                 235                 240

Phe Gly Gly Gly Thr Lys Leu Thr Val Leu Gly Asp Tyr Lys Asp His
                245                 250                 255

Asp Gly Asp Tyr Lys Asp His Asp Ile Asp Tyr Lys Asp Asp Asp Asp
                260                 265                 270

Lys Ala Ala Ala His His His His His His
            275                 280

<210> SEQ ID NO 17
<211> LENGTH: 272
<212> TYPE: PRT
<213> ORGANISM: Artificial Sequence
<220> FEATURE:
<223> OTHER INFORMATION: MYOM2 (1)
<220> FEATURE:
<221> NAME/KEY: VARIANT
<222> LOCATION: 224,242,247,249,251,254
<223> OTHER INFORMATION: Any amino acid

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Val Ala Gly Ser Trp Gly Gln Gly Thr Leu Val Thr
            100                 105                 110

Val Ser Ser Gly Gly Gly Gly Ser Gly Gly Gly Gly Ser Gly Gly Gly
        115                 120                 125

Gly Ser Gln Ser Val Leu Thr Gln Pro Pro Ser Ala Ser Gly Thr Pro
130                 135                 140

Gly Gln Arg Val Thr Ile Ser Cys Ser Gly Ser Ser Ser Asn Ile Gly
145                 150                 155                 160

Asn Asn Ala Val Asn Trp Tyr Gln Gln Leu Pro Gly Thr Ala Pro Lys
                165                 170                 175
```

Leu Leu Ile Tyr Asp Asn Asn Lys Arg Pro Ser Gly Val Pro Asp Arg
            180                 185                 190

Phe Ser Gly Ser Lys Ser Gly Thr Ser Ala Ser Leu Ala Ile Ser Gly
            195                 200                 205

Leu Arg Ser Glu Asp Glu Ala Asp Tyr Tyr Cys Ala Ala Trp Gly Xaa
            210                 215                 220

Gln Pro Glu Trp Leu Gly Val Arg Arg Asn Gln Ala Asp Ser Pro
225                 230                 235                 240

Arg Xaa Leu Gln Arg Pro Xaa Arg Xaa Leu Xaa Arg Ser Xaa His Arg
            245                 250                 255

Leu Gln Asp Asp Asp Lys Ala Ala Ala His His His His His His
            260                 265                 270

<210> SEQ ID NO 18
<211> LENGTH: 277
<212> TYPE: PRT
<213> ORGANISM: Artificial Sequence
<220> FEATURE:
<223> OTHER INFORMATION: CHX10 (3)

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Tyr Gly Asp Ser Ile Asn Trp Phe Asp Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Val Leu Thr Gln Pro Pro Ser
    130                 135                 140

Ala Ser Gly Thr Pro Gly Gln Arg Val Thr Ile Ser Cys Ser Gly Ser
145                 150                 155                 160

Ser Ser Asn Ile Arg Ser Asn Thr Val Asn Trp Tyr Gln Gln Leu Pro
                165                 170                 175

Gly Thr Ala Pro Lys Leu Leu Ile Tyr Gly Asn Ser Asn Arg Pro Ser
            180                 185                 190

Gly Val Pro Asp Arg Phe Ser Gly Ser Lys Ser Gly Thr Ser Ala Ser
        195                 200                 205

Leu Ala Ile Ser Gly Leu Arg Ser Glu Asp Glu Ala Asp Tyr Tyr Cys
    210                 215                 220

Ala Ala Trp Asp Asp Ser Leu Asn Gly Trp Val Phe Gly Gly Gly Thr
225                 230                 235                 240

Lys Leu Thr Val Leu Gly Asp Tyr Lys Asp His Asp Gly Asp Tyr Lys
                245                 250                 255

Asp His Asp Ile Asp Tyr Lys Asp Asp Asp Lys Ala Ala Ala His
            260                 265                 270

His His His His His
        275

<210> SEQ ID NO 19
<211> LENGTH: 271
<212> TYPE: PRT
<213> ORGANISM: Artificial Sequence
<220> FEATURE:
<223> OTHER INFORMATION: BTK (3)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Gly Met Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Gln Gln Thr Trp Tyr
    210                 215                 220

Leu Pro Thr Phe Gly Gln Gly Thr Lys Leu Glu Ile Lys Arg Leu Gly
225                 230                 235                 240

Asp Tyr Lys Asp His Asp Gly Asp Tyr Lys Asp His Asp Ile Asp Tyr
                245                 250                 255

Lys Asp Asp Asp Asp Lys Ala Ala Ala His His His His His His
            260                 265                 270

<210> SEQ ID NO 20
<211> LENGTH: 274
<212> TYPE: PRT
<213> ORGANISM: Artificial Sequence
<220> FEATURE:
<223> OTHER INFORMATION: HADH2 (3)

-continued

```
<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Tyr Met Ser Trp Val Arg Gln Ala Pro Gly Lys Gly Leu Glu Trp Val
        35                  40                  45

Ser Ser Ile Ser Ser Tyr Gly Tyr Tyr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Tyr Gly Ser Trp Tyr Phe Asp Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Gly
    210                 215                 220

Phe Val Gly Pro Ser Thr Phe Gly Gln Gly Thr Lys Leu Glu Ile Lys
225                 230                 235                 240

Arg Leu Gly Asp Tyr Lys Asp His Asp Gly Asp Tyr Lys Asp His Asp
                245                 250                 255

Ile Asp Tyr Lys Asp Asp Asp Asp Lys Ala Ala Ala His His His
                260                 265                 270

His His

<210> SEQ ID NO 21
<211> LENGTH: 284
<212> TYPE: PRT
<213> ORGANISM: Artificial Sequence
<220> FEATURE:
<223> OTHER INFORMATION: MATK (1)

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Tyr Met Gly Trp Val Arg Gln Ala Pro Gly Lys Gly Leu Glu Trp Val
        35                  40                  45

Ser Gly Ile Gly Gly Tyr Gly Tyr Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Tyr Asp Trp Gly His Ser Pro Gly Ser Trp Tyr Tyr Gly Ser
            100                 105                 110

Phe Asp Tyr Trp Gly Gln Gly Thr Leu Val Thr Val Ser Ser Gly Gly
            115                 120                 125

Gly Gly Ser Gly Gly Gly Ser Gly Gly Gly Ser Gln Ser Val
        130                 135                 140

Leu Thr Gln Pro Pro Ser Ala Ser Gly Thr Pro Gly Gln Arg Val Thr
145                 150                 155                 160

Ile Ser Cys Ser Gly Ser Ser Ser Asn Ile Gly Ser Ser Tyr Val Tyr
                165                 170                 175

Trp Tyr Gln Gln Leu Pro Gly Thr Ala Pro Lys Leu Leu Ile Tyr Ser
                180                 185                 190

Asn Asn Gln Arg Pro Ser Gly Val Pro Asp Arg Phe Ser Gly Ser Lys
                195                 200                 205

Ser Gly Thr Ser Ala Ser Leu Ala Ile Ser Gly Leu Arg Ser Glu Asp
        210                 215                 220

Glu Ala Asp Tyr Tyr Cys Ala Ala Trp Ala Gly Ala Tyr His Ser His
225                 230                 235                 240

Val Val Phe Gly Gly Gly Thr Lys Leu Thr Val Leu Gly Asp Tyr Lys
                245                 250                 255

Asp His Asp Gly Asp Tyr Lys Asp His Asp Ile Asp Tyr Lys Asp Asp
                260                 265                 270

Asp Asp Lys Ala Ala Ala His His His His His
        275                 280

<210> SEQ ID NO 22
<211> LENGTH: 273
<212> TYPE: PRT
<213> ORGANISM: Artificial Sequence
<220> FEATURE:
<223> OTHER INFORMATION: TNFRSF3 (2)

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Tyr Met Tyr Trp Val Arg Gln Ala Pro Gly Lys Gly Leu Glu Trp Val
            35                  40                  45

Ser Ser Ile Tyr Gly Ser Ser Ser Thr Ser Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Trp Asp Tyr Met Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Asp Ile Gln Met Thr Gln Ser Pro Ser Ser Leu
        130                 135                 140

Ser Ala Ser Val Gly Asp Arg Val Thr Ile Thr Cys Arg Ala Ser Gln
145                 150                 155                 160
```

```
Ser Ile Ser Ser Tyr Leu Asn Trp Tyr Gln Gln Lys Pro Gly Lys Ala
            165                 170                 175

Pro Lys Leu Leu Ile Tyr Ala Ala Ser Ser Leu Gln Ser Gly Val Pro
        180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ala
        210                 215                 220

Trp Asp Leu Pro Thr Phe Gly Gln Gly Thr Lys Leu Glu Ile Lys Arg
225                 230                 235                 240

Leu Gly Asp Tyr Lys Asp His Asp Gly Asp Tyr Lys Asp His Asp Ile
                245                 250                 255

Asp Tyr Lys Asp Asp Asp Asp Lys Ala Ala Ala His His His His His
                260                 265                 270

His

<210> SEQ ID NO 23
<211> LENGTH: 275
<212> TYPE: PRT
<213> ORGANISM: Artificial Sequence
<220> FEATURE:
<223> OTHER INFORMATION: UBC9 (3)

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Tyr Gly Ser Ser Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Ser Trp Gly Gly Tyr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
                180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
        210                 215                 220

Ser Gly Val Ser Pro Tyr Thr Phe Gly Gln Gly Thr Lys Leu Glu Ile
225                 230                 235                 240
```

```
Lys Arg Leu Gly Asp Tyr Lys Asp His Asp Gly Asp Tyr Lys Asp His
                245                 250                 255
Asp Ile Asp Tyr Lys Asp Asp Asp Asp Lys Ala Ala Ala His His His
                260                 265                 270
His His His
        275

<210> SEQ ID NO 24
<211> LENGTH: 272
<212> TYPE: PRT
<213> ORGANISM: Artificial Sequence
<220> FEATURE:
<223> OTHER INFORMATION: UBP7 (1)

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Ser
            20                  25                  30

Ser Met Tyr Trp Val Arg Gln Ala Pro Gly Lys Gly Leu Glu Trp Val
        35                  40                  45

Ser Ser Ile Ser Tyr Tyr Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Ile Asp Tyr Trp Gly Gln Gly Thr Leu Val Thr
            100                 105                 110

Val Ser Ser Gly Gly Gly Gly Ser Gly Gly Gly Ser Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Ser Ile Ser
145                 150                 155                 160

Ser Tyr Leu Asn Trp Tyr Gln Gln Lys Pro Gly Lys Ala Pro Lys Leu
                165                 170                 175

Leu Ile Tyr Ala Ala Ser Ser Leu Gln Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Trp Ser Val Tyr
    210                 215                 220

Gly Leu Tyr Thr Phe Gly Gln Gly Thr Lys Leu Glu Ile Lys Arg Leu
225                 230                 235                 240

Gly Asp Tyr Lys Asp His Asp Gly Asp Tyr Lys Asp His Asp Ile Asp
                245                 250                 255

Tyr Lys Asp Asp Asp Asp Lys Ala Ala Ala His His His His His His
            260                 265                 270

<210> SEQ ID NO 25
<211> LENGTH: 271
<212> TYPE: PRT
<213> ORGANISM: Artificial Sequence
<220> FEATURE:
<223> OTHER INFORMATION: UBP7 (2)
```

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Ser
            20                  25                  30

Ser Met Tyr Trp Val Arg Gln Ala Pro Gly Lys Gly Leu Glu Trp Val
        35                  40                  45

Ser Gly Ile Ser Tyr Tyr Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly His Ser Leu Asp Tyr Trp Gly Gln Gly Thr Leu Val Thr
            100                 105                 110

Val Ser Ser Gly Gly Gly Gly Ser Gly Gly Gly Ser Gly Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Ser Ile Ser
145                 150                 155                 160

Ser Tyr Leu Asn Trp Tyr Gln Gln Lys Pro Gly Lys Ala Pro Lys Leu
                165                 170                 175

Leu Ile Tyr Ala Ala Ser Ser Leu Gln Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Phe Ser Gly Tyr
    210                 215                 220

Pro His Thr Phe Gly Gln Gly Thr Lys Leu Glu Ile Lys Arg Leu Gly
225                 230                 235                 240

Asp Tyr Lys Asp His Asp Gly Asp Tyr Lys Asp His Asp Ile Asp Tyr
                245                 250                 255

Lys Asp Asp Asp Asp Lys Ala Ala Ala His His His His His His
            260                 265                 270

<210> SEQ ID NO 26
<211> LENGTH: 272
<212> TYPE: PRT
<213> ORGANISM: Artificial Sequence
<220> FEATURE:
<223> OTHER INFORMATION: APLF (2)

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Gly Tyr Tyr Asp Met Asp Tyr Trp Gly Gln Gly Thr Leu Val
            100                 105                 110

Thr Val Ser Ser Gly Gly Gly Gly Ser Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Ser Ile
145                 150                 155                 160

Ser Ser Tyr Leu Asn Trp Tyr Gln Gln Lys Pro Gly Lys Ala Pro Lys
                165                 170                 175

Leu Leu Ile Tyr Ala Ala Ser Ser Leu Gln Ser Gly Val Pro Ser Arg
            180                 185                 190

Phe Ser Gly Ser Gly Ser Gly Thr Asp Phe Thr Leu Thr Ile Ser Ser
            195                 200                 205

Leu Gln Pro Glu Asp Phe Ala Thr Tyr Tyr Cys Gln Gln Ser Tyr Ser
    210                 215                 220

Thr Pro Tyr Thr Phe Gly Gln Gly Thr Lys Leu Glu Ile Lys Arg Leu
225                 230                 235                 240

Gly Asp Tyr Lys Asp His Asp Gly Asp Tyr Lys Asp His Asp Ile Asp
                245                 250                 255

Tyr Lys Asp Asp Asp Asp Lys Ala Ala Ala His His His His His His
                260                 265                 270

<210> SEQ ID NO 27
<211> LENGTH: 279
<212> TYPE: PRT
<213> ORGANISM: Artificial Sequence
<220> FEATURE:
<223> OTHER INFORMATION: MARK1-1 (1)

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Gly Trp Val Arg Gln Ala Pro Gly Lys Gly Leu Glu Trp Val
        35                  40                  45

Ser Ser Ile Ser Tyr Tyr Gly Gly Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Asp Phe Tyr Ala Ser His Tyr Gly Ile Tyr Ile Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Ser Ser Tyr Leu Asn Trp Tyr Gln
                165                 170                 175
```

-continued

```
Gln Lys Pro Gly Lys Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ala Ser Ser Leu Phe Thr Phe Gly Gln Gly Thr
225                 230                 235                 240

Lys Leu Glu Ile Lys Arg Leu Gly Asp Tyr Lys Asp His Asp Gly Asp
                245                 250                 255

Tyr Lys Asp His Asp Ile Asp Tyr Lys Asp Asp Asp Asp Lys Ala Ala
            260                 265                 270

Ala His His His His His His
        275

<210> SEQ ID NO 28
<211> LENGTH: 275
<212> TYPE: PRT
<213> ORGANISM: Artificial Sequence
<220> FEATURE:
<223> OTHER INFORMATION: PTPPRN2 (1)

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Ala Ser Ser Ala Tyr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Tyr Ser Thr Pro Tyr Thr Phe Gly Gln Gly Thr Lys Leu Glu Ile
225                 230                 235                 240

Lys Arg Leu Gly Asp Tyr Lys Asp His Asp Gly Asp Tyr Lys Asp His
                245                 250                 255
```

```
Asp Ile Asp Tyr Lys Asp Asp Asp Lys Ala Ala Ala His His
            260                 265                 270
His His His
        275

<210> SEQ ID NO 29
<211> LENGTH: 273
<212> TYPE: PRT
<213> ORGANISM: Artificial Sequence
<220> FEATURE:
<223> OTHER INFORMATION: CEACAM5 (1)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Tyr Met Asn Trp Val Arg Gln Ala Pro Gly Lys Gly Leu Glu Trp Val
        35                  40                  45

Ser Gly Ile Ser Gly Asn Gly Gly Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Pro Ala Tyr Phe Asp Tyr Trp Gly Gln Gly Thr
            100                 105                 110

Leu Val Thr Val Ser Ser Gly Gly Gly Ser Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Gly
    210                 215                 220

Tyr Tyr Pro His Thr Phe Gly Gln Gly Thr Lys Leu Glu Ile Lys Arg
225                 230                 235                 240

Leu Gly Asp Tyr Lys Asp His Asp Gly Asp Tyr Lys Asp His Asp Ile
                245                 250                 255

Asp Tyr Lys Asp Asp Asp Asp Lys Ala Ala Ala His His His His
            260                 265                 270

His

<210> SEQ ID NO 30
<211> LENGTH: 270
<212> TYPE: PRT
<213> ORGANISM: Artificial Sequence
<220> FEATURE:
<223> OTHER INFORMATION: MUC16 (1)
```

-continued

```
<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Gly Ile Gly Tyr Tyr Gly Ser Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Phe Asp Tyr Trp Gly Gln Gly Thr Leu Val Thr
            100                 105                 110

Val Ser Ser Gly Gly Gly Gly Ser Gly Gly Gly Ser Gly Gly Gly Gly
        115                 120                 125

Gly Ser Asp Ile Gln Met Thr Gln Ser Pro Ser Ser Leu Ser Ala Ser
    130                 135                 140

Val Gly Asp Arg Val Thr Ile Thr Cys Arg Ala Ser Gln Ser Ile Ser
145                 150                 155                 160

Ser Tyr Leu Asn Trp Tyr Gln Gln Lys Pro Gly Lys Ala Pro Lys Leu
                165                 170                 175

Leu Ile Tyr Ala Ala Ser Ser Leu Gln Ser Gly Val Pro Ser Arg Phe
            180                 185                 190

Ser Gly Ser Gly Ser Gly Thr Asp Phe Thr Leu Thr Ile Ser Ser Leu
        195                 200                 205

Gln Pro Glu Asp Phe Ala Thr Tyr Tyr Cys Gln Gln Gly Phe Tyr Pro
    210                 215                 220

Tyr Thr Phe Gly Gln Gly Thr Lys Leu Glu Ile Lys Arg Leu Gly Asp
225                 230                 235                 240

Tyr Lys Asp His Asp Gly Asp Tyr Lys Asp His Asp Ile Asp Tyr Lys
                245                 250                 255

Asp Asp Asp Asp Lys Ala Ala Ala His His His His His
            260                 265                 270

<210> SEQ ID NO 31
<211> LENGTH: 271
<212> TYPE: PRT
<213> ORGANISM: Artificial Sequence
<220> FEATURE:
<223> OTHER INFORMATION: MMP9 (2)

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30

Tyr Met Ser Trp Val Arg Gln Ala Pro Gly Lys Gly Leu Glu Trp Val
        35                  40                  45

Ser Ser Ile Asn Ser Ser Gly Asn Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Ser Val Tyr Leu Asp Tyr Trp Gly Gln Gly Thr Leu Val Thr
            100                 105                 110

Val Ser Ser Gly Gly Gly Gly Ser Gly Gly Gly Gly Ser Gly Gly Gly
            115                 120                 125

Gly Ser Asp Ile Gln Met Thr Gln Ser Pro Ser Ser Leu Ser Ala Ser
            130                 135                 140

Val Gly Asp Arg Val Thr Ile Thr Cys Arg Ala Ser Gln Ser Ile Ser
145                 150                 155                 160

Ser Tyr Leu Asn Trp Tyr Gln Gln Lys Pro Gly Lys Ala Pro Lys Leu
                165                 170                 175

Leu Ile Tyr Ala Ala Ser Ser Leu Gln Ser Gly Val Pro Ser Arg Phe
            180                 185                 190

Ser Gly Ser Gly Ser Gly Thr Asp Phe Thr Leu Thr Ile Ser Ser Leu
            195                 200                 205

Gln Pro Glu Asp Phe Ala Thr Tyr Tyr Cys Gln Gln Phe Ser Gly Tyr
    210                 215                 220

Pro Tyr Thr Phe Gly Gln Gly Thr Lys Leu Glu Ile Lys Arg Leu Gly
225                 230                 235                 240

Asp Tyr Lys Asp His Asp Gly Asp Tyr Lys Asp His Asp Ile Asp Tyr
                245                 250                 255

Lys Asp Asp Asp Asp Lys Ala Ala His His His His His His
                260                 265                 270

<210> SEQ ID NO 32
<211> LENGTH: 273
<212> TYPE: PRT
<213> ORGANISM: Artificial Sequence
<220> FEATURE:
<223> OTHER INFORMATION: IGFBP3 (2)
<220> FEATURE:
<221> NAME/KEY: VARIANT
<222> LOCATION: 214
<223> OTHER INFORMATION: Any amino acid

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ile Val Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160
```

```
Ile Ser Ser Tyr Leu Asn Trp Tyr Gln Gln Lys Pro Gly Lys Ala Pro
            165                 170                 175

Lys Leu Leu Ile Tyr Ala Ala Ser Ser Leu Gln Ser Gly Val Pro Ser
        180                 185                 190

Arg Phe Ser Gly Ser Gly Ser Gly Thr Asp Phe Thr Leu Thr Ile Ser
        195                 200                 205

Ser Leu Gln Pro Glu Xaa Phe Ala Thr Tyr Tyr Cys Gln Gln Ser Tyr
        210                 215                 220

Ser Thr Pro Tyr Thr Phe Gly Gln Gly Thr Lys Leu Glu Ile Lys Arg
225                 230                 235                 240

Leu Gly Asp Tyr Lys Asp His Asp Gly Asp Tyr Lys Asp His Asp Ile
                245                 250                 255

Asp Tyr Lys Asp Asp Asp Asp Lys Ala Ala Ala His His His His His
                260                 265                 270

His
```

<210> SEQ ID NO 33
<211> LENGTH: 274
<212> TYPE: PRT
<213> ORGANISM: Artificial Sequence
<220> FEATURE:
<223> OTHER INFORMATION: IL-2ra (3)

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Trp Tyr Gly Phe Asp Tyr Trp Gly Gln Gly Thr
            100                 105                 110

Leu Val Thr Val Ser Ser Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
    210                 215                 220

Tyr Ser Thr Pro Tyr Thr Phe Gly Gln Gly Thr Lys Leu Glu Ile Lys
225                 230                 235                 240
```

```
Arg Leu Gly Asp Tyr Lys Asp His Asp Gly Asp Tyr Lys Asp His Asp
                245                 250                 255

Ile Asp Tyr Lys Asp Asp Asp Asp Lys Ala Ala Ala His His His His
            260                 265                 270

His His
```

```
<210> SEQ ID NO 34
<211> LENGTH: 277
<212> TYPE: PRT
<213> ORGANISM: Artificial Sequence
<220> FEATURE:
<223> OTHER INFORMATION: AGR2 (1)
<220> FEATURE:
<221> NAME/KEY: VARIANT
<222> LOCATION: 217
<223> OTHER INFORMATION: Any amino acid

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Ser
            20                  25                  30

Tyr Met Ser Trp Val Arg Gln Ala Pro Gly Lys Gly Leu Glu Trp Val
        35                  40                  45

Ser Gly Ile Ser Gly Tyr Tyr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ser Ser Tyr His Tyr Ser Tyr Ile Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Ser Ile Ser Ser Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
            180                 185                 190

Val Pro Ser Arg Phe Ser Gly Ser Gly Ser Gly Thr Asp Phe Thr Leu
        195                 200                 205

Thr Ile Ser Ser Leu Gln Pro Glu Xaa Phe Ala Thr Tyr Tyr Cys Gln
    210                 215                 220

Gln Ser Tyr Tyr Trp Gly Leu Phe Thr Phe Gly Gln Gly Thr Lys Leu
225                 230                 235                 240

Glu Ile Lys Arg Leu Gly Asp Tyr Lys Asp His Asp Gly Asp Tyr Lys
                245                 250                 255

Asp His Asp Ile Asp Tyr Lys Asp Asp Asp Asp Lys Ala Ala Ala His
            260                 265                 270

His His His His His
        275
```

-continued

```
<210> SEQ ID NO 35
<211> LENGTH: 275
<212> TYPE: PRT
<213> ORGANISM: Artificial Sequence
<220> FEATURE:
<223> OTHER INFORMATION: IGFBP2 (1)
<220> FEATURE:
<221> NAME/KEY: VARIANT
<222> LOCATION: 191,201,216
<223> OTHER INFORMATION: Any amino acid

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Ser Met Tyr Trp Val Arg Gln Ala Pro Gly Lys Gly Leu Glu Trp Val
        35                  40                  45

Ser Ser Ile Gly Ser Tyr Gly Tyr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Trp Ser Gly Phe His Tyr Ile Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Xaa Val
            180                 185                 190

Pro Ser Arg Phe Ser Gly Ser Gly Xaa Gly Thr Asp Phe Thr Leu Thr
        195                 200                 205

Ile Ser Ser Leu Gln Pro Glu Xaa Phe Ala Thr Tyr Tyr Cys Gln Gln
    210                 215                 220

Gly Tyr Val His Leu Leu Thr Phe Gly Gln Gly Thr Lys Leu Glu Ile
225                 230                 235                 240

Lys Arg Leu Gly Asp Tyr Lys Asp His Asp Gly Asp Tyr Lys Asp His
                245                 250                 255

Asp Ile Asp Tyr Lys Asp Asp Asp Asp Lys Ala Ala Ala His His His
            260                 265                 270

His His His
        275

<210> SEQ ID NO 36
<211> LENGTH: 275
<212> TYPE: PRT
<213> ORGANISM: Artificial Sequence
<220> FEATURE:
<223> OTHER INFORMATION: OPG (2)
```

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Phe Tyr Ser Tyr Ser Gly Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Tyr Gly Tyr Tyr Pro Leu Thr Phe Gly Gln Gly Thr Lys Leu Glu Ile
225                 230                 235                 240

Lys Arg Leu Gly Asp Tyr Lys Asp His Asp Gly Asp Tyr Lys Asp His
                245                 250                 255

Asp Ile Asp Tyr Lys Asp Asp Asp Lys Ala Ala Ala His His His His
            260                 265                 270

His His His
        275
```

<210> SEQ ID NO 37
<211> LENGTH: 277
<212> TYPE: PRT
<213> ORGANISM: Artificial Sequence
<220> FEATURE:
<223> OTHER INFORMATION: GDF-15 (1)
<220> FEATURE:
<221> NAME/KEY: VARIANT
<222> LOCATION: 210,225
<223> OTHER INFORMATION: Any amino acid

<400> SEQUENCE: 37

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
        35                  40                  45
```

Ser Ser Ile Tyr Gly Tyr Gly Tyr Tyr Thr Tyr Tyr Ala Asp Ser Val
50                  55                      60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Arg Gly Gly Tyr Phe His Gly Val Ser Asp Met Asp Tyr Trp Gly
        100                 105                 110

Gln Gly Thr Leu Val Thr Val Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
            195                 200                 205

Leu Xaa Ile Ser Ser Leu Gln Pro Glu Asp Phe Ala Thr Tyr Tyr Cys
210                 215                 220

Xaa Gln Tyr Tyr Asn Tyr Leu His Thr Phe Gly Gln Gly Thr Lys Leu
225                 230                 235                 240

Glu Ile Lys Arg Leu Gly Asp Tyr Lys Asp His Asp Gly Asp Tyr Lys
            245                 250                 255

Asp His Asp Ile Asp Tyr Lys Asp Asp Asp Asp Lys Ala Ala Ala His
            260                 265                 270

His His His His His
        275

<210> SEQ ID NO 38
<211> LENGTH: 271
<212> TYPE: PRT
<213> ORGANISM: Artificial Sequence
<220> FEATURE:
<223> OTHER INFORMATION: CEACAM5 (3)
<220> FEATURE:
<221> NAME/KEY: VARIANT
<222> LOCATION: 220
<223> OTHER INFORMATION: Any amino acid

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Tyr Met Tyr Trp Val Arg Gln Ala Pro Gly Lys Gly Leu Glu Trp Val
        35                  40                  45

Ser Gly Ile Ser Ser Ser Gly Tyr Ser Thr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Arg Tyr Gly Tyr Tyr Phe Asp Tyr Trp Gly Gln Gly Thr Leu Val
        100                 105                 110

```
Thr Val Ser Ser Gly Gly Gly Ser Gly Gly Gly Ser Gly Gly
        115             120             125

Gly Gly Ser Asp Ile Gln Met Thr Gln Ser Pro Ser Ser Leu Ser Ala
    130             135             140

Ser Val Gly Asp Arg Val Thr Ile Thr Cys Arg Ala Ser Gln Ser Ile
145             150             155             160

Ser Ser Tyr Leu Asn Trp Tyr Gln Gln Lys Pro Gly Lys Ala Pro Lys
            165             170             175

Leu Leu Ile Tyr Ala Ala Ser Ser Leu Gln Ser Gly Val Pro Ser Arg
            180             185             190

Phe Ser Gly Ser Gly Ser Gly Thr Asp Phe Thr Leu Thr Ile Ser Ser
        195             200             205

Leu Gln Pro Glu Asp Phe Ala Thr Tyr Tyr Cys Xaa Gln Phe Gly Tyr
        210             215             220

Pro Pro Thr Phe Gly Gln Gly Thr Lys Leu Glu Ile Lys Arg Leu Gly
225             230             235             240

Asp Tyr Lys Asp His Asp Gly Asp Tyr Lys Asp His Asp Ile Asp Tyr
            245             250             255

Lys Asp Asp Asp Asp Lys Ala Ala Ala His His His His His His
            260             265             270
```